United States Patent
Corbett et al.

(10) Patent No.: US 7,834,013 B2
(45) Date of Patent: Nov. 16, 2010

(54) AMINOPHENYLCYCLOPROPYL CARBOXYLIC ACIDS AND DERIVATIVES AS AGONISTS TO GPR40

(75) Inventors: David Francis Corbett, Harlow (GB); Kate Anna Dwornik, Durham, NC (US); Dulce Maria Garrido, Durham, NC (US); Stephen Carl McKeown, Hitchin (GB); Wendy Yoon Mills, Durham, NC (US); Andrew James Peat, Durham, NC (US); Terrence Lee Smalley, Jr., Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 506 days.

(21) Appl. No.: 10/595,892

(22) PCT Filed: Nov. 15, 2004

(86) PCT No.: PCT/US2004/038126
§ 371 (c)(1),
(2), (4) Date: Oct. 29, 2008

(87) PCT Pub. No.: WO2005/051890
PCT Pub. Date: Jun. 9, 2005

(65) Prior Publication Data
US 2009/0105257 A1    Apr. 23, 2009

Related U.S. Application Data

(60) Provisional application No. 60/523,532, filed on Nov. 19, 2003.

(51) Int. Cl.
| | |
|---|---|
| *A61K 31/5375* | (2006.01) |
| *A61K 31/4439* | (2006.01) |
| *A61K 31/426* | (2006.01) |
| *A61K 31/381* | (2006.01) |
| *A61K 31/196* | (2006.01) |
| *C07D 295/14* | (2006.01) |
| *C07D 417/12* | (2006.01) |
| *C07D 277/20* | (2006.01) |
| *C07D 333/24* | (2006.01) |
| *C07C 229/46* | (2006.01) |

(52) U.S. Cl. .................... 514/237.8; 514/342; 514/365; 514/438; 514/567; 544/162; 546/269.7; 548/204; 549/77; 562/469

(58) Field of Classification Search ............. 514/237.8, 514/567, 357, 369, 365, 471, 438, 342; 562/469; 546/335, 269.7; 548/187, 204; 549/77; 544/165
See application file for complete search history.

(56) References Cited

U.S. PATENT DOCUMENTS 5,773,644 A * 6/1998 Chen et al. .................. 562/439

FOREIGN PATENT DOCUMENTS

WO    WO02/057783    7/2002

OTHER PUBLICATIONS

Vippagunta et al., Crystalline solids, 2001, Advanced Drug Delivery Reviews, 48, pp. 3-26.*
Wolff et al., Burger's Medicinal Chemistry and Drug Discovery, 1994, Wiley-Interscience, Fifth Edition, vol. I: Principles and Practice, pp. 975-977.*
Itoh et al., "Free fatty acids regulate insuling secretion from pancreatic beta cells through GPR40," Nature, V422, N6928, pp. 173-176.

* cited by examiner

*Primary Examiner*—Kamal A Saeed
*Assistant Examiner*—Kristin Bianchi
(74) *Attorney, Agent, or Firm*—Bonnie L. Deppenbrock

(57) ABSTRACT

The present invention relates generally to novel therapeutic compounds and more particularly to novel compounds, their use as GPR40 agonists, processes for their manufacture, and intermediates useful in their preparation.

24 Claims, No Drawings

AMINOPHENYLCYCLOPROPYL CARBOXYLIC ACIDS AND DERIVATIVES AS AGONISTS TO GPR40

This application is filed pursuant to 35 U.S.C. §371 as a United States National Phase Application of International Application No. PCT/US2004/038126 filed Nov. 15, 2004, which claims priority from US 60/523,532 filed Nov. 19, 2003.

FIELD OF THE INVENTION

The present invention relates generally to novel therapeutic compounds and more particularly to novel compounds, their use as GPR40 agonists, processes for their manufacture, and intermediates useful in their preparation.

BACKGROUND OF THE INVENTION

Diabetes mellitus is an ever-increasing threat to human health. For example, in the United States current estimates maintain that about 16 million people suffer from diabetes mellitus.

Type I diabetes, also known as insulin-dependent diabetes mellitus (IDDM), is caused by the autoimmune destruction of the insulin producing pancreatic β-cells, and necessitates regular administration of exogenous insulin. Without insulin, cells cannot absorb sugar (glucose), which they need to produce energy. Symptoms of Type I diabetes usually start in childhood or young adulthood. People often seek medical help because they are seriously ill from sudden symptoms of high blood sugar (hyperglycemia).

Type II diabetes, also known as non-insulin-dependent diabetes mellitus, manifests as an inability to adequately regulate blood-glucose levels. Type II diabetes may be characterized by a defect in insulin secretion or by insulin resistance, namely those that suffer from Type II diabetes have too little insulin or cannot use insulin effectively. Insulin resistance refers to the inability of the body tissues to respond properly to endogenous insulin. Insulin resistance develops because of multiple factors, including genetics, obesity, increasing age, and having high blood sugar over long periods of time. Type II diabetes, sometimes called mature onset, can develop at any age, but most commonly becomes apparent during adulthood. The incidence of type II diabetes in children, however, is rising.

In diabetics glucose levels build up in the blood and urine causing excessive urination, thirst, hunger, and problems with fat and protein metabolism. If left untreated, diabetes mellitus may cause life-threatening complications, including blindness, kidney failure, and heart disease.

Type II diabetes accounts for approximately 90-95% of diabetes cases, killing about 193,000 U.S. residents each year. Type II diabetes is the seventh leading cause of all deaths. In Western societies, type II diabetes currently affects 6% of the adult population with world-wide frequency expected to grow by 6% per annum. Although there are certain inheritable traits that may predispose particular individuals to developing type II diabetes, the driving force behind the current increase in incidence of the disease is the increased sedentary lifestyle, diet, and obesity now prevalent in developed countries. About 80% of diabetics with type ii diabetes are significantly overweight. As noted above, an increasing number of young people are developing the disease. Type II diabetes is now internationally recognized as one of the major threats to human health in the 21$^{st}$ century.

Type II diabetes currently is treated at several levels. A first level of therapy is through diet and/or exercise, either alone or in combination with therapeutic agents. Such agents may include insulin or pharmaceuticals that lower blood glucose levels. About 49% of individuals with Type II diabetes require oral medications, about 40% require insulin injections or a combination of insulin injections and oral medications, and 10% use diet and exercise alone.

Current therapies include: insulin secretagogues, such as sulphonylureas, which increase insulin production from pancreatic β-cells; glucose-lowering effectors, such as metformin which reduce glucose production from the liver; activators of the peroxisome proliferator-activated receptors-γ (PPAR-γ), such as the thiazolidinediones, which enhances insulin action; and α-glucosidase inhibitors which interfere with gut glucose production. There are, however, deficiencies associated with currently available treatments. For example sulphonylureas and insulin injections can be associated with hypoglycemic episodes and weight gain. Furthermore, patients often lose responsiveness to sulphonylureas over time. Metformin and α-glucosidase inhibitors often lead to gastrointestinal problems and PPAR-γ agonists tend to cause increased weight gain and edema.

There are several areas at which research is being targeted in order to bring new, more effective, therapies to the marketplace. As one example, the present inventors are exploring a reduction in excessive hepatic glucose production, enhancing the pathway by which insulin transmits its signal to the cells such that they take up glucose, enhancing glucose-stimulated insulin secretion from the pancreatic β-cells, and targeting obesity and associated problems with fat metabolism and accumulation.

Free fatty acids (FFA) play key roles in several aspects of metabolism, including the 'priming' of the pancreatic β-cell to potentiate the insulin response to glucose in the fasted state and as a starting point in lipogenesis. GPR40 is the first cell-surface receptor identified for fatty acids most prevalent in plasma such as palmitate, oleate, stearate, linoleate, and linolenate. GPR40 could be considered to be a 'nutrient sensing' receptor, playing several tissue-dependent roles which may inter-play to effect overall glucose disposal and/or fat metabolism. For example, and herein incorporated by reference, Itoh et al. (Nature, 23 Feb. 2003, doi:10.1038/nature01478) describe that long-chain FFAs amplify glucose-stimulated insulin secretion from the pancreatic β cells through activation of GPR40.

On this basis, agonists to GPR40 may be of therapeutic value for diabetes and associated conditions, particularly type II diabetes, obesity, glucose intolerance, insulin resistance, metabolic syndrome X, hyperlipidemia, hypercholesterolemia, atherosclerosis, neurodegenerative diseases (for example Alzheimer's disease), and other indications such as stroke.

SUMMARY OF THE INVENTION

The present invention includes compounds of formula (I)

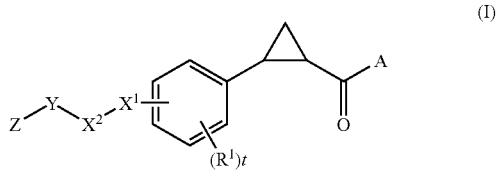

(I)

including salts, solvates, and pharmaceutically functional derivatives thereof, wherein t is 0, 1, 2, 3, or 4;
$R^1$ is alkyl, alkoxy, halogen, haloalkyl, nitro, cyano, or —$NR^7R^8$, where each of $R^7$ and $R^8$ independently are H or alkyl;
A is —OH or —$NR^2R^3$;
each of $R^2$ and $R^3$ independently is H or -$(Q^1)_n$-$R^4$;
n is 0, 1 or 2;
$Q^1$ is alkylene;
each $R^4$ independently is alkyl, haloalkyl, aryl, heteroaryl, cycloalkyl, heterocyclyl, hydroxy, alkoxy, or aryloxy;
$X^1$ is —NH—;
$X^2$ is —$C(R^5)_2$—;
each $R^5$ independently is H or alkyl;
Y is aryl or heteroaryl;
Z is -$(Q^2)_m$-$R^6$;
m is 0 or 1;
$Q^2$ is —$NR^5$—, —O—, —S—, —$O(CH_2)_p$—, or —$CH_2$—;
p is 1, 2, or 3; and
$R^6$ is aryl or heteroaryl.

Preferably $X^2$ is —$CH_2$—. Preferably $X^1$ is substituted para to the depicted cyclopropyl ring.

Preferably t is 0.

Preferably Y is aryl. Preferably Y is phenyl. Preferably when Y is phenyl, the phenyl is unsubstituted or is optionally substituted with $C_1$-$C_6$ alkyl, $C_1$-$C_6$ alkoxy, halogen, or $C_1$-$C_6$ haloalkyl.

In another embodiment preferably Y is heteroaryl. Preferably Y is thiazolyl. Preferably when Y is thiazolyl, the thiazolyl is unsubstituted or is optionally substituted with $C_1$-$C_6$ alkyl, aryl, or heteroaryl.

Preferably A is —OH. In addition, the compound of formula (I) may be a pharmaceutically functional derivative. Thus, the present invention includes where A is —$OR^9$, where $R^9$ is alkyl or aryl.

Preferably $Q^1$ is unsubstituted alkylene. In another embodiment $Q^1$ is optionally substituted alkylene.

Preferably Z is —O—$R^3$. Preferably $R^6$ is phenyl. Preferably when $R^6$ is phenyl, the phenyl is unsubstituted or is optionally substituted with halogen, $C_1$-$C_6$ haloalkyl, $C_1$-$C_6$ alkyl, or $C_1$-$C_6$ alkoxy.

In another embodiment Z is —$R^6$. Preferably $R^6$ is phenyl. Preferably when $R^6$ is phenyl, the phenyl is unsubstituted or is optionally substituted with halogen, $C_1$-$C_6$ haloalkyl, $C_1$-$C_6$ alkyl, or $C_1$-$C_6$ alkoxy. In another embodiment $R^6$ is heteroaryl.

In one embodiment A is —OH, t is 0, $X^1$ is —NH—, $X^2$ is —$CH_2$—, Y is phenyl, m is 1, $Q^2$ is —O—, and $R^6$ is phenyl.

In another embodiment A is —OH, t is 0, $X^1$ is —NH—, $X^2$ is —$CH_2$—, Y is thiazolyl, m is 0, and $R^6$ is phenyl substituted with —$CF_3$.

Particularly preferred compounds include:

Racemic-(trans)-2-[4-({[3-(phenyloxy)phenyl]methyl}amino)phenyl]cyclopropanecarboxylic acid;
Racemic-(trans)2{4-[(4-biphenylylmethyl)amino]phenyl}cyclopropanecarboxylic acid;
Racemic-(trans)-2-[4-({[4-(2-pyridinyl)phenyl]methyl}amino)phenyl]cyclopropanecarboxylic acid;
Racemic-(trans)-2-{4-[({3-[(3,4-dichlorophenyl)oxy]phenyl}methyl)ammonium]phenyl}-cyclopropanecarboxylic acid;
Racemic-(trans)-2-(4-{[(3-{[(4-(methyloxy)phenyl]oxy}phenyl)methyl]ammonium}phenyl)-cyclopropanecarboxylic acid;
Racemic-(trans)-2-{4-[({3-[(4-chlorophenyl)oxy]phenyl}methyl)ammonium]phenyl}cyclopropanecarboxylic acid;
Racemic-(trans)-2-(4-{[(3-{[4-(1,1-dimethylethyl)phenyl]oxy}phenyl)methyl]ammonium}phenyl)cyclopropanecarboxylic acid;
Racemic-(trans)-2-{4-[({3-[(3,5-dichlorophenyl)oxy]phenyl}methyl)ammonium]phenyl}-cyclopropanecarboxylic acid;
Racemic-(trans)-2-(4{[(3{[3-(trifluoromethyl)phenyl]oxy}phenyl)methyl]ammonium}phenyl)cyclopropanecarboxylic acid;
Racemic-(trans)-2-{4-[({3-[(4-methylphenyl)oxy]phenyl}methyl)ammonium]phenyl}-cyclopropanecarboxylic acid;
Racemic-(trans)-2-{4-[({3-[(phenylmethyl)oxy]phenyl}methyl)ammonium]phenyl}-cyclopropanecarboxylic acid;
Racemic-(trans)-2-[4-({[4-methyl-2-(phenyloxy)-1,3-thiazol-5-yl]methyl}ammonium)-phenyl]cyclopropanecarboxylic acid;
Racemic-(trans)-2-{4-[({4-methyl-2-[4-(trifluoromethyl)phenyl]-1,3-thiazol-5-yl}methyl)amino]phenyl}cyclopropanecarboxylic acid;
Racemic-(trans)-2-{4-[({4-isopropyl-2-[4-(trifluoromethyl)phenyl]-1,3-thiazol-5-yl}methyl)amino]phenyl}cyclopropanecarboxylic acid;
Racemic-(trans)-2-[4-({[5-(4-chlorophenyl)-2-furanyl]methyl}amino)phenyl]cyclopropanecarboxylic acid;
Racemic-(trans)-2-{4-[({4-[(phenylmethyl)oxy]phenyl}methyl)amino]phenyl}cyclopropanecarboxylic acid;
Racemic-(trans)-2-{4-[({2-[(3,4-difluorophenyl)oxy]-4-methyl-1,3-thiazol-5-yl}methyl)amino]phenyl}cyclopropanecarboxylic acid;
Racemic-(trans)-2-(4-[({5-[4-(trifluoromethyl)phenyl]-2-furanyl}methyl)amino]phenyl}cyclopropanecarboxylic acid;
Racemic-(trans)-2-{4-[({5-[4-(trifluoromethyl)phenyl]-2-thienyl}methyl)amino]phenyl}cyclopropanecarboxylic acid;
Racemic-(trans)-2-{4-[({4-[4-(trifluoromethyl)phenyl]-2-furanyl}methyl)amino]phenyl}cyclopropanecarboxylic acid;
Racemic-(trans)2-[4-({[3-(phenylmethyl)phenyl]methyl}amino)phenyl]cyclopropanecarboxylic acid;
Racemic-(trans)2-{4-[({3-[(4-nitrophenyl)oxy]phenyl}methyl)amino]phenyl}cyclopropanecarboxylic acid;
Racemic-(trans)-2-[4-({[3-(phenylthio)phenyl]methyl}amino)phenyl]cyclopropanecarboxylic acid;
Racemic-(trans)-2-{4-[({3-[(4-aminophenyl)oxy]phenyl}methyl)amino]phenyl}cyclopropanecarboxylic acid;
(−)-(Trans)-2-[4-({[3-(phenyloxy)phenyl]methyl}amino)phenyl]cyclopropane carboxylic acid;
(+)-(Trans)-2-{4-[(3-phenoxybenzyl)amino]phenyl}cyclopropanecarboxylic acid;
(+)-(Trans)-2-{4-[({4-methyl-2-[4-(trifluoromethyl)phenyl]-1,3-thiazol-5-yl}methyl)amino]phenyl}cyclopropanecarboxylic acid;
Enantiomerically enriched (trans)-ethyl-2-{4-[({3-[(3,4-dichlorophenyl)oxy]phenyl}methyl)amino]phenyl}-cyclopropanecarboxylate;
(+)-(Trans)-2-{4-[({3-[(3,4-dichlorophenyl)oxy]phenyl}methyl)amino]phenyl}cyclopropanecarboxylic acid;
(−)-(cis)-2-{4-[({4-methyl-2-[4-(trifluoromethyl)phenyl]-1,3-thiazol-5-yl}methyl)amino]phenyl}cyclopropanecarboxylic acid;
Enantiomerically enriched-(trans)-ethyl-2-[2-chloro-4-({[3-(phenyloxy)phenyl]methyl}amino)phenyl]cyclopropanecarboxylate;

(+)-(Trans)-2-[2-chloro-4-({[3-(phenyloxy)phenyl]
methyl}amino)phenyl]cyclopropanecarboxylic acid;

Enantiomerically enriched-(trans)-ethyl-2-[2,5-difluoro-4-
({[3-(phenyloxy)phenyl]methyl}amino)phenyl]cyclopropanecarboxylate;

(+)-(trans)-2-[2,5-difluoro-4-({[3-(phenyloxy)phenyl]
methyl}amino)phenyl]cyclopropanecarboxylic acid;

(+)-(trans)-2-{4-[({3-[(3,5-dichlorophenyl)oxy]
phenyl}methyl)amino]phenyl}cyclopropanecarboxylic acid;

(+)-(trans)-2-(4-{[(3-{[3-(trifluoromethyl)phenyl]
oxy}phenyl)methyl]amino}phenyl)cyclopropanecarboxylic acid;

(+)-(trans)-2{-4-[({3-[(4-methylphenyl)oxy]
phenyl}methyl)amino]phenyl}cyclopropanecarboxylic acid;

Racemic-(trans)-2-{4-[(4-biphenylmethyl)amino]
phenyl}cyclopropanecarboxamide;

Racemic-(trans)2-[4-({[4-(2-pyridinyl)phenyl]
methyl}amino)phenyl]cyclopropanecarboxamide;

Racemic-(trans)-2-{4-[({4-methyl-2-[4-(trifluoromethyl)
phenyl]-1,3-thiazol-5-yl}methyl)amino]phenyl}-N-(4-
pyridinylmethyl)cyclopropanecarboxamide;

Enantiomerically enriched (trans)-2-{4-[({4-methyl-2-[4-
(trifluoromethyl)phenyl]-1,3-thiazol-5-yl}methyl)amino]
phenyl}-N-(4-pyridinylmethyl)cyclopropanecarboxamide;

Enantiomerically enriched (trans)-2-{4-[({4-methyl-2-[4-
(trifluoromethyl)phenyl]-1,3-thiazol-5-yl}methyl)amino]
phenyl}cyclopropanecarboxamide;

Enantiomerically enriched (trans)2-{4-[({4-methyl-2-[4-
(trifluoromethyl)phenyl]-1,3-thiazol-5-yl}methyl)amino]
phenyl}-N-[(1S)-1-phenylethyl]cyclopropanecarboxamide;

Enantiomerically enriched (trans)-N-hydroxy-2-{4-[({4-methyl-2-[4-(trifluoromethyl)phenyl]-1,3-thiazol-5-
yl}methyl)amino]phenyl}cyclopropanecarboxamide;

Enantiomerically enriched (trans)-N-cyclobutyl-2-{4-[({4-
methyl-2-[4-(trifluoromethyl)phenyl]-1,3-thiazol-5-
yl}methyl)amino]phenyl}cyclopropanecarboxamide;

Racemic-(trans)-2-{4-[({4-methyl-2-[4-(trifluoromethyl)
phenyl]-1,3-thiazol-5-yl}methyl)amino]
phenyl}cyclopropanecarboxamide;

(+)-(trans)-N-(1-methylethyl)-2-[4-({[3-(phenyloxy)phenyl]methyl}amino)phenyl]cyclopropanecarboxamide;

Racemic-(trans)-N-isopropyl-2-{4-[({4-methyl-2-[4-(trifluoromethyl)phenyl]-1,3-thiazol-5-yl}methyl)amino]
phenyl}cyclopropanecarboxamide;

Racemic-(trans)-N,N-dimethyl-2-{4-[({4-methyl-2-[4-(trifluoromethyl)phenyl]-1,3-thiazol-5-yl}methyl)amino]
phenyl}cyclopropanecarboxamide;

Racemic-(trans)-2-[4-({[3-(phenyloxy)phenyl]
methyl}amino)phenyl]-N-(4-pyridinylmethyl)cyclopropanecarboxamide;

Racemic-(trans)-N-(4-methoxybenzyl)-2-{4-[(3-phenoxybenzyl)amino]phenyl}cyclopropanecarboxamide;

Racemic-(trans)-2-{4-[(3-phenoxybenzyl)amino]phenyl}N-
[4-(trifluoromethyl)benzyl]cyclopropanecarboxamide;

Racemic-(trans)-N-(2-morpholin-4-ylethyl)-2-{4-[(3-phenoxybenzyl)amino]phenyl}cyclopropanecarboxamide;

Racemic-(trans)-2-{4-[(3-phenoxybenzyl)amino]phenyl}-
N-(2,2,2-trifluoroethyl)cyclopropanecarboxamide;

Racemic-(trans)-N-isopropyl-2-{4-[({4-isopropyl-2-[4-(trifluoromethyl)phenyl]-1,3-thiazol-5-yl}methyl)amino]
phenyl}cyclopropanecarboxamide;

Enantiomerically enriched N-isopropyl-2-{4-[({4-methyl-2-
[4-(trifluoromethyl)phenyl]-1,3-thiazol-5-yl}methyl)
amino]phenyl}cyclopropanecarboxamide; and Enantiomerically enriched N-(cyclopropylmethyl)-2-{4-[(3-
phenoxybenzyl)amino]
phenyl}cyclopropanecarboxamide, including salts, solvates, and physiologically functional derivatives thereof.

Another aspect of the present invention includes the compounds of the present invention substantially as hereinbefore defined with reference to any one of the Examples.

Another aspect of the present invention includes pharmaceutical compositions that include the compounds of the present invention, preferably with a pharmaceutically acceptable carrier.

Another aspect of the present invention includes the compounds of the present invention for use as an active therapeutic substance.

Another aspect of the present invention includes the compounds of the present invention for use in the treatment or prophylaxis of conditions or disorders affected by GPR40. Preferably the condition or disorder is one or more of diabetes, obesity, glucose intolerance, insulin resistance, metabolic syndrome X, hyperlipidemia, hypercholesterolemia, atherosclerosis, neurodegenerative diseases, and cerebrovascular conditions.

Another aspect of the present invention includes the use of one or more compound of the present invention in the manufacture of a medicament for use in the treatment or prophylaxis of conditions or disorders affected by GPR40. Preferably the condition or disorder is one or more of diabetes, obesity, glucose intolerance, insulin resistance, metabolic syndrome X, hyperlipidemia, hypercholesterolemia, atherosclerosis, neurodegenerative diseases, and cerebrovascular conditions.

Another aspect of the present invention includes methods for the treatment or prophylaxis of conditions or disorders affected by GPR40 comprising the administration of one or more of the compounds of the present invention. Preferably the condition or disorder is one or more of diabetes, obesity, glucose intolerance, insulin resistance, metabolic syndrome X, hyperlipidemia, hypercholesterolemia, atherosclerosis, neurodegenerative diseases, and cerebrovascular conditions.

Another aspect of the present invention includes synthetic processes for preparing the compounds of the present invention. One aspect of the present invention includes a process for the preparation of enantiomerically enriched-(trans)-ethyl-2-(4-amino-aryl)-cyclopropanecarboxylates that includes mixing a nitrobenzene compound, a palladium compound, and a tin compound in an appropriate solvent with heating to prepare a styrene product; dissolving said styrene product in an appropriate solvent and adding a mixture of a copper (I) trifluoromethanesulfonate-toluene complex and (2R)-4-tert-Butyl-2-{1-[(4R)-4-tert-butyl-4,5-dihydro-1,3-oxazol-2-yl]-1-methylethyl}-4,5-dihydro-1,3-oxazole and ethyldiazoacetate; and purifying to give enantiomerically enriched cyclopropanecarboxylates.

Particularly preferred intermediates include intermediates of formula IIId and IIIe:

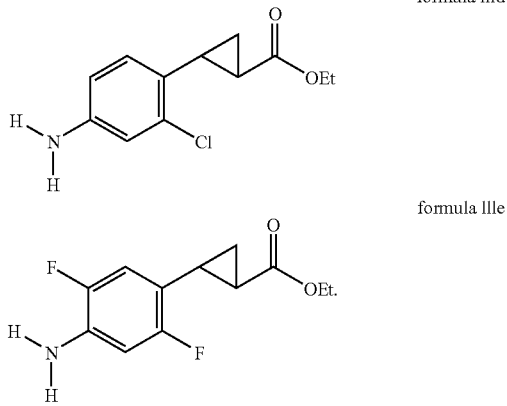

formula IIId formula IIIe

DETAILED DESCRIPTION OF THE PREFERRED EMBODIMENT

The present invention is described in terms known and appreciated by those skilled in the art. For ease of reference certain terms hereinafter are defined. The fact that certain terms are defined, however, should not be considered as indicative that defined terms are used in a manner necessarily inconsistent with the ordinary meaning or, alternatively, that any term that is undefined is indefinite or not used within the ordinary and accepted meaning. Rather, all terms used herein are believed to describe the invention such that one of ordinary skill can appreciate the scope of the present invention.

As used herein the term "alkyl" refers to a straight or branched chain hydrocarbon, preferably having from one to twelve carbon atoms. Examples of "alkyl" as used herein include, but are not limited to, methyl, ethyl, propyl, isopropyl, isobutyl, n-butyl, tert-butyl, isopentyl, n-pentyl.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well.

As used herein, the term "alkylene" refers to a straight or branched chain divalent hydrocarbon radical, preferably having from one to ten carbon atoms. Examples of "alkylene" as used herein include, but are not limited to, methylene, ethylene, n-propylene, n-butylene, and the like, as well as substituted versions thereof.

As used herein, the term "cycloalkyl" refers to an optionally substituted non-aromatic cyclic hydrocarbon ring. Exemplary "cycloalkyl" groups include, but are not limited to, cyclopropyl, cyclobutyl, cyclopentyl, cyclohexyl, cycloheptyl, and substituted versions thereof. As used herein, the term "cycloalkyl" includes a fused polycyclic hydrocarbon saturated ring and aromatic ring system, namely polycyclic hydrocarbons with less than maximum number of non-cumulative double bonds, for example where a saturated hydrocarbon ring (such as a cyclopentyl ring) is fused with an aromatic ring (herein "aryl," such as a benzene ring) to form, for example, groups such as indane.

As used herein, the term "heterocycle" or "heterocyclyl" refers to a mono- or polycyclic ring system containing one or more degrees of unsaturation and also containing one or more heteroatoms. Preferred heteroatoms include N, O, and/or S, including N-oxides, sulfur oxides, and dioxides. Preferably the ring is three to twelve-membered and is either fully saturated or has one or more degrees of unsaturation. Such rings may be optionally fused to one or more of another "heterocyclic" ring(s) or cycloalkyl ring(s). Examples of "heterocyclic" groups include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein, the term "aryl" refers to an aromatic ring or ring system, such as a benzene ring or a fused benzene ring system, for example an anthracene, a phenanthrene, or a naphthalene ring system. Examples of "aryl" groups include, but are not limited to, phenyl, 2-naphthyl, 1-naphthyl, and substituted derivatives thereof.

As used herein, the term "heteroaryl" refers to a monocyclic five to seven membered aromatic ring, or to a fused bicyclic aromatic ring system comprising two of such aromatic rings where the ring or ring system contains one or more nitrogen, sulfur, and/or oxygen atoms. N-oxides, sulfur oxides, and dioxides are permissible heteroatom substitutions. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, benzimidizolyl, imidazopyridinyl, pyrazolopyridinyl, pyrazolopyrimidinyl, and substituted versions thereof.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, and iodo. The term "haloalkyl" should be interpreted to include such substituents as perfluoroalkyl groups and the like.

As used herein the term "hydroxy" refers to the group —OH.

As used herein the term "alkoxy" refers to the group —OR$^a$, where R$^a$ is alkyl as defined above.

As used herein the term "aryloxy" refers to the group —OR$^a$, where R$^a$ is aryl or heteroaryl as defined above.

As used herein the term "nitro" refers to the group —NO$_2$.

As used herein the term "cyano" refers to the group —CN.

As used herein throughout the present specification, the phrase "optionally substituted" or variations thereof denote an optional substitution, including multiple degrees of substitution, with one or more substituent group. The phrase should not be interpreted so as to be imprecise or duplicative of substitution patterns herein described or depicted specifically. Rather, those of ordinary skill in the art will appreciate that the phrase is included to provide for obvious modifications, which are encompassed within the scope of the appended claims.

The compounds of formulas (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may include acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of Burger's *Medicinal Chemistry And Drug Discovery*, 5th Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as salts, solvates, and physiological functional derivatives thereof, may be administered as the raw chemical. Additionally, the active ingredient may be presented as a pharmaceutical composition.

Accordingly, the invention further provides pharmaceutical compositions that include effective amounts of compounds of the formula (I) and salts, solvates, and physiological functional derivatives thereof, and one or more pharmaceutically acceptable carriers, diluents, or excipients. The compounds of formula (I) and salts, solvates, and physiologically functional derivatives thereof, are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of formula (I) for the treatment of humans suffering from diabetes and associated conditions, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment of the other conditions referred to herein.

Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful, certain routes will be preferable over others. For example, oral administration is preferred for many diabetic therapy regimens.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and then encapsulating such with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle.

Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and salts, solvates, and physiologically functional derivatives thereof may also be delivered by the use of monoclonal antibodies as individual carriers to which the compound molecules are coupled.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention and their salts, solvates, and physiologically functional derivatives thereof, may be employed alone or in combination with other therapeutic agents. The compound(s) of formula (I) and the other pharmaceutically active agent(s) may be administered together or separately and, when administered separately, administration may occur simultaneously or sequentially, in any order. The amounts of the compound(s) of formula (I) and the other pharmaceutically active agent(s) and the relative timings of administration will be selected in order to achieve the desired combined therapeutic effect. The administration in combination of a compound of formula (I) salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of the present invention may be used in the treatment of a variety of disorders and conditions. As such, the compounds of the present invention may be used in combination with a variety of other therapeutic agents useful in the treatment or prophylaxis of those disorders or conditions. As discussed briefly above, current diabetes therapies include diet, exercise, insulin, insulin secretagogues, glucose-lowering effectors, PPAR-$\gamma$ agonists, and $\alpha$-glucosidase inhibitors. The compounds of the present invention may be combined with these or other medical therapies to treat and/or prevent diabetes and associated disorders and conditions, including but not limited to diabetes types I and II, obesity, glucose intolerance, insulin resistance, metabolic syndrome X, hyperlipidemia, hypercholesterolemia, artheroscelrosis, neurodegenerative diseases, and other indications such as stroke.

The compounds of this invention may be made by a variety of methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

EXPERIMENTAL SECTION

The symbols, abbreviations, and conventions used in the processes, schemes, and examples are consistent with those used in the contemporary scientific literature, for example, the *Journal of the American Chemical Society or the Journal of Biological Chemistry*. Specifically, but not meant as limiting, the following abbreviations may be used in the examples and throughout the specification:

g (grams); mg (milligrams);
L (liters); mL (milliliters);
$\mu$L (microliters); psi (pounds per square inch);
atm (atmosphere); mp (melting point);
M (molar); mM (millimolar);
Hz (Hertz); MHz (megahertz);
mol (moles); mmol (millimoles);
RT (room temperature); h (hours);
min (minutes); TLC (thin layer chromatography);
$T_r$ (retention time); RP (reverse phase);

MeOH (methanol); EtOH (ethanol);
CHCl₃ (chloroform); CDCl₃ (deuterated chloroform);
DMSO (dimethylsulfoxide); SiO₂ (silica);
EtOAc (ethyl acetate); HCl (hydrochloric acid);
Ac (acetyl); DMF (N,N-dimethylformamide);
tBu (tert-butyl).

Unless otherwise indicated, all temperatures are expressed in ° C. (degrees Centigrade). All reactions conducted at room temperature unless otherwise noted.

¹H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad).

Mass spectra were obtained on Micromass Platform or ZMD mass spectrometers from Micromass Ltd., Altricham, UK, using either Atmospheric Chemical Ionization (APCI) or Electrospray Ionization (ESI).

Analytical thin layer chromatography was used to verify the purity of intermediate(s) which could not be isolated or which were too unstable for full characterization as well as to follow the progress of reaction(s).

Determination of enantiomeric excess (% ee):

Method 1:

All samples were run on a Berger analytical SFC system with an HP1100 diode array detector. The samples were monitored at 230 nm (with the exception of Example 31a, which was monitored at 254 nm) under the following conditions: 30% MeOH in CO2, 2250 psi, 50 C, 2 mL/minute on a Diacel Chiralcel OJ-H column, 4.6×250 mm, 5μ.

Method 2:

All samples were run on a Berger analytical SFC system with an HP1100 diode array detector. The samples were monitored at 254 nm under the following conditions: 30% MeOH in CO2, 3000 psi, 40 C, 2 mL/minute on a Diacel Chiralcel OD-H column, 4.6×250 mm, 5μ.

Method 3:

The sample was run on a Berger analytical SFC system with an HP1100 diode array detector. The sample was monitored at 254 nm under the following conditions: 10% MeOH in CO2, 3000 psi, 40 C, 2 mL/minute on a Diacel Chiralcel OJ-H column, 4.6×250 mm, 5μ.

EXAMPLES

Example 1

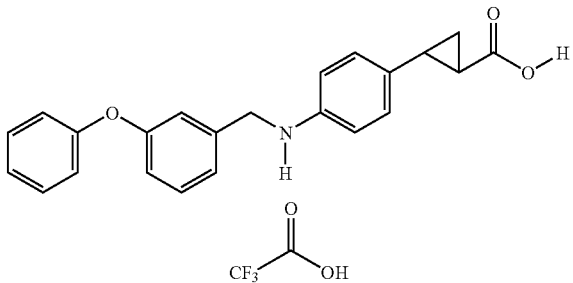

Racemic-(trans)-2-[4-({[3-(phenyloxy)phenyl]methyl}ammonium)phenyl]cyclopropanecarboxylic Acid Trifluoroacetate (I-2a)

A suspension of racemic-(trans)-2-(4-aminophenyl)cyclopropanecarboxylic acid (I-1) (0.50 g, 2.82 mmol) and 3-(phenyloxy)benzaldehyde (0.58 g, 2.93 mmol) in dichloroethane (20 mL) were heated to reflux until a clear solution formed. The solution was cooled to RT then NaB(OAc)₃H (1.00 g, 4.72 mmol) was added and stirred for 1 h. Water (100 mL) and dichloromethane (100 mL) were added and the organic layer was separated, dried over Na₂SO₄, filtered and concentrated. The crude material was purified on silica gel eluting with an increasing gradient from hexanes to 50% ethyl acetate/hexanes to give the title compound as a gummy solid (0.16 g, 16%). ¹H NMR (400 MHz, CDCl₃) δ 7.35-7.26 (m, 3H), 7.12-7.08 (m, 2H), 7.02-6.98 (m, 3H), 6.94-6.89 (m, 3H), 6.54 (d, J=8.5 Hz, 2H), 4.29 (s, 2H), 2.55-2.50 (m, 1H), 1.80-1.76 (m, 1H), 1.61-1.56 (m, 1H), 1.35-1.31 (m, 1H). ES-MS m/z 358.4 (MH−). Compound was converted to the trifluoroacetic acid salt.

Example 2

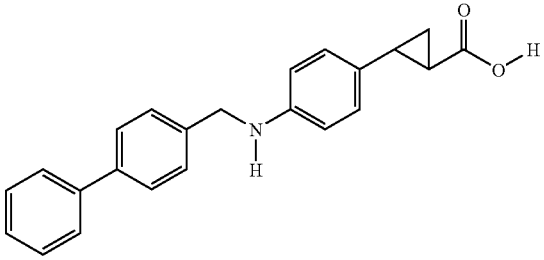

Scheme I:

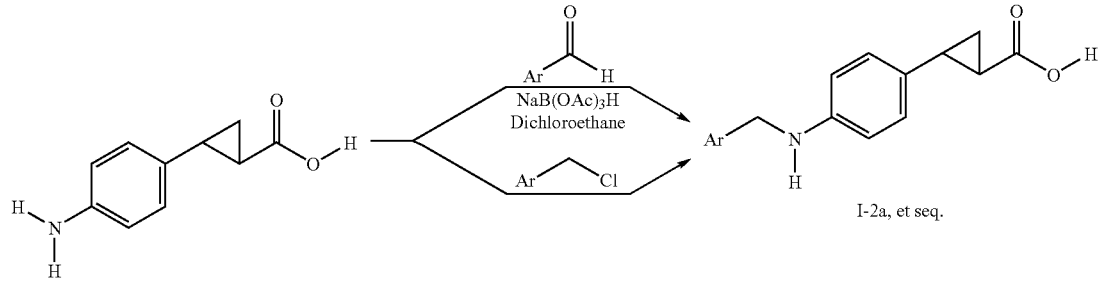

General synthesis of racemic-(trans)-cyclopropanecarboxylic acid derivaties

Racemic-(trans)-2-{4-[(4-biphenylylmethyl)amino]phenyl}cyclopropanecarboxylic Acid (I-2b)

A suspension of racemic-(trans)-2-(4-aminophenyl)cyclopropanecarboxylic acid (I-1) (0.28 g, 1.58 mmol) and 4-biphenylcarbaldehyde (0.32 g, 1.74 mmol) in dichloroethane (20 mL) were heated to reflux until a clear solution formed. The solution was cooled to RT then NaB(OAc)$_3$H (0.50 g, 2.37 mmol) was added and stirred for 2 h. Water (50 mL) and dichloromethane (50 mL) were added and the organic layer was separated, dried over Na$_2$SO$_4$, filtered and concentrated. The crude material was purified on silica gel eluting with an increasing gradient from hexanes to 40% ethyl acetate/hexanes to give the title compound as a white solid (0.33 g, 61%). $^1$H NMR (400 MHz, DMSO) δ 12.15 (s, 1H), 7.65-7.59 (m, 4H), 7.46-7.41 (m, 4H), 7.34 (t, J=7.3 Hz, 1H), 6.84 (d, J=8.6 Hz, 2H), 6.51 (d, J=8.4 Hz, 2H), 6.22 (s, 1H), 4.29 (s, 2H), 2.23-2.18 (m, 1H), 1.62-1.57 (m, 1H), 1.32-1.28 (m, 1H), 1.21-1.16 (m, 1H). ES-MS m/z 344.2 (MH+).

Example 3

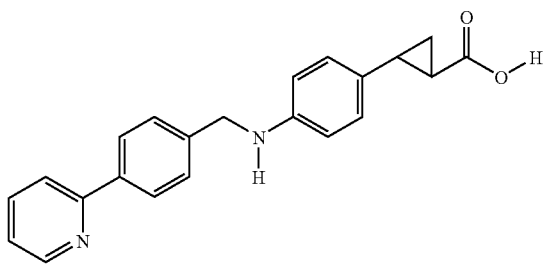

Racemic-(trans)-2-[4-({[4-(2-pyridinyl)phenyl]methyl}amino)phenyl]cyclopropanecarboxylic Acid (I-2c)

A suspension of racemic-(trans)-2-(4-aminophenyl)cyclopropanecarboxylic acid (I-1) (0.30 g, 1.69 mmol) and 4-(2-pyridinyl)benzaldehyde (0.37 g, 2.03 mmol) in dichloroethane (10 mL) were heated to reflux until a clear solution formed. The solution was cooled to RT then NaB(OAc)$_3$H (0.54 g, 2.54 mmol) was added and stirred for 2 h. Water (50 mL) and dichloromethane (50 mL) were added and the organic layer was separated, dried over Na$_2$SO$_4$, filtered and concentrated. The crude material was purified on silica gel eluting with an increasing gradient from 20% ethyl acetate/hexanes to 100% ethyl acetate to give the title compound as a white solid (0.13 g, 22%). $^1$H NMR (400 MHz, DMSO) δ 12.15 (s, 1H), 8.65 (d, J=4.1 Hz, 1H), 8.02 (d, J=8.3 Hz, 2H), 7.92 (d, J=8.2 Hz, 1H), 7.86 (t, J=8.0 Hz, 1H), 7.44 (d, J=8.1 Hz, 2H), 7.32 (dd, J=5.2, 6.6 Hz, 1H), 6.84 (d, J=8.4 Hz, 2H), 6.50 (d, J=8.4 Hz, 2H), 6.23 (s, 1H), 4.30 (d, J=4.6 Hz, 2H), 2.22-2.17 (m, 1H), 1.61-1.57 (m, 1H), 1.31-1.27 (m, 1H), 1.20-1.16 (m, 1H).

Example 4

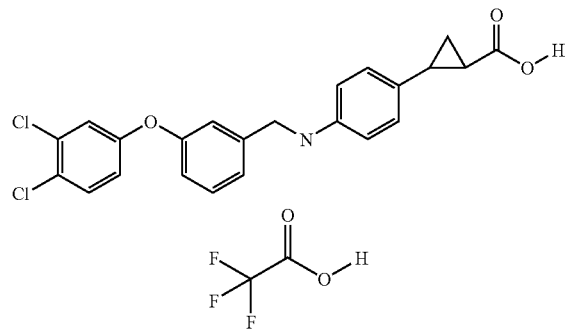

Racemic-(trans)-2-{4-[({3-[(3,4-dichlorophenyl)oxy]phenyl}methyl)ammonium]phenyl}-cyclopropanecarboxylic Acid Trifluoroacetate (I-2d)

To a mixture of racemic-(trans)-2-(4-aminophenyl)cyclopropanecarboxylic acid (I-1) (0.064 g, 0.361 mmol) in dichloroethane (2 mL) was added 3-(3,4-dichlorophenoxy)benzaldehyde (0.089 g, 0.333 mmol). The mixture was stirred for 5 h followed by addition of sodium triacetoxyborohydride (0.101 g, 0.476 mmol). The mixture was stirred for 12 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by preparative HPLC (10% to 100% CH$_3$CN/H$_2$O with 0.05% TFA) to give the title compound as a white solid (0.059 g, 32%). $^1$H NMR (400 MHz, DMSO-de) 87.56 (d, J=8.8 Hz, 1H), 7.34 (t, J=7.9 Hz, 1H), 7.19-7.15 (m, 2H), 7.02 (s, 1H), 6.92 (dd, J=8.7 Hz, J=3.0 Hz, 2H), 6.82 (d, J=8.1 Hz, 2H), 6.46 (d, J=8.1 Hz, 2H), 4.24 (s, 2H), 2.18 (m, 1H), 1.57 (m, 1H), 1.27 (m, 1H), 1.16 (m, 1H). ES-MS m/z 428 (MH+).

Example 5

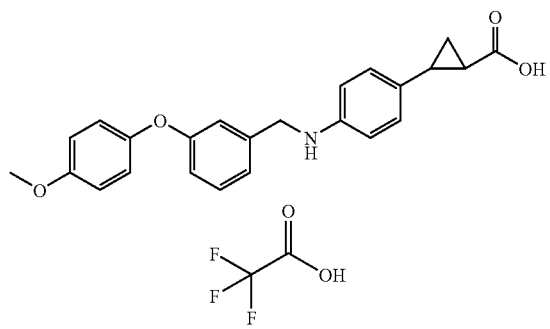

Racemic-(trans)-2-(4-{[(3-{[4-(methyloxy)phenyl]oxy}phenyl)methyl]ammonium}phenyl)-cyclopropanecarboxylic Acid Trifluoroacetate (I-2e)

To a mixture of racemic-(trans)-2-(4-aminophenyl)cyclopropanecarboxylic acid (I-1) (0.063 g, 0.355 mmol) in dichloroethane (2 mL) was added 3-(4-methoxyphenoxy)benzaldehyde (0.070 mL, 0.334 mmol). The mixture was stirred for 5 h followed by addition of sodium triacetoxyborohydride (0.116 g, 0.547 mmol). The mixture was stirred for 12 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by preparative HPLC (10% to 100% CH$_3$CN/H$_2$O with 0.05% TFA) to give the title compound as a white solid (0.052 g, 31%). $^1$H NMR (400 MHz, DMSO-d$_6$) δ7.24 (t, J=7.8 Hz, 1H), 7.02 (d, J=7.5 Hz, 1H), 6.91-6.89 (m, 5H), 6.83 (d, J=8.2 Hz, 2H), 6.72 (dd, J=8.1 Hz, 2.2 Hz, 1H), 6.47 (d, J=8.1 Hz, 2H), 4.20 (s, 2H), 3.72 (s, 3H), 2.19 (m, 1H), 1.59 (m, 1H), 1.28 (m, 1H), 1.17 (m, 1H). ES-MS m/z 390 (MH+).

Example 6

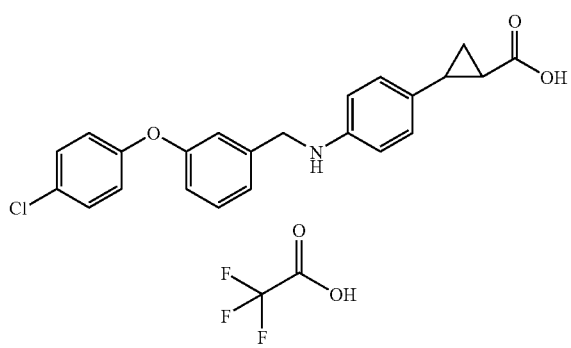

Racemic-(trans)-2-{4-[({3-[(4-chlorophenyl)oxy] phenyl}methyl)ammonium]phenyl}-cyclopropanecarboxylic Acid Trifluoroacetate (I-2f)

To a mixture of racemic-(trans)-2-(4-aminophenyl)cyclopropanecarboxylic acid (I-1) (0.063 g, 0.355 mmol) in dichloroethane (2 mL) was added 3-(4-chlorophenoxy)benzaldehyde (0.065 mL, 0.339 mmol). The mixture was stirred for 5 h followed by addition of sodium triacetoxyborohydride (0.111 g, 0.524 mmol). The mixture was stirred for 12 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by preparative HPLC (10% to 100% CH$_3$CN/H$_2$O with 0.05% TFA) to yield the title compound as a white solid (0.029 g, 17%). $^1$H NMR (400 MHz, DMSO-de) δ7.37 (d, J=8.8 Hz, 2H), 7.31 (t, J=7.8 Hz, 1H), 7.12 (d, J=7.7 Hz, 1H), 6.97-6.93 (m, 3H), 6.85-6.81 (m, 3H), 6.46 (d, J=7.8 Hz, 2H), 4.22 (s, 2H), 2.19 (m, 1H), 1.58 (m, 1H), 1.28 (m, 1H), 1.17 (m, 1H). ES-MS m/z 394 (MH+).

Example 7

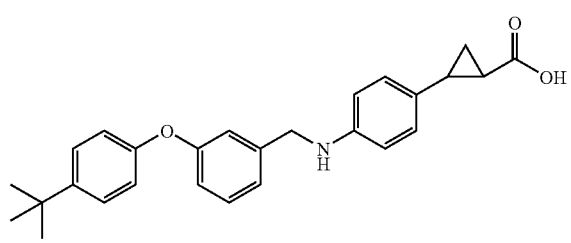

-continued

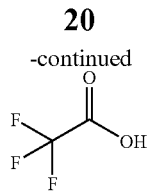

Racemic-(trans)-2-(4-{[(3-{[4-(1,1-dimethylethyl) phenyl]oxy}phenyl)methyl]ammonium}phenyl)cyclopropanecarboxylic Acid Trifluoroacetate (I-2g)

To a mixture of racemic-(trans)-2-(4-aminophenyl)cyclopropanecarboxylic acid (I-1) (0.063 g, 0.355 mmol) in dichloroethane (2 mL) was added 3-(4-t-butylphenoxy)benzaldehyde (0.085 mL, 0.329 mmol). The mixture was stirred for 5 h followed by addition of sodium triacetoxyborohydride (0.104 g, 0.491 mmol). The mixture was stirred for 12 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by preparative HPLC (10% to 100% CH$_3$CN/H$_2$O with 0.05% TFA) to give the title compound as a white solid (0.063 g, 36%). $^1$H NMR (400 MHz, DMSO-d$_6$) δ7.32 (d, J=8.6 Hz, 2H), 7.27 (t, J=7.9 Hz, 1H), 7.06 (d, J=7.5 Hz, 1H), 6.95 (s, 1H), 6.85-6.76 (m, 5H), 6.44 (d, J=8.1 Hz, 2H), 4.21 (s, 2H), 2.18 (m, 1H), 1.58 (m, 1H), 1.24 (m+s, 10H), 1.17 (m, 1H). ES-MS m/z 414 (MH−).

Example 8

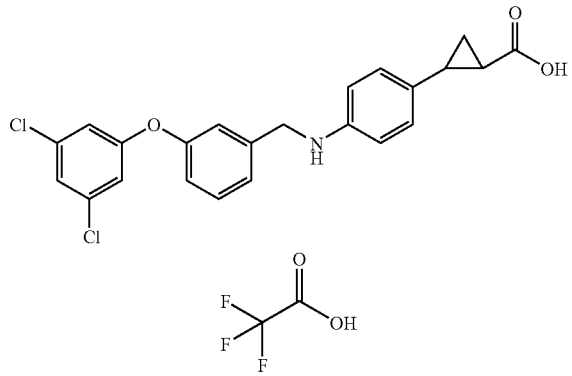

Racemic-(trans)-2-{4-[({3-[(3,5-dichlorophenyl) oxy]phenyl}methyl)ammonium]phenyl}-cyclopropanecarboxylic Acid Trifluoroacetate (I-2h)

To a mixture of racemic-(trans)-2-(4-aminophenyl)cyclopropanecarboxylic acid (I-1) (0.064 g, 0.359 mmol) in dichloroethane (2.5 mL) was added 3-(3,5-dichlorophenoxy)benzaldehyde (0.086 g, 0.324 mmol). The mixture was stirred for 12 h followed by addition of sodium triacetoxyborohydride (0.107 g, 0.505 mmol). The mixture was stirred for 7 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by preparative HPLC (10% to 100% CH$_3$CN/H$_2$O with 0.05% TFA) to give the title compound as a white solid (0.108 g, 61%). $^1$H NMR (400 MHz, DMSO-d$_6$) δ 7.36 (t, J=7.8 Hz, 1H), 7.31 (s, 1H), 7.20

(d, J=7.7 Hz, 1H), 7.05 (s, 1H), 6.95-6.93 (m, 3H), 6.81 (d, J=8.2 Hz, 2H), 6.45 (d, J=8.2 Hz, 2H), 4.24 (s, 2H), 2.17 (m, 1H), 1.56 (m, 1H), 1.27 (m, 1H), 1.15 (m, 1H). APCI-MS m/z 428 (MH+).

Example 9

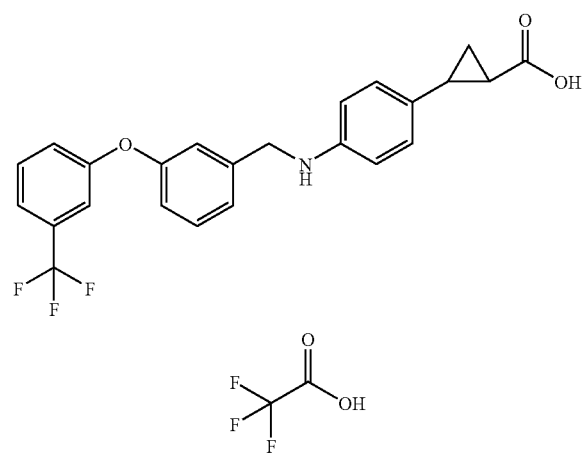

Racemic-(trans)-2-(4-{[(3-{[3-(trifluoromethyl)phenyl]oxy}phenyl)methyl]ammonium}-phenyl)cyclopropanecarboxylic Acid Trifluoroacetate (I-2l)

To a mixture of racemic-(trans)-2-(4-aminophenyl)cyclopropanecarboxylic acid (I-1) (0.062 g, 0.349 mmol) in dichloroethane (2.5 mL) was added 3-(3-trifluoromethylphenoxy)benzaldehyde (0.060 mL, 0.347 mmol). The mixture was stirred for 12 h followed by addition of sodium triacetoxyborohydride (0.113 g, 0.533 mmol). The mixture was stirred for 7 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by preparative HPLC (10% to 100% CH$_3$CN/H$_2$O with 0.05% TFA) to give the title compound as a white solid (0.033 g, 17%). $^1$H NMR (400 MHz, DMSO-d$_6$) δ 7.56 (t, J=8.0 Hz, 1H), 7.44 (d, J=7.7 Hz, 1H), 7.35 (t, J=7.9 Hz, 1H), 7.22-7.16 (m, 3H), 7.04 (s, 1H), 6.91 (d, J=8.1 Hz, 1H), 6.81 (d, J=8.2 Hz, 2H), 6.46 (d, J=8.1 Hz, 2H), 4.24 (s, 2H), 2.18 (m, 1H), 1.57 (m, 1H), 1.27 (m, 1H), 1.16 (m, 1H). APCI-MS m/z 428 (MH+).

Example 10

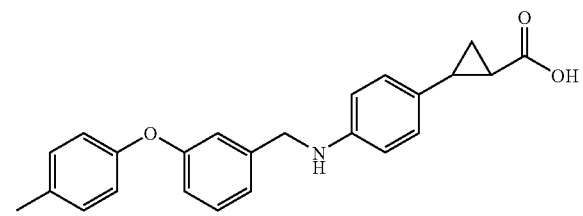

-continued

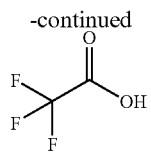

Racemic-(trans)-2-{4-[({3-[(4-methylphenyl)oxy]phenyl}methyl)ammonium]phenyl}-cyclopropanecarboxylic Acid Trifluoroacetate (I-2j)

To a mixture of racemic-(trans)-2-(4-aminophenyl)cyclopropanecarboxylic acid (I-1) (0.061 g, 0.342 mmol) in dichloroethane (2.5 mL) was added 3-(4-methylphenoxy)benzaldehyde (0.060 mL, 0.311 mmol). The mixture was stirred for 12 h followed by addition of sodium triacetoxyborohydride (0.107 g, 0.505 mmol). The mixture was stirred for 7 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by preparative HPLC (10% to 100% CH$_3$CN/H$_2$O with 0.05% TFA) to give the title compound as a white solid (0.039 g, 26%). $^1$H NMR (400 MHz, DMSO-de) 87.26 (t, J=7.9 Hz, 1H), 7.13 (d, J=8.2 Hz, 2H), 7.02 (d, J=7.5 Hz, 1H), 6.92 (s, 1H), 6.83 (d, J=8.1 Hz, 4H), 6.76 (d, J=8.1 Hz, 1H), 6.47 (d, J=7.9 Hz, 2H), 4.20 (s, 2H), 2.25 (s, 3H), 2.19 (m, 1H), 1.58 (m, 1H), 1.28 (m, 1H), 1.17 (m, 1H). APCI-MS m/z 374 (MH+).

Example 11

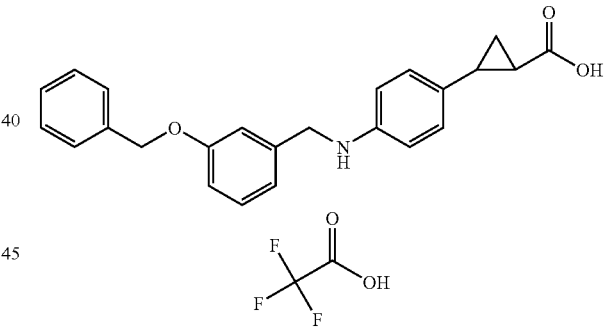

Racemic-(trans)-2-{4-[({3-[(phenylmethyl)oxy]phenyl}methyl)ammonium]phenyl}-cyclopropanecarboxylic Acid Trifluoroacetate (I-2k)

To a mixture of racemic-(trans)-2-(4-aminophenyl)cyclopropanecarboxylic acid (I-1) (0.066 g, 0.372 mmol) in dichloroethane (1.0 mL) was added 3-[(phenylmethyl)oxy]benzaldehyde (0.072 g, 0.339 mmol). The mixture was stirred for 12 h followed by addition of sodium triacetoxyborohydride (0.119 g, 0.561 mmol). The mixture was stirred for 7 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by preparative HPLC (10% to 100% CH$_3$CN/H$_2$O with 0.05% TFA) to give the title compound as an orange solid (0.06 g, 36%). $^1$H NMR (400 MHz, DMSO-d$_6$) δ 7.41-7.30 (m, 5H), 7.20 (t, J=7.9 Hz, 1H), 6.99 (s, 1H), 6.90 (d, J=7.5 Hz, 1H), 6.86 (m, 3H), 6.55 (d, J=7.5, 2H), 5.04 (s, 2H), 4.21 (s, 2H), 2.20 (m, 1H), 1.60 (m, 1H), 1.29 (m, 1H), 1.17 (m, 1H). ES-MS m/z 374 (MH+).

Example 12

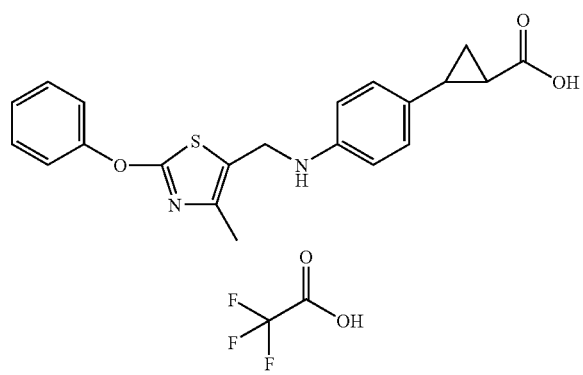

Racemic-(trans)-2-[4-({[4-methyl-2-(phenyloxy)-1,3-thiazol-5-yl]methyl}ammonium)-phenyl]cyclopropanecarboxylic Acid Trifluoroacetate (I-21)

To a mixture of racemic-(trans)-2-(4-aminophenyl)cyclopropanecarboxylic acid (I-1) (0.076 g, 0.429 mmol) in dichloroethane (2.0 mL) was added 4-methyl-2-(phenyloxy)-1,3-thiazole-5-carbaldehyde (X-4a) (0.086 g, 0.392 mmol). The mixture was stirred for 7 h followed by addition of sodium triacetoxyborohydride (0.127 g, 0.599 mmol). The mixture was stirred for 2 days at RT. Water was added (10 mL) and the layers were separated. The aqueous phase was extracted with CH$_2$Cl$_2$ (2×10 mL). The combined organics were dried with MgSO$_4$ and concentrated. The crude material was purified by preparative HPLC (10% to 100% CH$_3$CN/H$_2$O with 0.05% TFA) to give the title compound as a yellow solid (0.062 g, 32%). $^1$H NMR (400 MHz, DMSO-d$_6$) δ 7.45-7.41 (m, 2H), 7.29-7.24 (m, 3H), 6.87 (d, J=8.4 Hz, 2H), 6.51 (d, J=8.4 Hz, 2H), 4.23 (s, 2H), 2.20 (m, 1H), 2.17 (s, 3H), 1.60 (m, 1H), 1.29 (m, 1H), 1.17 (m, 1H). ES-MS m/z 381 (MH+).

Example 13

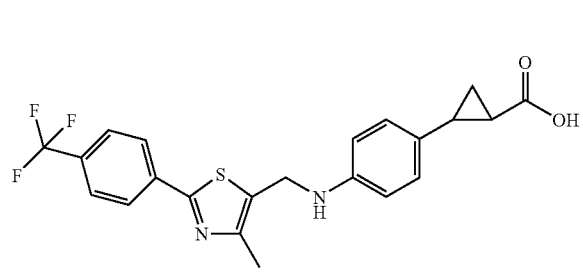

Racemic-(trans)-2-{4-[({4-methyl-2-[4-(trifluoromethyl)phenyl]-1,3-thiazol-5-yl}methyl)amino]phenyl}cyclopropanecarboxylic Acid (I-2m)

Experimental procedure analogous to that describing the synthesis of I-2a-I except that 4-methyl-2-(4-trifluoromethylphenyl)-1,3-thiazole-5-carbaldehyde and racemic-(trans)- 2-(4-aminophenyl)cyclopropanecarboxylic acid (I-1) were used to give 1.05 g of the title compound as a light yellow solid. $^1$H NMR (400 MHz, CDCl$_3$) δ 7.98 (d, J=8.78 Hz, 2H), 7.65 (d, J=8.78 Hz, 2H), 6.97 (d, J=8.60 Hz, 2H), 6.60 (d, J=8.60 Hz, 2H), 4.46 (s, 2H), 2.53 (m, 1H), 2.50 (s, 3H), 1.80 (m, 1H), 1.60 (m, 1H), 1.36 (m, 1H). ES-MS m/z 360 (MH+).

Example 14

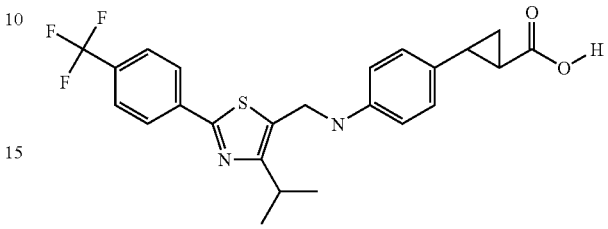

Racemic-(trans)-2-{4-[({4-isopropyl-2-[4-(trifluoromethyl)phenyl]-1,3-thiazol-5-yl}methyl)amino]phenyl}cyclopropanecarboxylic Acid (I-2n)

To a solution of {(4-isopropyl-2-[4-(trifluoromethyl)phenyl]-1,3-thiazol-5-yl}methanol (0.10 g, 0.331 mmol) in dichloromethane (3 mL) was added Et$_3$N (0.04 g, 0.39 mmol) and the mixture cooled to 0° C. The mixture stirred for 15 min after which methanesulfonyl chloride (0.04 g, 0.36 mmol) was added followed 30 min later by the addition of racemic-(trans)-2-(4-aminophenyl)cyclopropanecarboxylic acid (I-1) (0.09 g, 0.49 mmol). The solution stirred for 24 h after which it was poured into H$_2$O, the organics extracted with dichloromethane, dried over MgSO$_4$, and the solvents reduced in vacuo. The crude material was purified on silica gel eluting with an increasing gradient from hexanes to 30% ethyl acetate/hexanes to give the title compound as a yellow powder (0.03 g, 16%). $^1$H NMR (400 MHz, CDCl$_3$) δ 8.01 (d, J=8.3 Hz, 2H), 7.65 (d, J=8.2 Hz, 2H), 6.98 (d, J=8.4 Hz, 2H), 6.62 (d, J=8.6 Hz, 2H), 4.47 (s, 2H), 3.50-3.47 (m, 1H), 3.18-3.15 (m, 1H), 2.53-2.51 (m, 1H), 1.80-1.77 (m, 1H), 1.61-1.58 (m, 1H), 1.37-1.26 (m, 7H).

Example 15

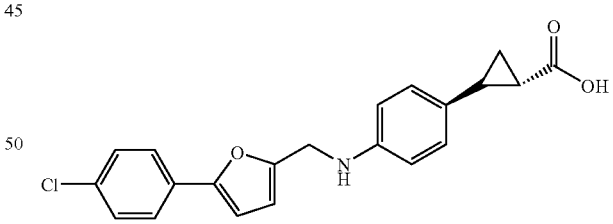

Racemic-(trans)-2-[4-({[5-(4-chlorophenyl)-2-furanyl]methyl}amino)phenyl]cyclopropanecarboxylic Acid (I-2o)

To a mixture of (of racemic-(trans)-2-(4-aminophenyl)cyclopropanecarboxylic acid (I-1) (0.057 g, 0.322 mmol) in dichloroethane (2.5 mL) was added 5-(2-chlorophenyl)furfural (0.059 g, 0.285 mmol). The mixture was stirred for 2 days followed by addition of sodium triacetoxyborohydride (0.097 g, 0.458 mmol). The mixture was stirred for 7 h at RT. Water was added (10 mL), and the layers were separated. The aqueous phase was extracted with CH$_2$Cl$_2$ (2×10 mL). The combined organics were dried with MgSO₄ and concentrated. The crude material was purified by chromatography (EtOAc/hexanes) to give the title compound as a yellow solid (0.06 g, 60%). ¹H NMR (400 MHz, DMSO-d₆): δ 12.13 (s, 1H), 7.64 (d, J=8.6 Hz, 2H), 7.43 (d, J=8.6 Hz, 2H), 6.87 (d, J=3.3 Hz, 1H), 6.85 (d, J=8.4 Hz, 2H), 6.57 (d, J=8.4 Hz, 2H), 6.36 (d, J=3.3 Hz, 1H), 6.03 (t, J=6.0 Hz, 1H), 4.25 (d, J=6.0 Hz, 2H), 2.19 (m, 1H), 1.58 (m, 1H), 1.28 (m, 1H), 1.17 (m, 1H). ES-MS m/z 366.13 (MH−).

Example 16

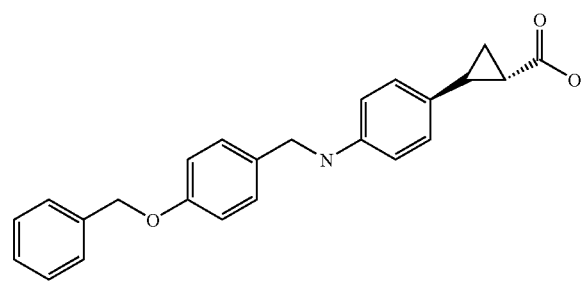

Racemic-(trans)-2-{4-[({4-[(phenylmethyl)oxy]phenyl}methyl)amino]phenyl}cyclopropanecarboxylic Acid trifluoroacetate (I-2p)

To a mixture of racemic-(trans)-2-(4-aminophenyl)cyclopropanecarboxylic acid (I-1) (0.053 g, 0.299 mmol) in dichloroethane (2.5 mL) was added 4-benzyloxybenzaldehyde (0.058 g, 0.273 mmol). The mixture was stirred for 12 h followed by addition of sodium triacetoxyborohydride (0.082 g, 0.387 mmol). The mixture was stirred for 7 h at RT. Water was added (10 mL), and the layers were separated. The aqueous phase was extracted with CH₂Cl₂ (2×10 mL). The combined organics were dried with MgSO₄ and concentrated. The crude material was purified by preparative HPLC (10% to 100% CH₃CN/H₂O with 0.05% TFA) to give the title compound as a yellow solid (0.008 g, 6%). ¹H NMR (400 MHz, DMSO-de): δ 7.42-7.30 (m, 5H), 7.24 (d, J=8.4 Hz, 2H), 6.93 (d, J=8.6 Hz, 2H), 6.87 (d, J=7.3 Hz, 2H), 6.57 (s, b, 2H), 5.05 (s, 2H), 4.17 (s, 2H), 2.21 (m, 1H), 1.60 (m, 1H), 1.29 (m, 1H), 1.18 (m, 1H). ES-MS m/z 197.

Example 17

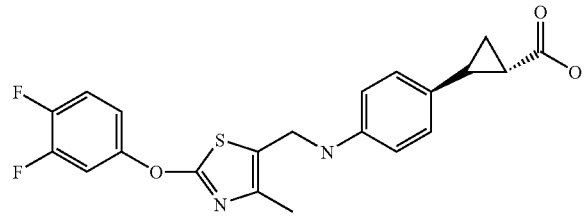

Racemic-(trans)-2-{4-[({2-[(3,4-difluorophenyl)oxy]-4-methyl-1,3-thiazol-5-yl}methyl)amino]phenyl}cyclopropanecarboxylic Acid (I-2q)

To a mixture of racemic-(trans)-2-(4-aminophenyl)cyclopropanecarboxylic acid (I-1) (0.054 g, 0.305 mmol) in dichloroethane (2 mL) was added 2-[(3,4-difluorophenyl)oxy]-4-methyl-1,3-thiazole-5-carbaldehyde (0.072 g, 0.282 mmol). The mixture was stirred for 12 h followed by addition of sodium triacetoxyborohydride (0.092 g, 0.434 mmol). The mixture was stirred for 5 h at RT. Water was added (10 mL), and the layers were separated. The aqueous phase was extracted with CH₂Cl₂ (2×10 mL). The combined organics were dried with MgSO₄ and concentrated. The crude material was purified by chromatography (EtOAc/hexanes) to give the title compound as a yellow solid (0.077 g, 51%). ¹H NMR (400 MHz, DMSO-d₆): δ 7.59-7.47 (m, 2H), 7.18 (m, 1H), 6.87 (d, J=8.4 Hz, 2H), 6.51 (d, J=8.4 Hz, 2H), 4.23 (s, 2H), 2.47 (m, 1H), 2.17 (s, 3H), 1.59 (m, 1H), 1.29 (m, 1H), 1.18 (m, 1H). ES-MS m/z 416.98 (MH+).

Example 18

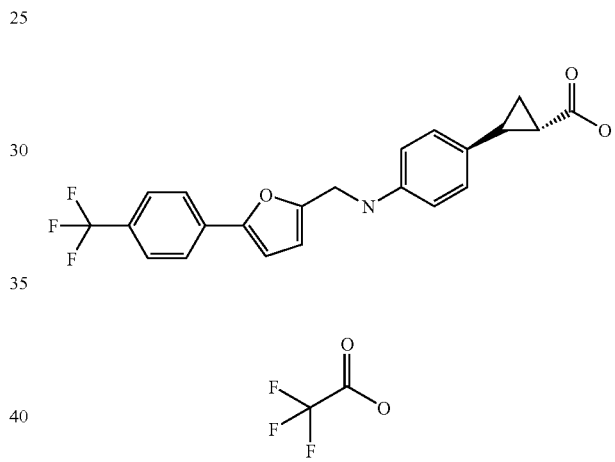

Racemic-(trans)-2-{4-[({5-[4-(trifluoromethyl)phenyl]-2-furanyl}methyl)amino]phenyl}cyclopropanecarboxylic Acid Trifluoroacetate (I-2r)

To a mixture of racemic-(trans)-2-(4-aminophenyl)cyclopropanecarboxylic acid (I-1) (0.071 g, 0.401 mmol) in dichloroethane (3 mL) was added 5-[4-(trifluoromethyl)phenyl]-2-furancarbaldehyde (0.081 0.337 mmol). The mixture was stirred for 12 h followed by addition of sodium triacetoxyborohydride (0.110 g, 0.519 mmol). The mixture was stirred for 7 h at RT. Water was added (10 mL). The aqueous phase was extracted with EtOAc (3×10 mL). The combined organics were dried with MgSO₄ and concentrated. The crude material was purified by preparative HPLC (10% to 100% CH₃CN/H₂O with 0.05% TFA) to give the title compound as a yellow solid (0.051 g, 17%). ¹H NMR (400 MHz, DMSO-d₆): δ 7.83 (d, J=8.2 Hz, 2H), 7.74 (d, J=8.4 Hz, 2H), 7.06 (d, J=3.5 Hz, 1H), 6.87 (d, J=8.4 Hz, 2H), 6.59 (d, J=8.4 Hz, 2H), 6.42 (d, J=3.3 Hz, 1H), 4.29 (s, 2H), 2.20 (m, 1H), 1.59 (m, 1H), 1.29 (m, 1H), 1.19 (m, 1H). ES-MS m/z 400.02 (MH−).

Example 19

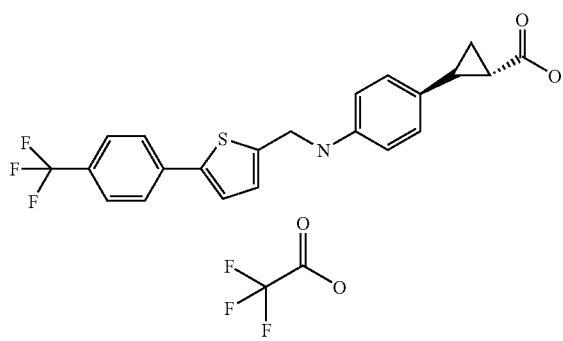

Racemic-(trans)-2-{4-[({5-[4-(trifluoromethyl)phenyl]-2-thienyl}methyl)amino]phenyl}cyclopropanecarboxylic Acid Trifluoroacetate (I-2s)

To a mixture of racemic-(trans)-2-(4-aminophenyl)cyclopropanecarboxylic acid (I-1) (0.058 g, 0.327 mmol) in dichloroethane (2.5 mL) was added 5-[4-(trifluoromethyl)phenyl]-2-thiophenecarbaldehyde (0.071 0.277 mmol). The mixture was stirred for 12 h followed by addition of sodium triacetoxyborohydride (0.090 g, 0.425 mmol). The mixture was stirred for 7 h at RT. Water was added (10 mL), and the layers were separated. The aqueous phase was extracted with EtOAc (3×10 mL). The combined organics were dried with MgSO₄ and concentrated. The crude material was purified by preparative HPLC (10% to 100% CH₃CN/H₂O with 0.05% TFA) to give the title compound as a yellow solid (0.048 g, 15%). ¹H NMR (400 MHz, DMSO-d₈): δ7.77 (d, J=8.2 Hz, 2H), 7.69 (d, J=8.4 Hz, 2H), 7.51 (d, J=3.7 Hz, 1H), 7.06 (d, J=3.7 Hz, 1H), 6.85 (d, J=8.4 Hz, 2H), 6.55 (d, J=8.6 Hz, 2H), 4.43 (s, 2H), 2.19 (m, 1H), 1.59 (m, 1H), 1.28 (m, 1H), 1.18 (m, 1H). ES-MS m/z 416.03 (MH−).

Example 20

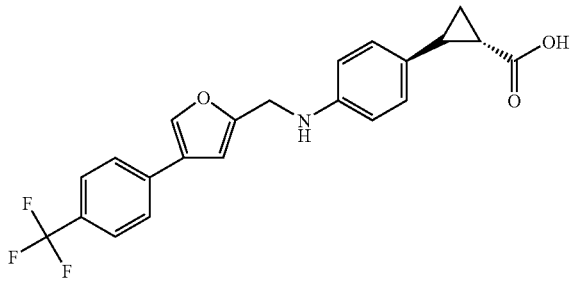

Racemic-(trans)-2-{4-[({4-[4-(trifluoromethyl)phenyl]-2-furanyl}methyl)amino]phenyl}cyclopropanecarboxylic Acid (I-2t)

A mixture of racemic-(trans)-2-(4-aminophenyl)cyclopropanecarboxylic acid (I-1) (0.060 g, 0.339 mmols) and dichloroethane was heated slightly and allowed to cool before addition of 4-[4-(trifluoromethyl)phenyl]-2-furancarbaldehyde (0.075 g, 0.312 mmols). The mixture was stirred for 7 h, followed by addition of sodium triacetoxyborohydride (0.104 g, 0.491 mmols). After 12 h, the mixture was partitioned between water and CH₂Cl₂ (10 mL each). The aqueous phase was extracted with CH₂Cl₂ (1×10 mL). The combined organics were dried with MgSO₄ and concentrated to give the title compound as a yellow solid (0.139 g, quant). ¹H NMR (400 MHz, DMSO-d₆): δ 12.01 (s, 1H), 8.23 (s, 1H), 7.75 (d, J=8.24 Hz, 2H), 7.68 (d, J=8.42 Hz, 2H), 6.85 (d, J=8.42 Hz, 2H), 6.81 (s, 1H), 6.56 (d, J=8.61 Hz, 2H), 6.05 (t, J=5.95 Hz, 1H), 4.22 (d, H=5.86 Hz, 2H), 2.18 (m, 1H), 1.58 (m, 1H), 1.27 (m, 1H), 1.16 (m, 1H). APCI m/z 399.93 (MH−).

Example 21

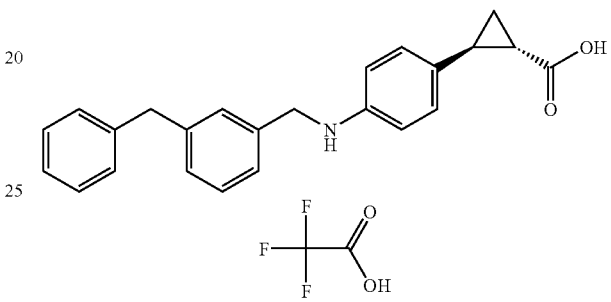

Racemic-(trans)-2-[4-({[3-(phenylmethyl)phenyl]methyl}amino)phenyl]cyclopropanecarboxylic Acid Trifluoroacetate (I-2u)

A mixture of racemic-(trans)-2-(4-aminophenyl)cyclopropanecarboxylic acid (I-1) (0.0735 g, 0.415 mmols) and dichloroethane was heated slightly and allowed to cool before addition of 3-(phenylmethyl)benzaldehyde (0.074 g, 0.377 mmols). The mixture was stirred for 3 h, followed by addition of sodium triacetoxyborohydride (0.124 g, 0.585 mmols). After 12 h, the mixture was partitioned between water and CH₂Cl₂ (10 mL each). The aqueous phase was extracted with CH₂Cl₂ (2×10 mL). The combined organics were dried with MgSO₄ and concentrated. The crude material was purified by preparative HPLC (10% to 100% CH₃CN/H₂O with 0.05% TFA) to give the title compound as a colorless solid (18 mg, 10%). ¹H NMR (400 MHz, DMSO-d₆): δ 7.13-7.26 (m, 8H), 7.06 (d, J=7.32 Hz, 1H), 6.84 (d, J=8.24 Hz, 2H), 6.53 (d, J=7.32 Hz, 2H), 4.19 (s, 2H), 3.87 (s, 2H), 2.20 (m, 1H), 1.59 (m, 1H), 1.29 (m, 1H), 1.18 (m, 1H). APCI m/z 358.02 (MH+).

Example 22

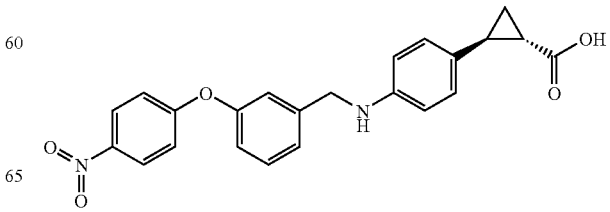

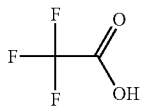

Racemic-(trans)-2-{4-[({3-[(4-nitrophenyl)oxy]
phenyl}methyl)amino]
phenyl}cyclopropanecarboxylic Acid Trifluoroacetate (I-2v)

A mixture of racemic-(trans)-2-(4-aminophenyl)cyclopropanecarboxylic acid (I-1) (0.072 g, 0.406 mmols) and dichloroethane/MeOH (1.5 mL each) was heated slightly and allowed to cool before addition of 3-[(4-nitrophenyl)oxy] benzaldehyde (0.089 g, 0.366 mmols). The mixture was stirred for 1 h, followed by addition of sodium triacetoxyborohydride (0.195 g, 0.92 mmols). After 12 h, additional sodium triacetoxyborohydride was added (0.19 g, 10.896 mmols), and the mixture was stirred for another 4 h. The mixture was partitioned between $CH_2Cl_2$ and water (10 mL each). The aqueous phase was extracted with $CH_2Cl_2$ (3×10 mL). The combined organics were dried with $MgSO_4$ and concentrated. The crude material was purified by preparative HPLC (10% to 100% $CH_3CN/H_2O$ with 0.05% TFA) to give the title compound as a yellow solid (16 mg, 8.5%). $^1$H NMR (400 MHz, DMSO-de): δ 8.20 (m, 2H), 7.41 (t, J=7.78 Hz, 1H), 7.25 (d, J=7.69 Hz, 1H), 7.10 (m, 1H), 7.00-7.08 (m, 3H), 6.83 (d, J=8.42 Hz, 2H), 6.47 (d, J=8.42 Hz, 2H), 4.27 (s, 2H), 2.19 (m, 1H), 1.58 (m, 1H), 1.28 (m, 1H), 1.17 (m, 1H). ESI m/z 405.22 (MH+).

Example 23

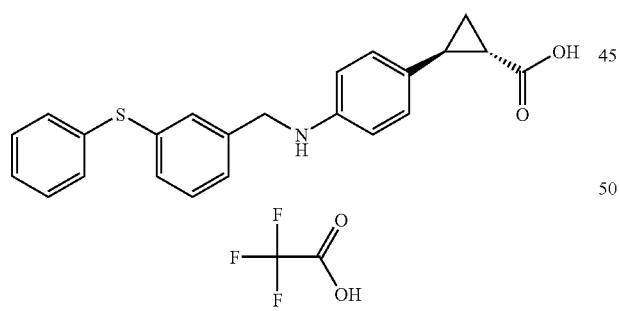

Racemic-(trans)-2-[4-({[3-(phenylthio)phenyl]
methyl}amino)phenyl]cyclopropanecarboxylic Acid
Trifluoroacetate (I-2w)

A solution of racemic-ethyl-2-(4-aminophenyl)cyclopropanecarboxylate (0.072 g, 0.351 mmols) [Galardon, E.; Le Maux, P.; Simonneaux, G. *Tetrahedron*, 2000, 56, 615-621. Huang, L.; Chen, Y.; Gao, G. -Y.; Zhang, X. P. *J. Org. Chem.*, 2003, 68, 8179-8184, each of which is incorporated by reference with regard to synthesis] and 3-(phenylthio) benzaldehyde (0.065 g, 0.303 mmols) was stirred in dichloroethane at RT for 2 h. Sodium triacetoxyborohydride (0.096 g, 0.453 mmols) was added, and the mixture was continued to stir for 12 h. The mixture was partitioned between $CH_2Cl_2$ and $H_2O$ (10 mL each). The aqueous phase was extracted with $CH_2Cl_2$ (2×10 mL). The combined organics were dried with $MgSO_4$ and concentrated. The crude material was purified by chromatography (EtOAc/hexanes) to give the title compound as a tan oil (0.104 g, 87%).

A mixture of racemic-ethyl-2-[4-({[3-(phenylthio)phenyl] methyl}amino)-phenyl]cyclopropanecarboxylate (0.104 g, 0.258 mmols) and aqueous 1M NaOH in THF/EtOH (1 mL each) was heated at 85° C. for 4 h. Upon cooling, the mixture was acidified with aqueous 5M HCl (pH<3). The mixture was extracted with EtOAc (15 mL). The organics were washed with water and brine (1×10 mL each), dried with $MgSO_4$, and concentrated. The crude material was purified by preparative HPLC (10% to 100% $CH_3CN/H_2O$ with 0.05% TFA) to give the title compound as an orange solid (0.072 g, 57%). $^1$H NMR (400 MHz, DMSO-de): δ 7.21-7.32 (m, 8H), 7.13 (m, 1H), 6.82 (d, J=8.42 Hz, 2H), 6.46 (d, J=8.24 Hz, 2H), 4.21 (s, 2H), 2.19 (m, 1H), 1.58 (m, 1H), 1.28 (m, 1H), 1.17 (m, 1H). APCI m/z 376.22 (MH+).

Example 24

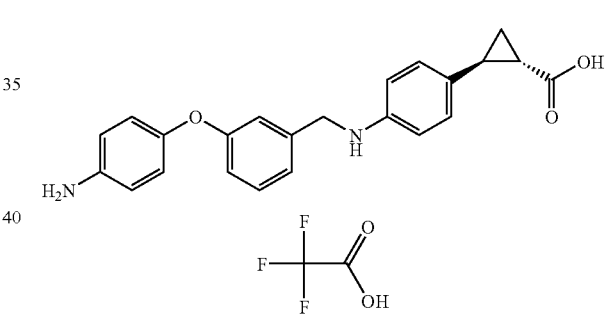

Racemic-(trans)-2-{4-[({3-[(4-aminophenyl)oxy]
phenyl}methyl)amino]
phenyl}cyclopropanecarboxylic Acid Trifluoroacetate 1-2x)

A mixture of racemic-(trans)-2-{4-[({3-[(4-nitrophenyl) oxy]phenyl}methyl)amino]phenyl}-cyclopropanecarboxylic acid (0.141 g, 0.349 mmols) and $PtO_2H_2O$ (10 mg, 0.044 mmols) in EtOH (3 mL) was exposed to a hydrogen atmosphere for 12 h. The mixture was filtered through Celite, and the Celite was washed with EtOH and EtOAc. The combined filtrates were concentrated. The crude material was purified by preparative HPLC (10% to 100% $CH_3CN/H_2O$ with 0.05% TFA) to give the title compound as an off-white solid (0.055 g, 26%). $^1$H NMR (400 MHz, DMSO-$d_6$): δ 7.30 (t, J=7.87 Hz, 1H), 7.17 (d, J=8.79 Hz, 2H), 7.10 (d, J=7.69 Hz, 1H), 6.98 (m, 3H), 6.79-6.83 (m, 3H), 6.46 (d, J=8.42 Hz, 2H), 4.21 (s, 2H), 2.18 (m, 1H), 1.58 (m, 1H), 1.28 (m, 1H), 1.16 (m, 1H). ESI m/z 375.11 (MH+).

Scheme III:

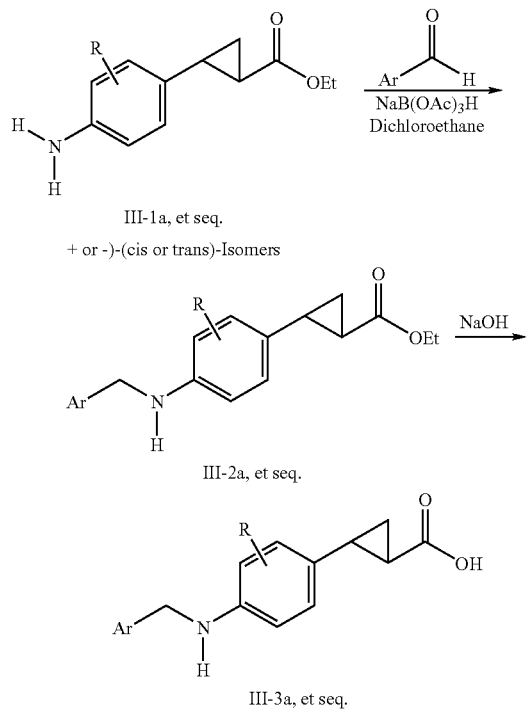

III-1a, et seq.
+ or −)-(cis or trans)-Isomers

III-2a, et seq.

III-3a, et seq.
General synthesis of enantiomerically enriched-(trans)-cyclopropanecarboxylic acid derivatives Example 25

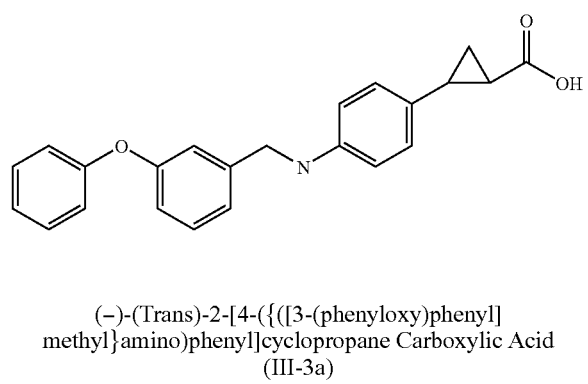

(−)-(Trans)-2-[4-({[3-(phenyloxy)phenyl]methyl}amino)phenyl]cyclopropane Carboxylic Acid (III-3a)

Sodium triacetoxyborohydride (0.30 g, 1.40 mmol) was added to a solution of (−)-(trans)-ethyl-2-(4-aminophenyl)cyclopropanecarboxylate (III-1a) (0.116 g, 0.56 mmol) and 3-phenoxybenzaldehyde (1.15 g, 0.56 mmol) in 5 mL of dichloroethane. The mixture was stirred at room temperature for one hour and then partitioned between chloroform and saturated aqueous sodium bicarbonate. The organic phase was dried over anhydrous sodium sulfate and the solvent evaporated. The residue was purified by chromatography (silica gel, hexane:ethyl acetate) to give (−)-(trans)-ethyl-2-[4-({[3-(phenyloxy)phenyl]methyl}amino)phenyl]cyclopropanecarboxylate (III-2a) (0.167 g, 77%) as a colorless oil. $^1$H NMR (400 MHz, CDCl$_3$) δ 7.34-7.26 (m, 3H), 7.11 (t, J=7.32 Hz, 2H), 7.02 (m, 1H), 6.99 (d, J=8.60 Hz, 2H), 6.92 (d, J=8.42 Hz, 2H), 6.89 (m, 1H), 6.54 (d, J=8.60 Hz, 2H), 4.19 (s, 2H), 4.17 (q, J=7.14 Hz, 2H), 4.03 (br s, 1H), 2.44 (m, 1H), 1.78 (m, 1H), 1.52 (m, 1H), 1.28 (t, J=7.14 Hz, 3H), 1.25 (m, 1H). ES-MS m/z 388 (MH+). Aqueous sodium hydroxide (1.0 mL of a 25% solution) was added to a solution of III-2a (0.167 g, 0.43 mmol) in 4 mL of methanol and the mixture was heated at reflux for 8 hours. The volatile solvents were removed under vacuum, water was added, and the pH was adjusted to 5 with saturated aqueous sodium bisulfate. The mixture was extracted with dichloromethane, the organic phase was dried over sodium sulfate and concentrated to give 0.192 g of the title compound (III-3a) as a white solid. $^1$H NMR (400 MHz, DMSO-d$_6$) δ 7.34 (t, J=8.42 Hz, 2H), 7.29 (t, J=7.87 Hz, 1H), 7.10 (m, 2H), 6.98 (s, 1H), 6.93 (d, J=7.68 Hz, 2H), 6.81 (d, J=8.42 Hz, 1H), 6.75 (d, J=8.23 Hz, 2H), 6.42 (d, J=8.42 Hz, 2H), 6.08 (m, 1H), 4.20 (m, 2H), 2.02 (m, 1H), 1.44 (m, 1H), 1.15 (m, 1H), 0.91 (m, 1H). ES-MS m/z 360 (MH+). $[\alpha]^{25,D}$=−187° (dichloromethane, c=4). Product was determined to be >99% ee by chiral SFC according to Method 1.

Example 26

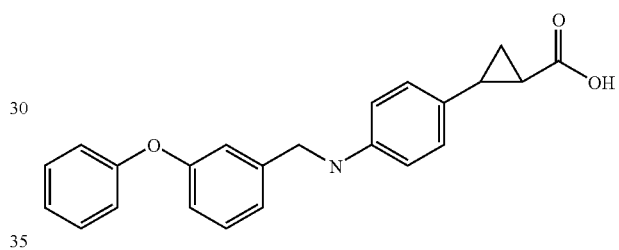

(+)-(Trans)-2-{4-[(3-phenoxybenzyl)amino]phenyl}cyclopropanecarboxylic Acid (III-3b)

Experimental procedure analogous to that described for synthesis of compounds III-2a and III-3a but instead using (+)-(trans)-ethyl-2-(4-aminophenyl)cyclopropanecarboxylate (III-1b) (0.100 g, 0.49 mmol), the title compound (III-3b) was obtained (0.115 g, 65% yield over two steps) as a white solid. 1H NMR (400 MHz, DMSO-d$_6$) δ 7.30 (m, 3H), 7.13 (m, 2H), 6.96 (m, 3H), 6.83 (m, 1H), 6.81 (d, J=8.4 Hz, 2H), 6.45 (d, J=8.6 Hz, 2H), 6.15 (m, 1H), 4.22 (d, J=5.3 Hz, 2H), 2.15 (m, 1H), 1.56 (m, 1H), 1.26 (m, 1H), 1.10 (m, 1H). ES-MS m/z 360 (MH+). $[\alpha]^{25,D}$=+191° (dichloromethane, c=3).). Product was determined to be 96% ee by chiral SFC according to Method 1.

Example 27

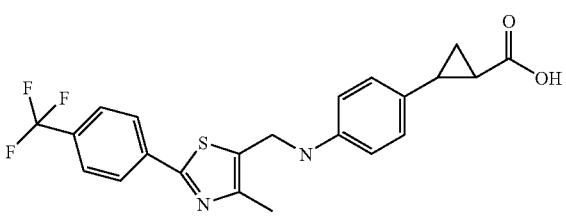

(+)-(Trans)-2-{4-[({4-methyl-2-[4-(trifluoromethyl) phenyl]-1,3-thiazol-5-yl}methyl)amino] phenyl}cyclopropanecarboxylic Acid (III-3c)

Experimental procedure analogous to that described for synthesis of compounds III-2a and III-3a but instead using (+)-(trans)-ethyl-2-(4-aminophenyl)cyclopropanecarboxylate (III-1b) (0.61 g, 2.97 mmol) and 4-methyl-2-[4-(trifluoromethyl)phenyl]-1,3-thiazole-5-carbaldehyde to give 0.30 g (25% yield) of pure title compound as a yellow solid. $^1$H NMR (400 MHz, CDCl$_3$) δ 7.98 (d, J=7.87 Hz, 2H), 7.65 (d, J=8.24 Hz, 2H), 6.97 (d, J=8.42 Hz, 2H), 6.60 (d, J=8.61 Hz, 2H), 4.46 (s, 2H), 2.51 (m, 1H), 2.50 (s, 3H), 1.79 (m, 1H), 1.59 (m, 1H), 1.35 (m, 1H). ES-MS m/z 432 (MH+). $[\alpha]^{25}_D$=+128° (chloroform, c=3.8). Product was determined to be 96% ee by chiral SFC according to Method 2.

Example 28

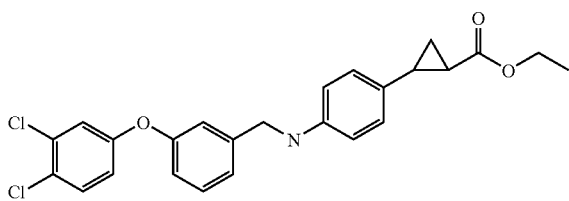

Enantiomerically Enriched (trans)-ethyl-2-{4-[({3-[(3,4-dichlorophenyl)oxy]phenyl}methyl)amino] phenyl}-cyclopropanecarboxylate (III-2d)

To a mixture of (+)-(trans)-ethyl-2-(4-aminophenyl)cyclopropanecarboxylate (III-1b) (0.099 g, 0.482 mmol) in dichloroethane (3.0 mL) was added 3-(3,4-dichlorophenoxy)benzaldehyde (0.116 g, 0.434 mmol). The mixture was stirred for 12 h followed by addition of sodium triacetoxyborohydride (0.140 g, 0.660 mmol). The mixture was stirred for 6 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by chromatography (EtOAc/hexanes) to give the title compound (0.17 g, 85%, mixture of ethyl and methyl ester). $^1$H NMR (400 MHz, CDCl$_3$) δ 7.35-7.31 (m, 2H), 7.14 (d, J=7.5 Hz, 1H), 7.05-7.00 (m, 2H), 6.92-6.87 (m, 3H), 6.81 (dd, J=8.8 Hz, 2.7 Hz, 1H), 6.52 (d, J=8.4 Hz, 2H), 4.31 (s, 2H), 4.14 (q, J=7.1 Hz, 2H), 2.42 (m, 1H), 1.77 (m, 1H), 1.51 (m, 1H), 1.28-1.20 (t+m, 4H).

Example 28a

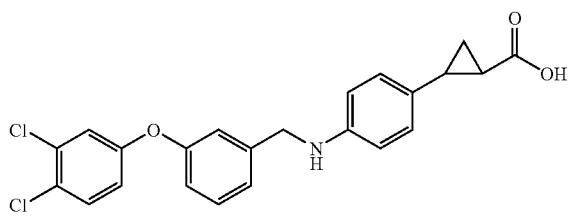

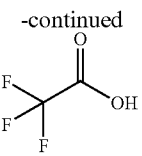

(+)-(Trans)-2-{4-[({3-[(3,4-dichlorophenyl)oxy] phenyl}methyl)amino] phenyl}cyclopropanecarboxylic Acid Trifluoroacetate (III-3d)

To a mixture of enantiomerically enriched (trans)-ethyl-2-{4-[({3-[(3,4-dichlorophenyl)oxy]phenyl}methyl)amino] phenyl}-cyclopropanecarboxylate (III-2d) (0.17 g, 0.372 mmol) in THF and EtOH (1 mL each) was added aqueous 1M NaOH solution (1 mL). The mixture was heated at 85° C. for 4 h. Upon cooling, the solution was acidified to pH=2-3 with aqueous 5M HCl solution. The mixture was extracted with CH$_2$Cl$_2$ (2×10 mL). The combined organics were dried with Na$_2$SO$_4$ and concentrated. The crude material was purified by preparative HPLC (10% to 100% CH$_3$CN/H$_2$O with 0.05% TFA) to give the title compound. $^1$H NMR (400 MHz, DMSO-d$_6$) δ7.57 (d, J=9.0 Hz, 1H), 7.35 (t, J=7.8 Hz, 1H), 7.20-7.17 (d+d, 2H), 7.02 (s, 1H), 6.94-6.90 (m, 2H), 6.82 (d, J=8.2 Hz, 2H), 6.46 (d, J=8.4 Hz, 2H), 4.24 (s, 2H), 2.18 (m, 1H), 1.58 (m, 1H), 1.28 (m, 1H), 1.16 (m, 1H). ES-MS m/z 428 (MH+).

Example 29

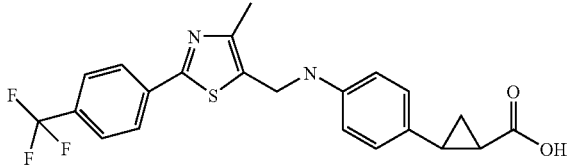

(−)-(cis)-2-{4-[({4-methyl-2-[4-(trifluoromethyl) phenyl]-1,3-thiazol-5-yl}methyl)amino] phenyl}cyclopropanecarboxylic Acid (III-3e)

Sodium triacetoxyborohydride (0.297 g, 1.40 mmol) was added to a solution of enantiomerically enriched-(cis)-ethyl-2-(4-aminophenyl)cyclopropanecarboxylate (0.115 g, 0.56 mmol) (III-1c) and 4-methyl-2-[4-(trifluoromethyl)phenyl]-1,3-thiazole-5-carbaldehyde (0.152 g, 0.56 mmol) in 5 mL of dichloroethane. The mixture was stirred at room temperature overnight. The reaction mixture was diluted with water and extracted with ethyl acetate. The organic phase was dried over anhydrous sodium sulfate and the solvent evaporated. The residue was purified by chromatography on silica gel with hexane:ethyl acetate to give 0.186 g (72% yield) of (cis)-ethyl-2-{4-[({4-methyl-2-[4-(trifluoromethyl)phenyl]-1,3-thiazol-5-yl}methyl)amino] phenyl}cyclopropanecarboxylate (III-2e) as a white solid. $^1$H NMR (400 MHz, CDCl$_3$) δ 7.96 (d, J=8.06 Hz, 2H), 7.63 (d, J=8.24 Hz, 2H), 7.10 (d, J=8.24 Hz, 2H), 6.57 (d, J=8.61 Hz, 2H), 4.43 (s, 2H), 3.91 (br s, 1H), 3.87 (q, J=7.14 Hz, 2H), 2.48 (s, 3H), 2.00 (m, 1H), 1.63 (m, 1H), 1.27 (m, 1H), 1.00 (t, J=7.14 Hz, 3H).

A mixture of III-2e (0.183 g, 0.40 mmol), 1 mL 15% aqueous sodium hydroxide and 10 mL of methanol was heated at reflux overnight. The solvent was evaporated under vacuum, and the residue was dissolved in water and acidified with concentrated hydrochloric acid. After extraction with dichloromethane and purification by chromatography on silica gel with hexane:ethyl acetate, 72 mg (42% yield) of the title compound (III-3e) was obtained as a yellow powder. 1H NMR (400 MHz, CDCl$_3$) δ 7.95 (d, J=8.24 Hz, 2H), 7.63 (d, J=8.24 Hz, 2 H), 7.09 (d, J=8.42 Hz, 2H), 6.56 (d, 8.61 Hz, 2H), 4.41 (s, 2H), 2.53 (m, 1H), 2.45 (s, 3H), 1.97 (m, 1H), 1.60 (m, 1H), 1.31 (m, 1H). ES-MS m/z 431 (M-H)$^+$. $[\alpha]^{25}_D$=−17.5° (chloroform, c=0.4). Product was determined to be 90% ee by chiral SFC according to Method 2.

Example 30

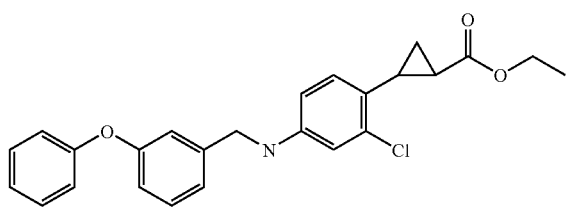

Enantiomerically Enriched-(trans)-ethyl-2-[2-chloro-4-({[3-(phenyloxy)phenyl]methyl}amino)phenyl]cyclopropanecarboxylate (III-2f)

Sodium triacetoxyborohydride (0.424 g, 2.00 mmol) was added to a solution of the enantiomerically enriched-(trans)-ethyl-2-(4-amino-2-chlorophenyl)cyclopropanecarboxylate (III-1d) (0.191 g, 0.80 mmol) and 3-phenoxybenzaldehyde (0.160 g, 0.80 mmol) in 8 mL of dichloroethane. The mixture was stirred at room temperature for one hour. The reaction mixture was partitioned between chloroform and water. The organic phase was washed with saturated aqueous sodium bicarbonate, dried over anhydrous sodium sulfate, the solvent evaporated and the residue purified by chromatography on silica gel with hexane:ethyl acetate to give 0.269 g (80% yield) of the title compound as a colorless oil. NMR (400 MHz, CDCl$_3$) δ 7.32 (t, J=7.51 Hz, 2H), 7.28 (t, J=8.42 Hz, 1H), 7.10 (t, J=8.24 Hz, 1H), 7.06 (d, J=8.24 Hz, 1H), 6.99 (d, J=7.69 Hz, 2H), 6.98 (m, 1H), 6.90 (dd, J=8.06 Hz, 2.38 Hz, 1H) 6.79 (d, J=8.42 Hz, 1H), 6.61 (d, J=2.38 Hz, 1H), 6.40 (dd, J=8.42 Hz, 2.38 Hz, 1H), 4.25 (d, J=5.49 Hz, 2H), 4.19 (q, J=7.14 Hz, 2H), 4.12 (br s, 1H), 2.60 (m, 1H), 1.69 (m, 1H), 1.53 (m, 1H), 1.28 (t, J=7.14 Hz, 3H), 1.25 (m, 1H). ES-MS m/z 422 (MH)+.

Example 30a

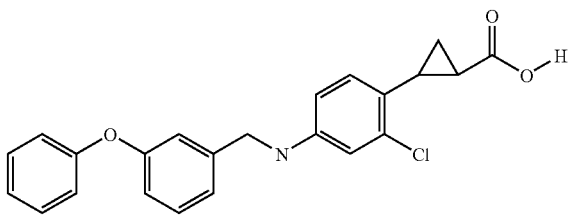

(+)-(Trans)-2-[2-chloro-4-({[3-(phenyloxy)phenyl]methyl}amino)phenyl]cyclopropanecarboxylic Acid (III-3f)

A solution of enantiomerically enriched-(trans)-ethyl-2-[2-chloro-4-({[3-(phenyloxy)phenyl]methyl}amino)phenyl]cyclopropanecarboxylate (III-2f) (0.269 g, 0.64 mmol) and 0.75 mL of 15% aqueous sodium hydroxide in 8 mL of methanol was heated at reflux for 1.5 hours. Methanol was evaporated and the residue was dissolved in water and acidified with concentrated hydrochloric acid. The resulting suspension was extracted with dichloromethane, the organic phase was washed with water and dried over anhydrous sodium sulfate and the solvent evaporated to give 0.217 g (86% yield) of the title compound as a white solid. NMR (400 MHz, CDCl$_3$) δ 7.32 (t, J=7.33 Hz, 2H), 7.28 (t, J=7.69 Hz, 1H), 7.09 (t, J=6.41 Hz, 1H), 7.06 (d, J=7.87 Hz, 1H), 6.98 (d, J=7.51 Hz, 2H), 6.99 (m, 1H), 6.90 (dd, J=7.87 Hz, 1.65 Hz, 1H), 6.80 (d, J=8.42 Hz, 1H), 6.61 (d, J=2.56 Hz, 1H), 6.40 (dd, J=8.42 Hz, 2.38 Hz, 1H), 4.26 (s, 2H), 2.66 (m, 1H), 1.70 (m, 1H), 1.60 (m, 1H), 1.33 (m, 1H). ES-MS m/z 394 (MH)+. $[\alpha]^{25,D}$=+170° (chloroform, c=1.2). Product was determined to be 98% ee by chiral SFC according to Method 1.

Example 31

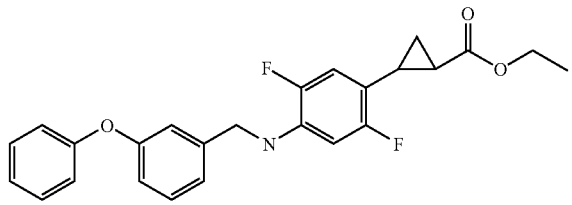

Enantiomerically Enriched-(trans)-ethyl-2-[2,5-difluoro-4-({[3-(phenyloxy)phenyl]methyl}amino)phenyl]cyclopropanecarboxylate (III-2g)

Sodium triacetoxyborohydride (0.244 g, 1.15 mmol) was added to a solution of enantiomerically enriched-(trans)-ethyl-2-(4-amino-2,5-difluorophenyl)cyclopropanecarboxylate (III-1e) (0.110 g, 0.46 mmol) and 3-phenoxybenzaldehyde (0.091 g, 0.46 mmol) in 5 mL of dichloroethane. The mixture was stirred at room temperature for one hour. The reaction mixture was partitioned between chlroroform and water. The organic phase was washed with saturated aqueous sodium bicarbonate, dried over anhydrous sodium sulfate and the solvent evaporated. The residue was purified by chromatography on silica gel with hexane:ethyl acetate to give 0.127 g (65% yield) of the title compound as a colorless oil. $^1$HNMR (400 MHz, CDCl$_3$) δ 7.32 (t, J=8.61Hz, 2H), 7.29 (t, J=7.69 Hz, 2H), 7.10 (t, J=7.14 Hz, 1H), 7.06 (d, J=7.69 Hz, 1H), 6.99 (d, J=7.51 Hz, 2H), 6.90 (dd, J=3.11, 8.06 Hz, 1H), 6.55 (dd, J=6.78, 12.09 Hz, 1H), 6.28 (dd, J=7.51, 11.72 Hz, H), 4.36 (br s, 1H), 4.29 (d, J=5.68 Hz, 2H), 4.15 (q, J=7.14 Hz, 2H), 2.50 (m, 1H), 7.79 (m, 1H), 1.53 (m, 1H), 1.27 (t, J=7.14 Hz, 3H), 1.22 (m, 1H).

Example 31a

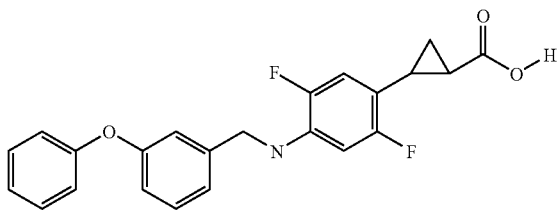

(+)-(trans)-2-[2,5-difluoro-4-({[3-(phenyloxy)phenyl]methyl}amino)phenyl]cyclopropanecarboxylic Acid (III-3g)

A solution of enantiomerically enriched-(trans)-ethyl-2-[2,5-difluoro-4-({[3-(phenyloxy)phenyl]methyl}amino)phenyl]cyclopropanecarboxylate (III-2g) (0.127 g, 0.30 mmol) and 0.5 mL of 15% aqueous sodium hydroxide in 5 mL of methanol was heated at reflux for 1.5 hours. Methanol was evaporated and the residue was dissolved in water and acidified with concentrated hydrochloric acid. The precipitated product was extracted with dichloromethane, the organic phase washed with water, dried over anhydrous sodium sulfate, and the solvent evaporated to give 0.099 g (83% yield) of the title compound as a white solid. 1 HNMR (400 MHz, CDCl$_3$) δ 7.33 (t, J=8.2 Hz, 2H), 7.31 (t, J=7.8 Hz, 1H), 7.11 (t, J=7.5 Hz, 1H), 7.07 (d, J=7.5 Hz, 2H), 7.00 (d, J=7.8 Hz, 2H), 6.91 (d, J=8.2 Hz, 1H), 6.57 (dd, J=11.8 Hz, 6.7 Hz, 1H), 6.29 (dd, J=11.5 Hz, 7.3 Hz, 1H), 4.30 (s, 2H), 2.59 (m, 1H), 1.78 (m, 1H), 1.59 (m, 1H), 1.33 (m, 1H). ES-MS m/z 394 (M-H)+. [α]$^{25,D}$=+140° (chloroform, c=0.8). Product was determined to be 88% ee by chiral SFC according to Method 1.

Example 32

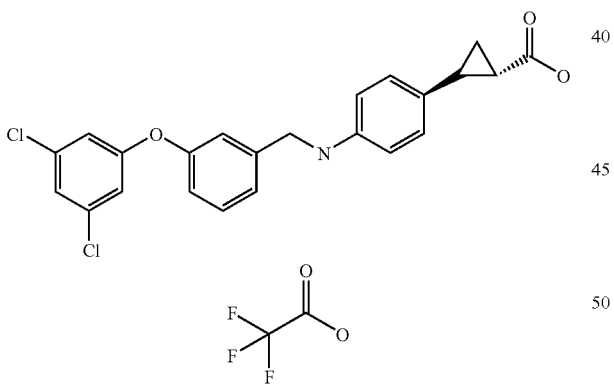

(+)-(trans)-2-{4-[({3-[(3,5-dichlorophenyl)oxy]phenyl}methyl)amino]phenyl}cyclopropanecarboxylic Acid trifluoroacetate (III-3h)

To a mixture of (+)-(trans)-ethyl-2-(4-aminophenyl)cyclopropanecarboxylate (III-1b) (0.101 g, 0.492 mmol) in dichloroethane (3 mL) was added 3-[(3,5-dichlorophenyl)oxy]benzaldehyde (0.118 g, 0.442 mmol). The mixture was stirred for 18 h followed by addition of sodium triacetoxyborohydride (0.148 g, 0.698 mmol). The mixture was stirred for 12 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by chromatography (EtOAc/hexanes) to give ethyl 2-{4-[({3-[(3,5-dichlorophenyl)oxy]phenyl}methyl)amino]phenyl}cyclopropanecarboxylate as a colorless oil (0.184 g, mixture of ethyl and methyl ester). The material was dissolved in THF/EtOH (1 mL each) and a 1M sodium hydroxide solution was added (1 mL). The mixture was heated at 85 C for 3.5 h. Upon cooling, the mixture was acidified (pH=2-3) with a 5M hydrochloric acid solution. Water was added (5 mL), and the mixture was extracted with CH$_2$Cl$_2$ (3×10 mL). The organics were washed with water and brine (1×10 mL each) and dried with MgSO4. The crude material was purified by preparative HPLC (10% to 100% CH$_3$CN/H$_2$O with 0.05% TFA) to give the title compound as an off-white solid (0.123 g, 57%). $^1$H NMR (400 MHz, DMSO-d$_6$): δ 12.13 (s, 1H), 7.37 (t, J=7.9 Hz, 1H), 7.32 (m, 1H), 7.20 (d, J=7.5 Hz, 1H), 7.06 (m, 1H), 6.95-6.93 (m, 2H), 6.81 (d, J=8.4 Hz, 2H), 6.45 (d, J=8.4 Hz, 2H), 6.21 (s, 1H), 4.25 (s, 2H), 2.17 (m, 1H), 1.57 (m, 1H), 1.27 (m, 1H), 1.16 (m, 1H). ES-MS m/z 428.01 (MH+).

Example 33

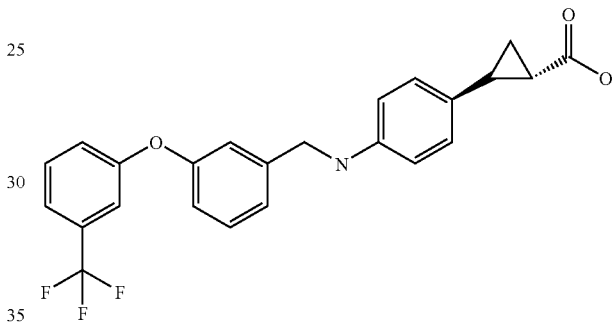

(+)-(trans)-2-(4-{[(3-{[3-(trifluoromethyl)phenyl]oxy}phenyl)methyl]amino}phenyl)cyclopropanecarboxylic Acid (III-31)

To a mixture of (+)-(trans)-ethyl-2-(4-aminophenyl)cyclopropanecarboxylate (III-1b) (0.093 g, 0.453 mmol) in dichloroethane (3.5 mL) was added 3-{[3-(trifluoromethyl)phenyl]oxy}benzaldehyde (70 uL, 0.404 mmol). The mixture was stirred for 18 h followed by addition of sodium triacetoxyborohydride (0.135 g, 0.637 mmol). The mixture was stirred for 12 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by chromatography (EtOAc/hexanes) to give ethyl 2-(4-{[(3-{[3-(trifluoromethyl)phenyl]oxy}phenyl)methyl]amino}phenyl)cyclopropanecarboxylate as a colorless oil (0.159 g, mixture of ethyl and methyl ester). The material was dissolved in THF/EtOH (1 mL each) and a 1M sodium hydroxide solution was added (1 mL). The mixture was heated at 85 C for 3.5 h. Upon cooling, the mixture was acidified (pH=2-3) with a 5M hydrochloric acid solution. Water was added (5 mL), and the mixture was extracted with CH$_2$Cl$_2$ (3×10 mL). The organics were washed with water and brine (1×10 mL each) and dried with MgSO4 to give the title compound as an orange oil (0.153 g, >100%, residual THF present). $^1$H NMR (400 MHz, DMSO-d$_6$): δ 7.41 (t, J=8.1 Hz, 1H), 7.30-7.35 (m, 2H), 7.20 (m, 1H), 7.10-7.17 (m, 2H), 7.02 (m, 1H), 6.92 (d, J=8.4 Hz, 2H), 6.90 (m, 1H), 6.56 (d, J=8.4 Hz, 2H), 4.31 (s, 2H), 2.50 (m, 1H), 1.77 (m, 1H), 1.57 (m, 1H), 1.32 (m, 1H). ES-MS m/z 428.16 (MH+).

Example 34

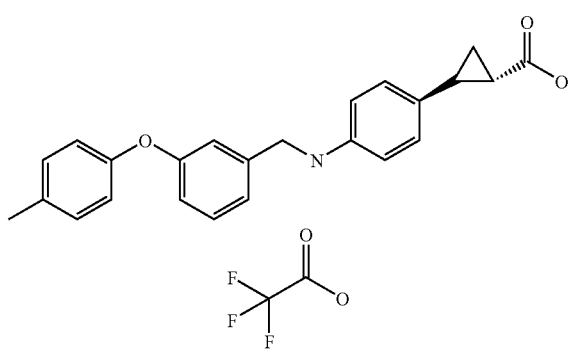

(+)-(trans)-2-{4-[({3-[(4-methylphenyl)oxy]phenyl}methyl)amino]phenyl}cyclopropanecarboxylic Acid Trifluoroacetate (III-3j)

To a mixture of (+)-(trans)-ethyl-2-(4-aminophenyl)cyclopropanecarboxylate (III-1b) (0.090 g, 0.438 mmol) in dichloroethane (3.5 mL) was added 3-[(4-methylphenyl)oxy]benzaldehyde (75 uL, 0.389 mmol). The mixture was stirred for 18 h followed by addition of sodium triacetoxyborohydride (0.124 g, 0.698 mmol). The mixture was stirred for 36 h at RT. Water was added (10 mL), and the layers were separated. The aqueous phase was extracted with CH$_2$Cl$_2$ (2×10 mL). The combined organics were dried with MgSO$_4$ and concentrated. The crude material was purified by chromatography (EtOAc/hexanes) to give ethyl 2-{4-[({3-[(4-methylphenyl)oxy]phenyl}methyl)amino]phenyl}cyclopropanecarboxylate as a tan oil (0.064 g, mixture of ethyl and methyl ester). The material was dissolved in THF/EtOH (1 mL each) and a 1M sodium hydroxide solution was added (1 mL). The mixture was heated at 85 C for 3.5 h. Upon cooling, the mixture was acidified (pH=2-3) with a 5M hydrochloric acid solution. Water was added (5 mL), and the mixture was extracted with CH$_2$Cl$_2$ (3×10 mL). The organics were washed with water and brine (1×10 mL each) and dried with MgSO4. The crude material was purified by preparative HPLC (10% to 100% CH$_3$CN/H$_2$O with 0.05% TFA) to give the title compound as an off-white solid (0.072 g, 92%). $^1$H NMR (400 MHz, DMSO-d$_6$): δ 7.26 (t, J=7.9 Hz, 1H), 7.13 (d, J=8.4 Hz, 2H), 7.05 (d, J=7.7 Hz, 1H), 6.92 (m, 1H), 6.83 (d+m, 4H), 6.76 (dd, J=8.1 Hz, 2.2 Hz, 1H), 6.47 (d, J=8.1 Hz, 2H), 4.20 (s, 2H), 2.25 (s, 3H), 2.19 (m, 1H), 1.58 (m, 1H), 1.28 (m, 1H), 1.17 (m, 1H). ES-MS m/z 374.12 (MH+).

Scheme IV

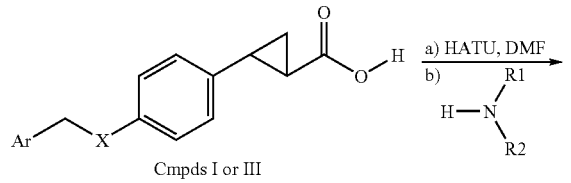

-continued

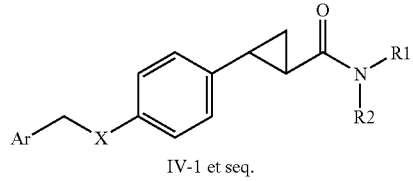

IV-1 et seq.

Example 35

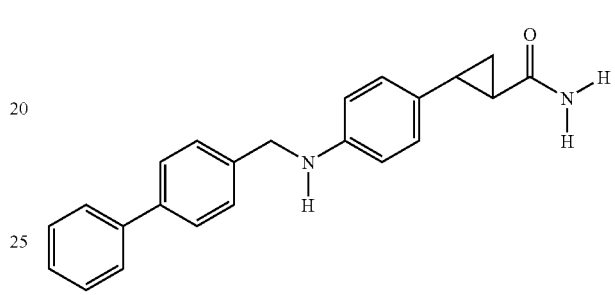

Racemic-(trans)-2-{4-[(4-biphenylmethyl)amino]phenyl}cyclopropanecarboxamide (IV-1)

HATU (0.20 g, 0.53 mmol) and racemic-(trans)-2-{4-[(4-biphenylylmethyl)amino]phenyl}cyclopropanecarboxylic acid (I-2b) (0.14 g, 0.41 mmol) in DMF (10 mL) were stirred at RT for 5 min, then ammonium hydroxide (2 mL) was added. The solution was stirred at RT for 16 h, then water (50 mL) and ethyl acetate (50 mL) were added and the organic layer was separated, washed with saturated NaHCO$_3$ solution (50 mL), dried over Na$_2$SO$_4$, filtered and concentrated. The crude material was purified on silica gel eluting with an increasing gradient from 40% ethyl acetate/hexanes to 100% ethyl acetate to give the title compound as a white powder (0.022 g, 16%). $^1$H NMR (400 MHz, DMSO) δ7.64-7.59 (m, 4H), 7.51-7.34 (m, 6H), 6.81-6.79 (m, 3H), 6.51 (d, J=8.5 Hz, 2H), 6.18 (t, J=5.7 Hz, 1H), 4.29 (d, J=5.7 Hz, 2H), 2.05-2.01 (m, 1H), 1.65-1.61 (m, 1H), 1.21-1.16 (m, 1H), 1.03-0.99 (m, 1H). ES-MS m/z 343.2 (MH+).

Example 36

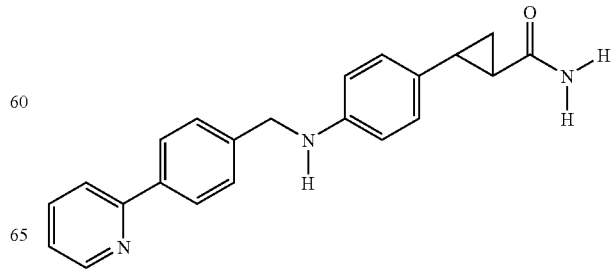

Racemic-(trans)-2-[4-({[4-(2-pyridinyl)phenyl]methyl}amino)phenyl]cyclopropanecarboxamide (IV-2)

HATU (0.11 g, 0.29 mmol) and racemic-(trans)-2-[4-({[4-(2-pyridinyl)phenyl]methyl}amino)phenyl]cyclopropanecarboxylic acid (I-2c) (0.077 g, 0.22 mmol) in DMF (5 mL) were stirred at RT for 10 min, then ammonium hydroxide (2 mL) was added. The solution was stirred at RT for 16 h, then water (50 mL) and dichloromethane (50 mL) were added and the organic layer was separated, washed with water (50 mL), dried over Na$_2$SO$_4$, filtered and concentrated to give the title compound as a white powder (0.029 g, 38%). $^1$H NMR (400 MHz, DMSO) δ 8.64 (d, J=3.8 Hz, 1H), 8.02 (d, J=8.1 Hz, 2H), 7.92 (d, J=8.0 Hz, 1H), 7.86 (t, J=7.9 Hz, 1H), 7.49 (s, 1H), 7.44 (d, J=8.0 Hz, 2H), 7.33 (t, J=5.3 Hz, 1H), 6.81-6.79 (m, 3H), 6.50 (d, J=8.4 Hz, 2H), 6.19 (t, J=6.1 HZ, 1H), 4.30 (d, J=6.0 Hz, 2H), 2.05-2.00 (m, 1H), 1.64-1.60 (m, 1H), 1.20-1.15 (m, 1H), 1.03-0.98 (m, 1H). ES-MS m/z 344.2 (MH+).

Example 37

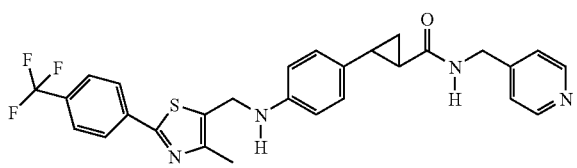

Racemic-(trans)-2-{4-[({4-methyl-2-[4-(trifluoromethyl)phenyl]-1,3-thiazol-5-yl}methyl)amino]phenyl}-N-(4-pyridinylmethyl)cyclopropanecarboxamide (IV-3)

HATU (0.14 g, 0.37 mmol) and racemic-(trans)-2-{4-[({4-methyl-2-[4-(trifluoromethyl)phenyl]-1,3-thiazol-5-yl}methyl)amino]phenyl}cyclopropanecarboxylic acid (I-2m) (0.12 g, 0.28 mmol) in DMF (10 mL) were stirred at RT for 45 min, then (4-pyridinylmethyl)amine (0.36 g, 3.33 mmol) was added. The solution was stirred at RT for 16 h, then saturated NaHCO$_3$ solution (50 mL) and ethyl acetate (50 mL) were added. The organic layer was separated, washed with saturated NaHCO$_3$ solution (50 mL), water (50 mL), brine (50 mL), dried over MgSO$_4$, filtered and concentrated. The crude material was partially dissolved in dichloromethane (10 mL) and diethyl ether was added (10 mL). The white solid was filtered, washed with diethyl ether, and dried to give the title compound as a white powder (0.094 g, 64%). $^1$H NMR (400 MHz, CDCl$_3$) δ 8.56 (d, J=5.1 Hz, 2H), 7.97 (d, J=8.4 Hz, 2H), 7.65 (d, J=8.2 Hz, 2H), 7.20 (d, J=4.7 Hz, 2H), 6.96 (d, J=8.1 Hz, 2H), 6.60 (d, J=8.4 Hz, 2H), 5.99 (t, J=5.7 Hz, 1H), 4.49 (t, J=5.9 Hz, 2H), 4.45 (s, 2H), 4.02 (bs, 1H), 2.49 (s, 3H), 2.49-2.45 (m, 1H), 1.63-1.53 (m, 2H), 1.25-1.21 (m, 1H). ES-MS m/z 523.2 (MH+).

Example 38

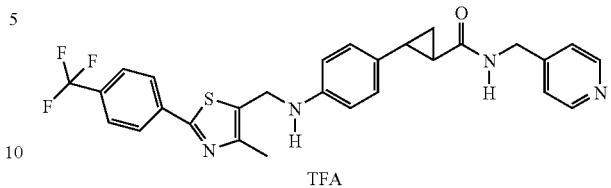

Enantiomerically Enriched (trans)-2-{4-[({4-methyl-2-[4-(trifluoromethyl)phenyl]-1,3-thiazol-5-yl}methyl)amino]phenyl}-N-(4-pyridinylmethyl)cyclopropanecarboxamide TFA Salt (IV-4)

HATU (0.071 g, 0.18 mmol) and (+)-(trans)-2-{4-[({4-methyl-2-[4-(trifluoromethyl)phenyl]-1,3-thiazol-5-yl}methyl)amino]phenyl}cyclopropanecarboxylic acid (III-3c) (0.062 g, 0.14 mmol) in DMF (5 mL) were stirred at RT for 45 min, then (4-pyridinylmethyl)amine (0.030 g, 0.28 mmol) was added. The solution was stirred at RT for 16 h, then saturated NaHCO$_3$ solution (50 mL) and ethyl acetate (50 mL) were added. The organic layer was separated, washed with saturated NaHCO$_3$ solution (50 mL), water (50 mL), brine (50 mL), dried over MgSO$_4$, filtered and concentrated. The crude material was partially dissolved in dichloromethane (10 mL) and diethyl ether was added (10 mL). The solid was filtered, washed with diethyl ether, and dried to give the title compound as an orange residue. The solid was dissolved in CH$_2$Cl$_2$ (5 mL) and trifluoroacetic acid (1 mL) was added. The solution was concentrated to dryness to give the title compound as a TFA salt. $^1$H NMR (400 MHz, DMSO) δ 8.80 (t, J=5.9 Hz, 1H), 8.71 (d, J=5.7 Hz, 2H), 8.03 (d, J=8.4 Hz, 2H), 7.78 (d, J=8.3 Hz, 2H), 7.64 (d, J=5.9 Hz, 2H), 6.87 (d, J=8.3 Hz, 2H), 6.54 (d, J=8.2 Hz, 2H), 4.47 (bs, 2H), 4.41 (s, 2H), 2.43 (s, 3H), 2.15-2.10 (m, 1H), 1.81-1.77 (m, 1H), 1.28-1.23 (m, 1H), 1.14-1.09 (m, 1H).

Example 39

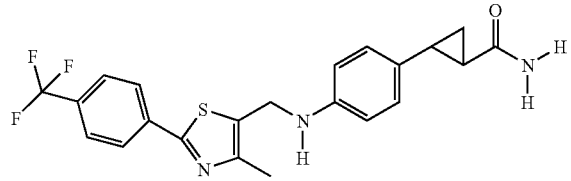

Enantiomerically Enriched (trans)-2-{4-[({4-methyl-2-[4-(trifluoromethyl)phenyl]-1,3-thiazol-5-yl}methyl)amino]phenyl}cyclopropanecarboxamide (IV-5)

HATU (0.23 g, 0.60 mmol) and (+)-(trans)-2-{4-[({4-methyl-2-[4-(trifluoromethyl)phenyl]-1,3-thiazol-5-yl}methyl)amino]phenyl}cyclopropanecarboxylic acid (III-3c) (0.20 g, 0.46 mmol) in DMF (15 mL) were stirred at RT for 10 min, then a solution of ammonia in MeOH (3 mL, 21 mmol) was added. The solution was stirred at RT for 16 h, then water (50 mL) and dichloromethane (50 mL) were added and the organic layer was separated, washed with water (50 mL), dried over Na₂SO₄, filtered and concentrated. The crude material was purified on silica gel eluting with an increasing gradient from 50% ethyl acetate/hexanes to 100% ethyl acetate to give the title compound as a white powder (0.095 g, 48%). ¹H NMR (400 MHz, DMSO) δ 8.01 (d, J=8.0 Hz, 2H), 7.76 (d, J=8.1 Hz, 2H), 7.46 (s, 1H), 6.82 (d, J=8.2 Hz, 2H), 6.78 (s, 1H), 6.51 (d, J=8.3 Hz, 2H), 6.20 (t, J=5.8 Hz, 1H), 4.38 (d, J=5.6 Hz, 2H), 2.42 (s, 3H), 2.04-1.99 (m, 1H), 1.63-1.59 (m, 1H), 1.18-1.14 (m, 1H), 1.01-0.97 (m, 1H). ES-MS m/z 433.2 (MH+).

Example 40

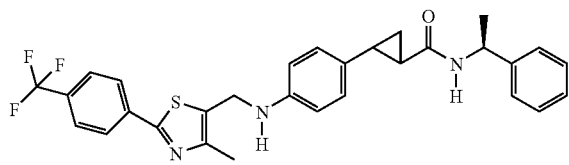

Enantiomerically Enriched (trans)-2-{4-[({4-methyl-2-[4-(trifluoromethyl)phenyl]-1,3-thiazol-5-yl}methyl)amino]phenyl}-N-[(1S)-1-phenylethyl]cyclopropanecarboxamide (IV-6)

HATU (0.154 g, 0.41 mmol) and (+)-(trans)-2-{4-[({4-methyl-2-[4-(trifluoromethyl)phenyl]-1,3-thiazol-5-yl}methyl)amino]phenyl}cyclopropanecarboxylic acid (III-3c) (0.135 g, 0.31 mmol) in DMF (10 mL) were stirred at RT for 15 min, then [(1S)-1-phenethyl]amine (0.50 g) was added. The solution was stirred at RT for 1 h, then saturated NaHCO₃ solution (20 mL) was added. The resulting solid was filtered, washed with water (10 mL) and dissolved in ethyl acetate (50 mL). The organic layer was dried over MgSO₄, filtered and concentrated to give the title compound as a white powder (0.115 g, 69%). ¹H NMR (400 MHz, DMSO) δ8.43 (d, J=8.3 Hz, 1H), 8.01 (d, J=8.1 Hz, 2H), 7.76 (d, J=8.4 Hz, 2H), 7.28-7.24 (m, 4H), 7.20-7.15 (m, 1H), 6.80 (d, J=8.6 Hz, 2H), 6.50 (d, J=8.4 Hz, 2H), 6.20 (t, J=6.0 Hz, 1H), 4.89 (p, J=7.0 Hz, 1H), 4.38 (d, J=5.9 Hz, 2H), 2.41 (s, 3H), 2.03-1.98 (m, 1H), 1.76-1.72 (m, 1H), 1.30 (d, J=7.0 Hz, 3H), 1.22-1.17 (m, 1H), 1.02-0.98 (m, 1H).

Example 41

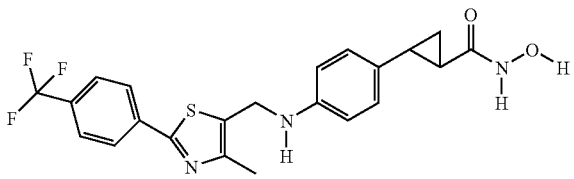

Enantiomerically Enriched (trans)-N-hydroxy-2-{4-[({4-methyl-2-[4-(trifluoromethyl)phenyl]-1,3-thiazol-5-yl}methyl)amino]phenyl}cyclopropanecarboxamide (IV-7)

HATU (0.154 g, 0.41 mmol) and (+)-(trans)-2-{4-[({4-methyl-2-[4-(trifluoromethyl)phenyl]-1,3-thiazol-5-yl}methyl)amino]phenyl}cyclopropanecarboxylic acid (III-3c) (0.135 g, 0.31 mmol) in DMF (10 mL) were stirred at RT for 15 min, then hydroxylamine hydrochloride (0.50 g) was added. The solution was stirred at RT for 1 h, then saturated NaHCO₃ solution (20 mL) was added. The resulting solid was filtered, washed with water (10 mL) and dissolved in ethyl acetate (50 mL). The organic layer was dried over MgSO₄, filtered and concentrated to give the title compound as a white powder (0.067 g, 48%). ¹H NMR (400 MHz, DMSO) δ 10.45 (s, 1H), 8.68 (s, 1H), 8.02 (d, J=8.1 Hz, 2H), 7.77 (d, J=8.3 Hz, 2H), 6.82 (d, J=8.5 Hz, 2H), 6.51 (d, J=8.6 Hz, 2H), 6.21 (t, J=5.7 Hz, 1H), 4.38 (d, J=5.9 Hz, 2H), 2.42 (s, 3H), 2.07-2.02 (m, 1H), 1.48-1.43 (m, 1H), 1.21-1.16 (m, 1H), 1.06-1.01 (m, 1H).

Example 42

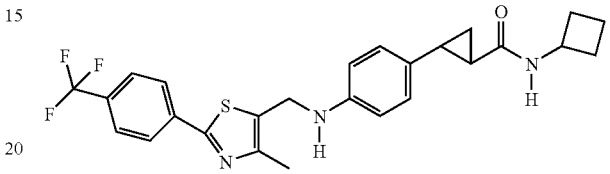

Enantiomerically Enriched (trans)-N-cyclobutyl-2-{4-[({4-methyl-2-[4-(trifluoromethyl)phenyl]-1,3-thiazol-5-yl}methyl)amino]phenyl}cyclopropanecarboxamide (IV-8)

HATU (0.154 g, 0.41 mmol) and (+)-(trans)-2-{4-[({4-methyl-2-[4-(trifluoromethyl)phenyl]-1,3-thiazol-5-yl}methyl)amino]phenyl}cyclopropanecarboxylic acid (III-3c) (0.135 g, 0.31 mmol) in DMF (10 mL) were stirred at RT for 15 min, then cyclobutylamine (0.50 g) was added. The solution was stirred at RT for 1 h, then saturated NaHCO₃ solution (20 mL) was added. The resulting solid was filtered, washed with water (10 mL) and dissolved in ethyl acetate (50 mL). The organic layer was dried over MgSO₄, filtered and concentrated to give the title compound as a white powder (0.116 g, 77%). ¹H NMR (400 MHz, DMSO) δ8.23 (d, J=7.5 Hz, 1H), 8.01 (d, J=8.1 Hz, 2H), 7.76 (d, J=8.0 Hz, 2H), 6.81 (d, J=8.3 Hz, 2H), 6.51 (d, J=8.4 Hz, 2H), 6.20 (t, J=5.8 Hz, 1H), 4.38 (d, J=5.5 Hz, 2H), 4.19-4.13 (m, 1H), 2.42 (s, 3H), 2.10-2.06 (m, 2H), 2.04-1.99 (m, 1H), 1.85-1.75 (m, 2H), 1.59-1.50 (m, 3H), 1.18-1.13 (m, 1H), 1.01-0.96 (m, 1H).

Example 43

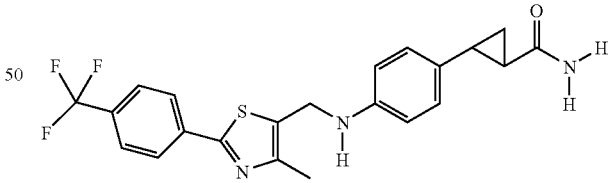

Racemic-(trans)-2-{4-[({4-methyl-2-[4-(trifluoromethyl)phenyl]-1,3-thiazol-5-yl}methyl)amino]phenyl}cyclopropanecarboxamide (IV-9)

HATU (0.393 g, 1.03 mmol) was added to a solution of racemic-(trans)-2-[4-({[4-Methyl-2-(4-methylphenyl)-1,3-thiazol-5-yl]methyl}amino)phenyl]cyclopropanecarboxylic acid (I-2m) (0.300 g, 0.69 mmol) in 8 mL of N,N-dimethylformamide. The solution was stirred at room temperature for 10 minutes and 0.5 mL of 30% ammonium hydroxide was added. Stirring was continued for 30 minutes. The reaction mixture was diluted with ethyl acetate and saturated aqueous sodium bicarbonate. The organic phase was separated, washed with water and brine and dried over anhydrous sodium sulfate. The solvent was evaporated and the residue was stirred with 1:1 hexane:ethyl acetate. The mixture was filtered to collect the title compound as a white solid (0.175 g, 59% yield). $^1$H NMR (400 MHz, DMSO-$d_6$) δ 8.01 (d, J=8.05 Hz, 2H), 7.78 (d, J=8.23 Hz, 2H), 7.48 (br s, 1H), 6.83 (d, J=8.60 Hz, 2H), 6.52 (d, J=8.60 Hz, 2H), 6.22 (m, 1H), 4.40 (d, J=5.85 Hz, 2H), 3.31 (s, 1H), 2.49 (s, 3H), 2.02 (m, 1H), 1.61 (m, 1H), 1.17 (m, 1H), 1.01 (m, 1H). ES-MS m/z 432 (MH+).

Example 44

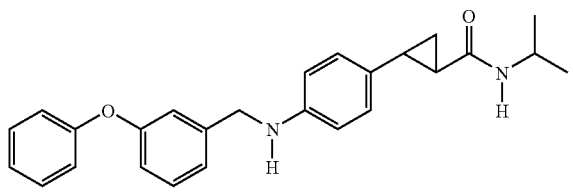

(+)-(trans)-N-(1-methylethyl)-2-[4-({[3-(phenyloxy)phenyl]methyl}amino)phenyl]cyclopropanecarboxamide (IV-10)

HATU (0.159 g, 0.42 mmol) was added to a solution of (+)-(trans)-2-{4-[(3-phenoxybenzyl)amino]phenyl}cyclopropanecarboxylic acid (III-3b) (0.100 g, 0.28 mmol) in 3 ml of N,N-dimethylformamide. The mixture was stirred at room temperature for 10 minutes and 0.059 mL (0.69 mmol) of isopropylamine was added. After stirring at room temperature for 15 minutes, the reaction mixture was diluted with water and extracted with ethyl acetate. The organic phase was washed with water and brine, dried over anhydrous sodium sulfate and concentrated. Chromatography on silica gel with hexane:ethyl acetate gave 0.068 g (61% yield) of the title compound as a white powder. NMR (400 MHz, CDCl$_3$) δ 7.32 (d, J=8.61 Hz, 2H), 7.28 (d, J=8.6 Hz, 2H), 7.10 (t, J=8.42 Hz, 1H), 7.00 (m, 1H), 6.97 (d, J=6.59 Hz, 2H), 6.89 (d, J=8.61 Hz, 2H), 6.87 (m, 1H), 6.52 (d, J=8.61 Hz, 2H), 5.37 (d, J=7.51 Hz, 1H), 4.27 (s, 2H), 4.10 (septet, J=6.59 Hz, 1H), 4.00 (br s, 1H), 2.36 (m, 1H), 1.52 (m, 1H), 1.40 (m, 1H), 1.15 (d, J=4.21 Hz, 3H), 1.14 (d, J=4.40 Hz, 3H), 1.10 (m, 1H). ES-MS m/z 401 (M-H)$^+$. [α]$^{25,D}$=+183° (chloroform, c=1.5).

Example 45

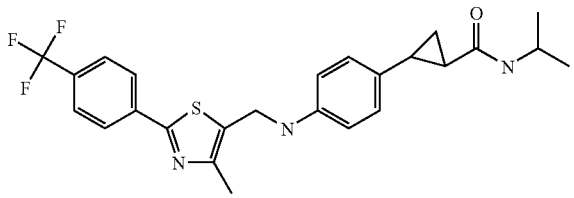

Racemic-(trans)-N-isopropyl-2-{4-[({4-methyl-2-[4-(trifluoromethyl)phenyl]-1,3-thiazol-5-yl}methyl)amino]phenyl}cyclopropanecarboxamide (IV-12)

To a mixture of racemic-(trans)-2-{4-[({4-methyl-2-[4-(trifluoromethyl)phenyl]-1,3-thiazol-5-yl}methyl)amino]phenyl}cyclopropanecarboxylic acid (I-2m) (0.10 g, 0.231 mmol) in dichloromethane (2 mL) and DMF (1 mL) was added HATU (0.13 g, 0.346 mmol). The mixture was stirred for 15 mins followed by addition of isopropylamine (0.04 g, 0.693 mmol). The solution stirred for 6 h after which the dichloromethane was removed via rotavap. Sat. NaHCO$_3$ and ethyl acetate were added and the organic layer separated and washed with H$_2$O, dried over MgSO$_4$, filtered and concentrated. The resulting oil was triterated with Et$_2$O and formed a yellow ppt which was filtered and dried under high vacuum to give the title compound as a yellow powder (0.062 g, 60%). $^1$H NMR (400 MHz, CDCl$_3$) δ 7.98 (d, J=8.2 Hz, 2H), 7.66 (d, J=8.1 Hz, 2H), 6.96 (d, J=8.1 Hz, 2H), 6.59 (d, J=8.4 Hz, 2H), 5.29 (d, J=7.8 Hz, 1H), 4.45 (s, 2H), 4.15-4.08 (m, 1H), 4.06 (s, 1H), 2.49 (s, 3H), 2.42-2.34 (m, 1H), 1.54-1.51 (m, 1H), 1.44-1.39 (m, 1H), 1.53-1.10 (m, 7H).

Example 46

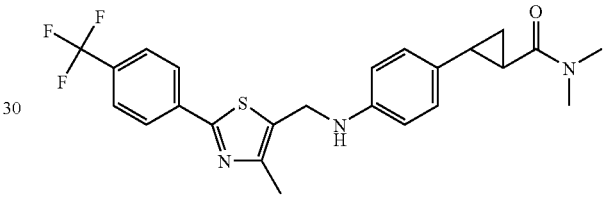

Racemic-(trans)-N,N-dimethyl-2-{4-[({4-methyl-2-[4-(trifluoromethyl)phenyl]-1,3-thiazol-5-yl}methyl)amino]phenyl}cyclopropanecarboxamide (IV-13)

To a mixture of racemic-(trans)-2-{4-[({4-methyl-2-[4-(trifluoromethyl)phenyl]-1,3-thiazol-5-yl}methyl)amino]phenyl}cyclopropanecarboxylic acid (I-2m) (0.10 g, 0.231 mmol)

in dichloromethane (2 mL) and DMF (1 mL) was added HATU (0.13 g, 0.346 mmol). The mixture was stirred for 15 mins followed by addition of dimethylamine (0.03 g, 0.693 mmol). The solution stirred for 6 h after which the dichloromethane was removed via rotavap. Sat. NaHCO$_3$ and ethyl acetate were added and the organic layer separated and washed with H$_2$O, dried over MgSO$_4$, filtered and concentrated. The resulting oil was triterated with Et$_2$O and formed a yellow ppt which was filtered and dried under high vacuum to give the title compound as a yellow powder (0.037 g, 37%). $^1$H NMR (400 MHz, CDCl$_3$) δ 7.97 (d, J=8.2 Hz, 2H), 7.65 (d, J=8.2 Hz, 2H), 6.99 (d, J=8.4 Hz, 2H), 6.61 (d, J=8.4 Hz, 2H), 4.3 (s, 2H), 4.1 (s, 1H), 3.13 (s, 3H), 2.97 (s, 3H), 2.48 (s, 3H), 2.42-2.37 (m, 1H), 1.90-1.86 (m, 1H), 1.58-1.53 (m, 1H), 1.22-1.15 (m, 1H).

Example 47

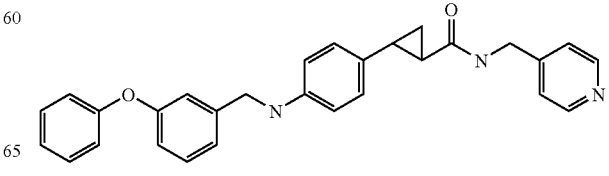

Racemic-(trans)-2-[4-({[3-(phenyloxy)phenyl]methyl}amino)phenyl]-N-(4-pyridinylmethyl)cyclopropanecarboxamide (IV-14)

To a mixture of racemic-(trans)-2-{4-[(3-phenoxybenzyl)amino]phenyl}cyclopropanecarboxylic acid (I-2a) (0.10 g, 0.231 mmol) in dichloromethane (2 mL) and DMF (3 mL) was added HATU (0.27 g, 0.71 mmol). The mixture was stirred for 15 min followed by addition of 4-(aminomethyl)pyridine (0.10 g, 0.94 mmol). The solution stirred for 6 h after which the dichloromethane was removed via rotavap. Sat. NaHCO$_3$ and ethyl acetate were added and the organic layer separated and washed with H$_2$O, dried over MgSO$_4$, filtered and concentrated. The resulting oil was triterated with Et$_2$O and formed a cream ppt which was filtered and dried under high vacuum to give the title compound as a cream powder (0.08 g, 40%). $^1$H NMR (400 MHz, CDCl$_3$) δ 8.56 (d, J=5.4 Hz, 2H), 7.34-7.28 (m, 3H), 7.26 (d, J=5.5 Hz, 2H), 7.11-7.07 (m, 2H), 7.01-6.99 (m, 3H), 6.92-6.90 (m, 3H), 6.55 (d, J=8.4 Hz, 2H), 6.01-5.98 (m, 1H), 4.50-4.47 (m, 2H), 4.29 (s, 2H), 4.03 (s, 1H), 2.48-2.43 (m, 1H), 1.58-1.51 (m, 1H), 1.24-1.19 (m, 2H). ES-MS m/z 450 (MH+).

Example 48

Racemic-(trans)-2-{4-[(3-phenoxybenzyl)amino]phenyl}-N-[4-(trifluoromethyl)benzyl]cyclopropanecarboxamide (IV-16)

To a mixture of racemic-(trans)-2-{4-[(3-phenoxybenzyl)amino]phenyl}cyclopropanecarboxylic acid (I-2a) (0.15 g, 0.41 mmol) in dichloromethane (3 mL) and DMF (1 mL) was added HATU (0.23 g, 0.62 mmol). The mixture was stirred for 15 min followed by addition of 4-trifluoromethylbenzylamine (0.14 g, 0.82 mmol). The solution stirred for 6 h after which the dichloromethane was removed via rotavap. Sat. NaHCO$_3$ and ethyl acetate were added and the organic layer separated and washed with H$_2$O, dried over MgSO$_4$, filtered and concentrated. The resulting oil was triterated with Et$_2$O and formed a white ppt which was filtered and dried under high vacuum to give the title compound as a white powder (0.08 g, 38%). $^1$H NMR (400 MHz, CDCl$_3$) δ 7.66 (d, J=8.1 Hz, 1H), 7.60 (d, J=8 Hz, 1H), 7.45-7.41 (m, 3H), 7.39-7.26 (m, 3H), 7.11-7.07 (m, 2H), 7.01-6.97 (m, 2H), 6.92-6.89 (m, 3H), 6.54 (d, J=8.4 Hz, 2H), 6.21 (s, 1H), 5.93 (s, 1H),

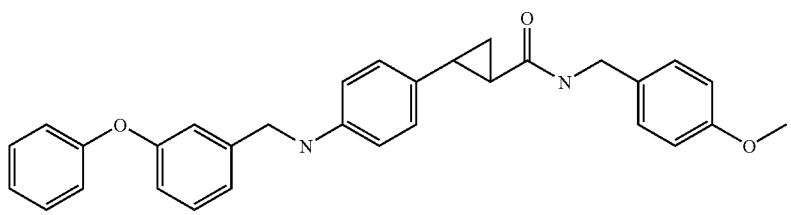

Racemic-(trans)-N-(4-methoxybenzyl)-2-{4-[(3-phenoxybenzyl)amino]phenyl}cyclopropanecarboxamide (IV-15)

To a mixture of racemic-(trans)-2-{4-[(3-phenoxybenzyl)amino]phenyl}cyclopropanecarboxylic acid (I-2a) (0.14 g, 0.40 mmol) in dichloromethane (3 mL) and DMF (1 mL) was added HATU (0.23 g, 0.60 mmol). The mixture was stirred for 15 min followed by addition of 4-methoxybenzylamine (0.96 g, 0.80 mmol). The solution stirred for 6 h after which the dichloromethane was removed via rotavap. Sat. NaHCO$_3$ and ethyl acetate were added and the organic layer separated and washed with H$_2$O, dried over MgSO$_4$, filtered and concentrated. The resulting oil was triterated with Et$_2$O and formed a white ppt which was filtered and dried under high vacuum to give the title compound as a white powder (0.12 g, 62%). $^1$H NMR (400 MHz, CDCl$_3$) δ 7.34-7.25 (m, 6H), 7.19-7.07 (m, 5H), 6.99 (t, J=7.9 Hz, 2H), 6.91 (t, J=8.3 Hz, 2H), 6.54 (d, J=8.4 Hz, 2H), 5.78 (s, 1H), 4.42-4.40 (m, 2H); 4.28 (s, 2H), 4.00 (s, 1H), 2.46-2.42 (m, 1H), 2.34 (s, 3H), 1.60-1.55 (m, 1H), 1.48-1.44 (m, 1H), 1.21-1.14 (m, 1H).

Example 49

4.54-4.46 (m, 2H), 4.29 (s, 2H), 2.46-2.42 (m, 1H), 1.61-1.49 (m, 2H), 1.22-1.18 (m, 1H). ES-MS m/z 517 (MH+).

Example 50

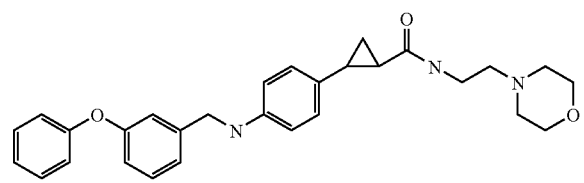

Racemic-(trans)-N-(2-morpholin-4-ylethyl)-2-{4-[(3-phenoxybenzyl)amino]phenyl}cyclopropanecarboxamide (IV-17)

To a mixture of racemic-(trans)-2-{4-[(3-phenoxybenzyl)amino]phenyl}cyclopropanecarboxylic acid (I-2a) (0.13 g,

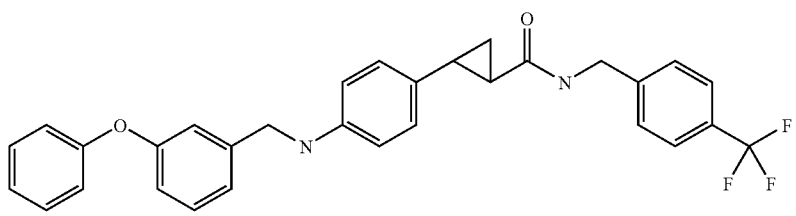

0.36 mmol) in dichloromethane (1 mL) and DMF (3 mL) was added HATU (0.20 g, 0.53 mmol). The mixture was stirred for 15 min followed by addition of 4(-2-aminoethylmorpholine) (0.09 g, 0.71 mmol). The solution stirred for 6 h after which the dichloromethane was removed via rotavap. Sat. NaHCO$_3$ and ethyl acetate were added and the organic layer separated and washed with H$_2$O, dried over MgSO$_4$, filtered and concentrated. The resulting oil was triterated with Et$_2$O and formed a white ppt which was filtered and dried under high vacuum to give the title compound as a white powder (0.07 g, 42%). $^1$H NMR (400 MHz, CDCl$_3$) δ 7.34-7.30 (m, 3H), 7.12 (t, J=7.5 Hz, 2H), 7.02 (t, J=7.9 Hz, 3H), 6.92 (t, J=8.4 Hz, 3H), 6.55 (d, J=8.5 Hz, 2H), 6.20 (s, 1H), 4.30 (s, 2H), 3.72-3.70 (m, 4H), 3.41-3.37 (m, 2H), 2.51-2.47 (m, 4H), 2.41-2.37 (m, 1H), 1.60-1.50 (m, 4H), 1.19-1.15 (m, 1H).

Example 51

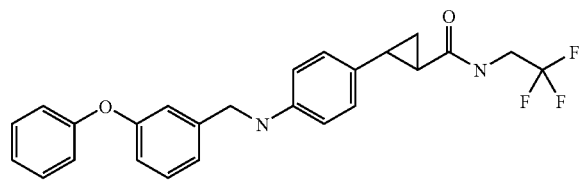

Racemic-(trans)-2-{4-[(3-phenoxybenzyl)amino]phenyl}-N-(2,2,2-trifluoroethyl)cyclopropanecarboxamide (IV-18)

To a mixture of racemic-(trans)-2-{4-[(3-phenoxybenzyl)amino]phenyl}cyclopropanecarboxylic acid (I-2a) (0.15 g, 0.41 mmol) in dichloromethane (3 mL) and DMF (1 mL) was added HATU (0.23 g, 0.62 mmol). The mixture was stirred for 15 mins followed by addition of 2,2,2-trifluoroethylamine (0.08 g, 0.82 mmol). The solution stirred for 6 h after which the dichloromethane was removed via rotavap. Sat. NaHCO$_3$ and ethyl acetate were added and the organic layer separated and washed with H$_2$O, dried over MgSO$_4$, filtered and concentrated. The resulting oil was triterated with Et$_2$O and formed a white ppt which was filtered and dried under high vacuum to give the title compound as a white powder (0.109, 55%). $^1$H NMR (400 MHz, CDCl$_3$) δ7.34-7.25 (m, 3H), 7.12 (t, J=7.5 Hz, 2H), 7.01 (t, J=7.7 Hz, 3H), 6.91 (t, J=8.4 Hz, 3H), 6.54 (d, J=8.4 Hz, 2H), 5.81 (s, 1H), 4.29 (s, 2H), 4.01-3.88 (m, 3H), 2.48-2.43 (m, 1H), 1.62-1.49 (m, 2H), 1.27-1.20 (m, 1H).

Example 52

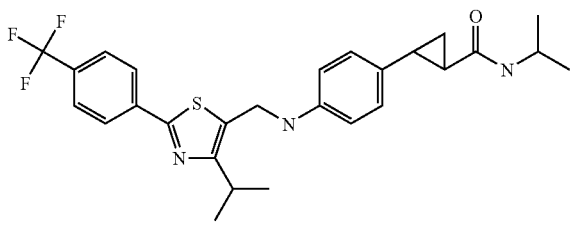

Racemic-(trans)-N-isopropyl-2-{4-[({4-isopropyl-2-[4-(trifluoromethyl)phenyl]-1,3-thiazol-5-yl}methyl)amino]phenyl}cyclopropanecarboxamide (IV-19)

To a mixture of racemic-(trans)-2-{4-[({4-isopropyl-2-[4-(trifluoromethyl)phenyl]-1,3-thiazol-5-yl}methyl)amino]phenyl}cyclopropanecarboxylic acid (I-2n) (0.05 g, 0.11 mmol) in dichloromethane (3 mL) and DMF (1 mL) was added HATU (0.06 g, 0.16 mmol). The mixture was stirred for 15 min followed by addition of isopropylamine (0.01 g, 0.16 mmol). The solution stirred for 3 h after which the dichloromethane was removed via rotavap. Sat. NaHCO$_3$ and ethyl acetate were added and the organic layer separated and washed with H$_2$O, dried over MgSO$_4$, filtered and concentrated. The resulting oil was triterated with Et$_2$O and formed a white ppt which was filtered and dried under high vacuum to give the title compound as a white powder (0.01 g, 22%). $^1$H NMR (400 MHz, CDCl$_3$) δ 7.99 (d, 8.3 Hz, 2H), 7.63 (d, J=8.2 Hz, 2H), 6.94 (d, J=8.4 Hz, 2H), 6.60 (d, J=8.5 Hz, 2H), 5.37 (d, J=7.9 Hz, 1H), 4.45 (s, 2H), 4.10-4.08 (m, 1H), 3.93 (s, 1H), 3.16-3.13 (m, 1H), 2.39-2.37 (m, 1H), 1.54-1.50 (m, 1H), 1.42-1.39 (m, 1H), 1.35 (d, J=6.8 Hz, 6H), 1.15-1.09 (m, 7H).

Example 53

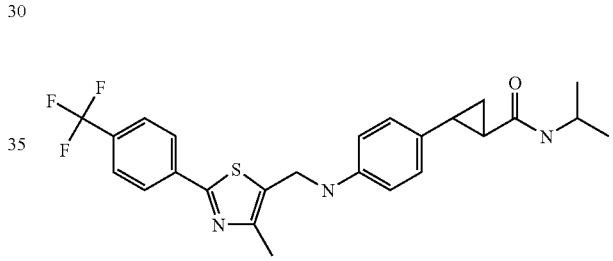

Enantiomerically Enriched N-isopropyl-2-{4-[({4-methyl-2-[4-(trifluoromethyl)phenyl]-1,3-thiazol-5-yl}methyl)amino]phenyl}cyclopropanecarboxamide (IV-20)

To a mixture of (+)-(trans)-2-{4-[({4-methyl-2-[4-(trifluoromethyl)phenyl]-1,3-thiazol-5-yl}methyl)amino]phenyl}cyclopropanecarboxylic acid (III-3c) (0.12 g, 0.28 mmol) in dichloromethane (2 mL) and DMF (1 mL) was added HATU (0.16 g, 0.42 mmol). The mixture was stirred for 15 min followed by addition of isopropylamine (0.02 g, 0.33 mmol). The solution stirred for 6 h after which the dichloromethane was removed via rotavap. Sat. NaHCO$_3$ and ethyl acetate were added and the organic layer separated and washed with H$_2$O, dried over MgSO$_4$, filtered and concentrated. The resulting oil was triterated with Et$_2$O and formed a yellow ppt which was filtered and dried under high vacuum to give the title compound as a yellow powder (0.08 g, 61%). $^1$H NMR (400 MHz, CDCl$_3$) δ 7.97 (d, J=8.3 Hz, 2H), 7.65 (d, J=8.2 Hz, 2H), 6.95 (d, J=8.4 Hz, 2H), 6.59 (d, J=8.4 Hz, 2H), 5.49 (d, J=7.9 Hz, 1H), 4.44 (s, 2H), 4.13-4.08 (m, 1H), 2.49 (s, 3H), 2.40-2.37 (m, 1H), 1.56-1.51 (m, 1H), 1.44-1.39 (m, 1H), 1.26-1.10 (m, 7H). ES-MS m/z 474.2 (MH+).

Example 54

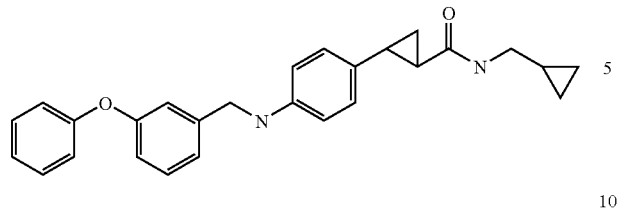

Enantiomerically Enriched N-(cyclopropylmethyl)-2-{4-[(3-phenoxybenzyl)amino]phenyl}cyclopropanecarboxamide (IV-21)

To a mixture of (+)-(trans)-2-{4-[(3-phenoxybenzyl)amino]phenyl}cyclopropanecarboxylic acid (III-3b) (0.09 g, 0.25 mmol) in dichloromethane (2 mL) and DMF (1 mL) was added HATU (0.14 g, 0.37 mmol). The mixture was stirred for 15 min followed by addition of aminomethylcyclopropane (0.03 g, 0.37 mmol). The solution stirred for 4 h after which the dichloromethane was removed via rotavap. Sat. NaHCO₃ and ethyl acetate were added and the organic layer separated and washed with H₂O, dried over MgSO₄, filtered and concentrated. The crude material was purified on silica gel eluting with an increasing gradient from hexanes to 30% ethyl acetate/hexanes to give the title compound as a white powder (0.01 g, 11%). 1H NMR (400 MHz, CDCl₃) δ 7.34-7.28 (m, 3H), 7.10-7.08 (m, 2H), 7.02-6.98 (m, 3H), 6.92-6.89 (m, 3H), 6.55 (d, J=8.3 Hz, 2H), 5.68 (s, 1H), 4.29 (s, 2H), 4.01 (s, 1H), 3.15-3.12 (m, 2H), 2.39 (s, 1H), 1.57-1.46 (m, 2H), 1.17-1.14 (m, 1H), 0.95 (s, 1H), 0.51 (d, J=7.7 Hz, 2H), 0.20 (d, J=4.6 Hz, 2H). ES-MS m/z 413.3 (MH+).

Intermediates:

Scheme V:

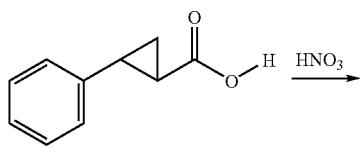

V-1
racemic-trans-2-phenyl cyclopropanecarboxylic acid

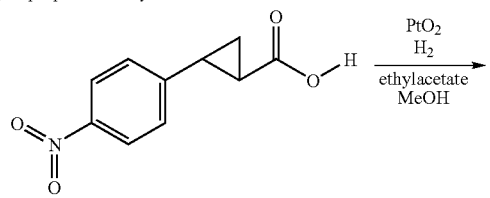

V-2

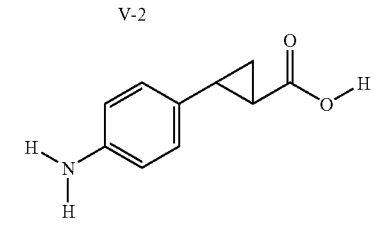

I-1
Synthesis of racemic-(trans)-2-(4-aminophenyl)cyclopropanecarboxylic acid (I-1)

Intermediate Example A

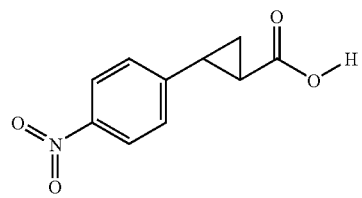

Racemic-(trans)-2-(4-nitrophenyl)cyclopropanecarboxylic Acid (V-2)

The description in U.S. Pat. No. 4,331,683 is herein incorporated by reference with regard to Intermediate Example A.

2-phenylcyclopropanecarboxylic acid (V-1) (8.00 g, 49.4 mmol) was added as a solid in portions over 20 min to concentrated nitric acid at RT. After 3 h a fine precipitate has formed and the reaction was cooled to ca. 10° C. The solid was filtered and dried, then partially dissolved in hot xylenes (350 mL). The mixture was allowed to cool to RT then the solid was filtered to give the title compound as a white powder (3.00 g, 29%). ¹H NMR (400 MHz, DMSO) δ12.45 (s, 1H), 8.10 (d, J=8.7 Hz, 2H), 7.44 (d, J=8.9 Hz, 2H), 2.58-2.53 (m, 1H), 1.99-1.95 (m, 1H), 1.55-1.50 (m, 1H), 1.47-1.42 (m, 1H).

Intermediate Example B

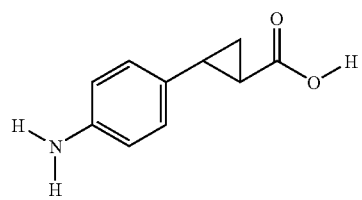

Racemic-(trans)-2-(4-aminophenyl)cyclopropanecarboxylic Acid (I-1)

A Fischer-Porter bottle containing racemic-(trans)-2-(4-nitrophenyl)cyclopropanecarboxylic acid (V-2) (4.60 g, 22.22 mmol), PtO₂ (0.16 g, 0.70 mmol), ethyl acetate (70 mL) and MeOH (50 mL) was purged with N₂ (3x's) then charged with 40 psig H₂ at RT. After 1 h, the bottle was carefully vented and the suspension was filtered through Celite. The solution was concentrated to give the title compound as a white powder (4.01 g, ~100%). ¹H NMR (400 MHz, DMSO) δ 6.79 (d, J=8.6 Hz, 2H), 6.47 (d, J=8.6, 2H), 5.02 (bs, 2H), 2.21-2.16 (m, 1H), 1.61-1.56 (m, 1H), 1.31-1.28 (m, 1H), 1.19-1.14 (m, 1H). ES-MS m/z 176.3 (MH−).

Scheme VII:

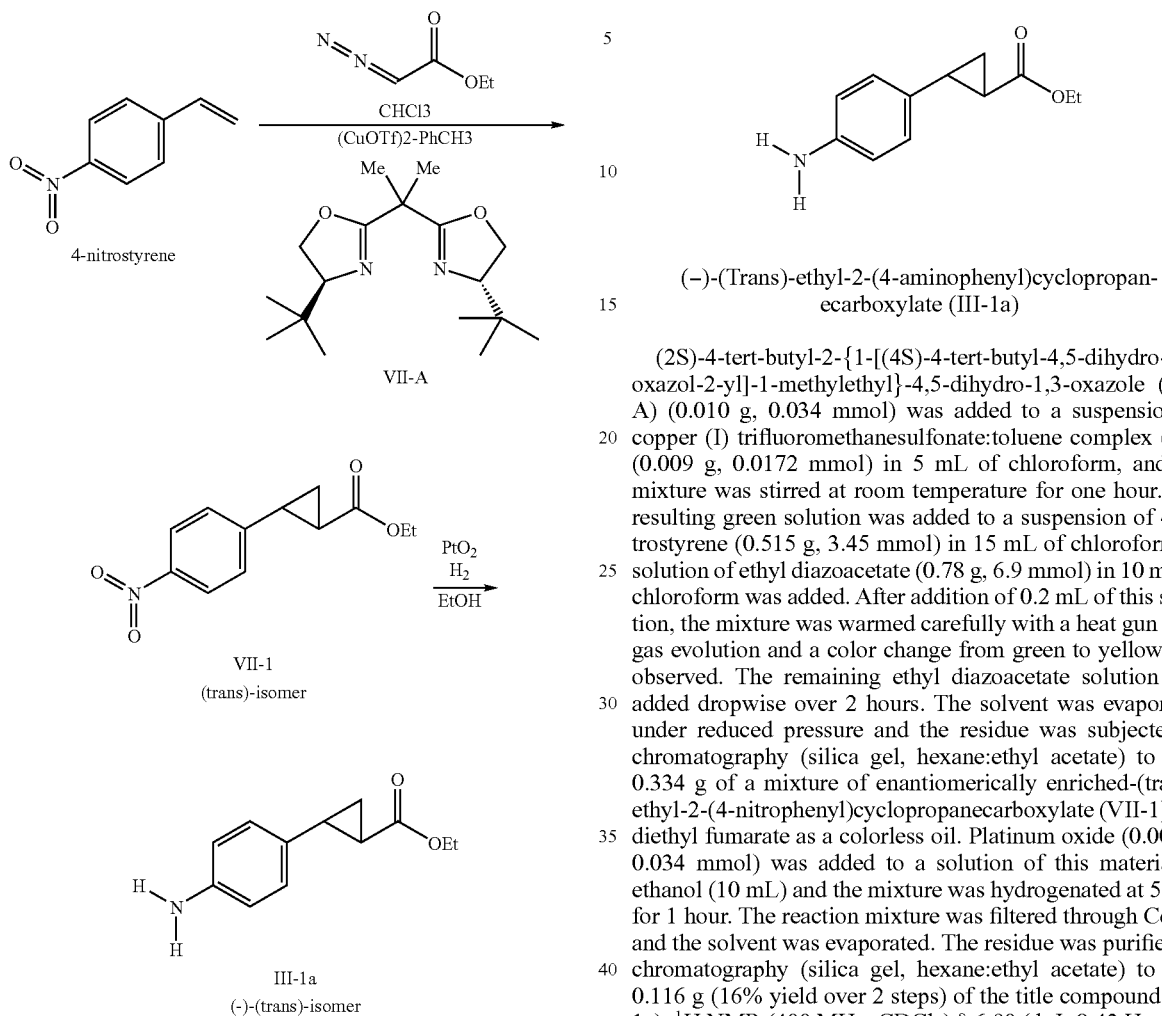

Synthesis of (-)-(trans)-ethyl-2-(4-aminophenyl)cyclopropanecarboxylate (III-1a)

Intermediate Example G

(−)-(Trans)-ethyl-2-(4-aminophenyl)cyclopropanecarboxylate (III-1a)

(2S)-4-tert-butyl-2-{1-[(4S)-4-tert-butyl-4,5-dihydro-1,3-oxazol-2-yl]-1-methylethyl}-4,5-dihydro-1,3-oxazole (VII-A) (0.010 g, 0.034 mmol) was added to a suspension of copper (I) trifluoromethanesulfonate:toluene complex (2:1) (0.009 g, 0.0172 mmol) in 5 mL of chloroform, and the mixture was stirred at room temperature for one hour. The resulting green solution was added to a suspension of 4-nitrostyrene (0.515 g, 3.45 mmol) in 15 mL of chloroform. A solution of ethyl diazoacetate (0.78 g, 6.9 mmol) in 10 mL of chloroform was added. After addition of 0.2 mL of this solution, the mixture was warmed carefully with a heat gun until gas evolution and a color change from green to yellow was observed. The remaining ethyl diazoacetate solution was added dropwise over 2 hours. The solvent was evaporated under reduced pressure and the residue was subjected to chromatography (silica gel, hexane:ethyl acetate) to give 0.334 g of a mixture of enantiomerically enriched-(trans)-ethyl-2-(4-nitrophenyl)cyclopropanecarboxylate (VII-1) and diethyl fumarate as a colorless oil. Platinum oxide (0.008 g, 0.034 mmol) was added to a solution of this material in ethanol (10 mL) and the mixture was hydrogenated at 50 psi for 1 hour. The reaction mixture was filtered through Celite, and the solvent was evaporated. The residue was purified by chromatography (silica gel, hexane:ethyl acetate) to give 0.116 g (16% yield over 2 steps) of the title compound (III-1a). $^1$H NMR (400 MHz, CDCl$_3$) δ 6.90 (d, J=8.42 Hz, 2H), 6.60 (d, J=8.42 Hz, 2H), 4.15 (q, J=7.14 Hz, 2H), 3.62 (br s, 2H), 2.44 (m, 1H), 1.80 (m, 1H), 1.52 (m, 1H), 1.27 (t, J=7.14 Hz, 3H), 1.23 (m, 1H).

Scheme VIII:
Route A:

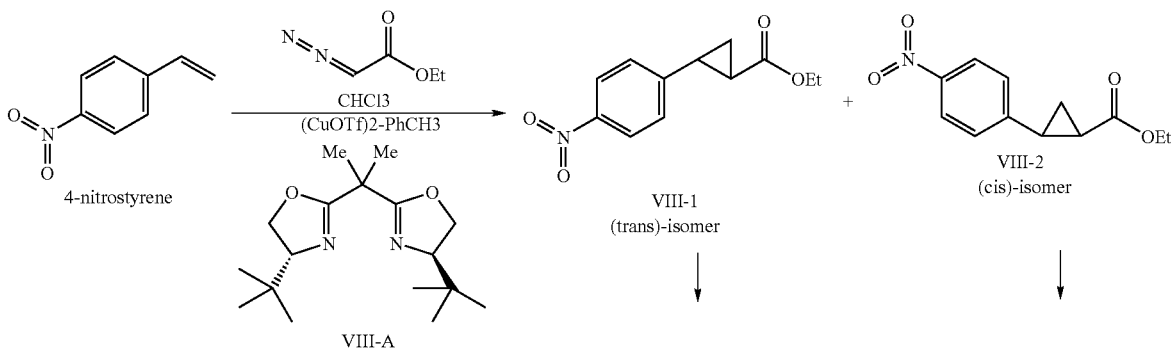

-continued

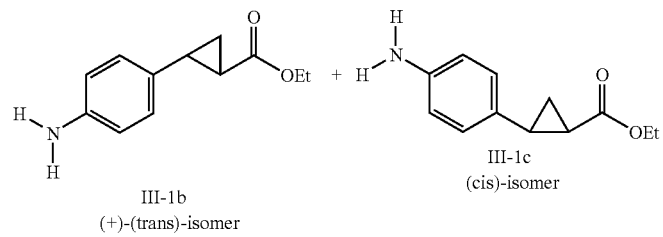

Synthesis of (+)-(trans)-ethyl-2-(4-aminophenyl) cyclopropanecarboxylate (III-1b) & (cis)-isomer (III-1c)

Intermediate Example Hi

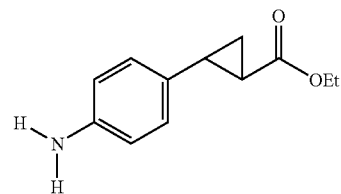

(+)-(Trans)-ethyl-2-(4-aminophenyl)cyclopropanecarboxylate (III-1b)

Route A (2R)-4-tert-butyl-2-{1-[(4R)-4-tert-butyl-4,5-dihydro-1,3-oxazol-2-yl]-1-methylethyl}-4,5-dihydro-1,3-oxazole (VIII-A) (0.197 g, 0.671 mmol), prepared as described by Evans et al., J. Am. Chem. Soc. 1991, 113, 726-728, was added to a suspension of copper (I) trifluoromethanesulfonate:toluene complex (2:1) (0.173 g, 0.335 mmol) in 20 mL of chloroform, and the mixture was stirred for one hour at room temperature. The resulting green solution was added to a suspension of 4-nitrostyrene (10.0 g, 67.1 mmol) in 150 mL of chloroform. A solution of ethyl diazoacetate (15.4 mL, 62.8 mmol) in 150 mL of chloroform was added. After addition of 1 mL of this solution, the mixture was warmed carefully with a heat gun until gas evolution and a color change from green to yellow was observed. The remaining ethyl diazoacetate solution was added dropwise over 2.5 hours. The solvent was evaporated under reduced pressure and the crude residue (ca. 4:1 mixture of trans-isomer VIII-1/cis-isomer VIII-2) was subjected to flash chromatography (silica gel, hexane:ethyl acetate) to give 6.37 g of a mixture of enantiomerically enriched-(trans)-ethyl-2-(4-nitrophenyl)cyclopropanecarboxylate and diethyl fumarate as a yellow oil. Platinum oxide (0.27 g, 1.2 mmol) was added to a solution of this material in ethanol (100 mL) and the mixture was hydrogenated at 50 psi for 1 hr. The reaction mixture was filtered through Celite, and the solvent was evaporated. The residue was purified by chromatography (silica gel, hexane:ethyl acetate) to give 4.06 g (29.5% yield over two steps) of pure (+)-(trans)-ethyl-2-(4-aminophenyl)cyclopropanecarboxylate (III-1b) as a colorless oil. $^1$H NMR (400 MHz, CDCl$_3$) δ 6.90 (d, J=8.61 Hz, 2H), 6.60 (d, J=8.42 Hz, 2H), 4.15 (q, J=7.14 Hz, 2H), 3.60 (br s, 2H), 2.43 (m, 1H), 1.77 (m, 1H), 1.50 (m, 1H), 1.27 (t, J=7.69 Hz, 3H), 1.24 (m, 1H). $[\alpha]^{25}_D$=+296° (CHCl$_3$, c=5.7). The product was determined to be 97% ee by chiral SFC according to Method 3.

Scheme VIII, Route B:

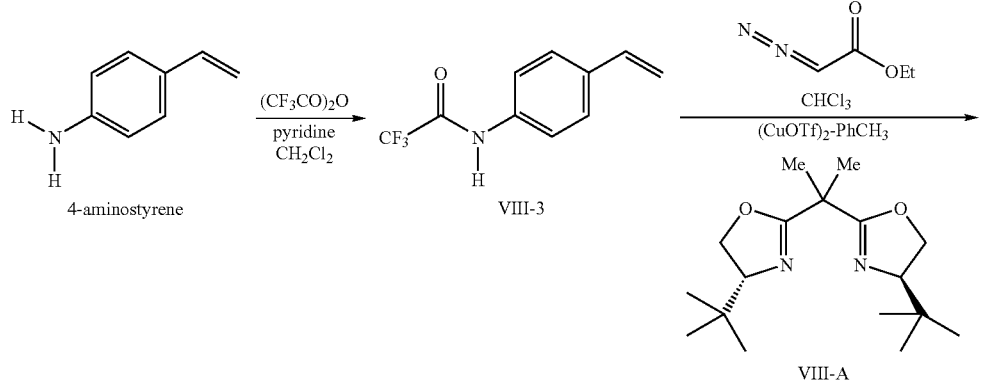

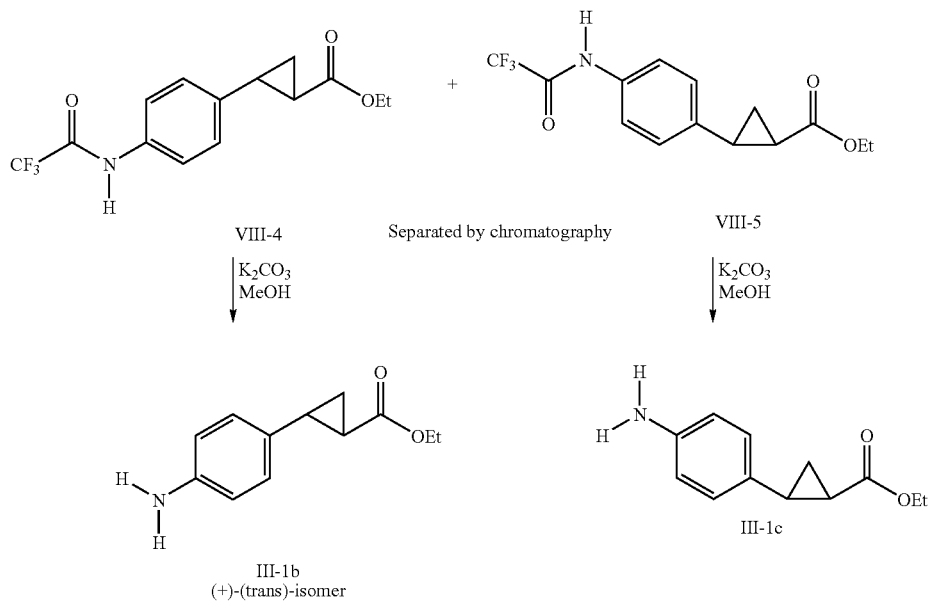

Intermediate Example Hii

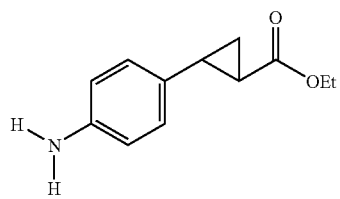

(+)-(Trans)-ethyl-2-(4-aminophenyl)cyclopropanecarboxylate (III-1b)

Trifluoroacetic anhydride (10.3 mL, 73.9 mmol) was added to a solution of 4-aminostyrene (8.00 g, 67.2 mmol) and pyridine (8.1 mL, 100.8 mmol) in 100 mL of dichloromethane at 0° C. The reaction mixture was diluted with dichloromethane and washed with 1N aqueous hydrochloric acid, dried over anhydrous sodium sulfate, concentrated under vacuum and purified by chromatography (silica gel, hexane:ethyl acetate) to give 10.89 g (75%) of 2,2,2-trifluoro-N-(4-vinylphenyl)acetamide (VIII-3) as a white solid. $^1$H NMR (400 MHz, CDCl$_3$) δ 7.85 (br s, 1H), 7.52 (d, J=8.61 Hz, 2H), 7.42 (d, J=8.61 Hz, 2H), 6.67 (dd, J=10.99 Hz, 17.58 Hz, 1H), 5.73 (d, J=17.58 Hz, 1H), 5.27 (d, J=10.80 Hz, 1H). (2R)-4-tert-Butyl-2-{1-[(4R)-4-tert-butyl-4,5-dihydro-1,3-oxazol-2-yl]-1-methylethyl}-4,5-dihydro-1,3-oxazole (VIII-A) (0.147 g, 0.501 mmol) prepared as described by Evans et al., J. Am. Chem. Soc. 1991, 113, 726-728, was added to a suspension of copper (I) trifluormethanesulfonate-toluene complex (2:1) in 15 mL of chloroform at room temperature. After 1.5 hours the mixture was added to a solution of 2,2,2-trifluoro-N-(4-vinylphenyl)acetamide (10.77 g, 50.1 mmol) in 200 mL of chloroform. A small amount (2-3 mL) of a solution of ethyl diazoacetate (7.8 mL, 74.1 mmol) in 100 mL of chloroform was added. The mixture was carefully warmed with a heat gun until gas evolution and a color change from green to yellow occurred. The remaining ethyl diazoacetate solution was added dropwise over two hours. The solvent was evaporated. The crude product (~3:1 trans VIII-4/cis VIII-5) was dissolved in 150 mL of methanol and potassium carbonate (13.8 g, 100.2 mmol) and 50 mL of water were added. The mixture was stirred at room temperature overnight. Methanol was evaporated and the residue was extracted between dichloromethane and water. The organic phase was evaporated and the residue was purified by chromatography on silica gel with an ethyl acetate gradient (5 to 30%) in hexanes to give 1.02 g (10% yield) of the title compound as a yellow oil. $^1$H NMR (400 MHz, CDCl$_3$) δ 6.89 (d, J=8.24 Hz, 2H), 6.59 (d, J=8.42 Hz, 2H), 4.14 (quartet, J=7.14 Hz, 2H), 3.59 (br s, 2H), 2.41 (m, 1H), 1.75 (m, 1H), 1.50 (m, 1H), 1.26 (t, J=7.14 Hz, 3H), 1.21 (m, 1H).

Intermediate Example Hiii

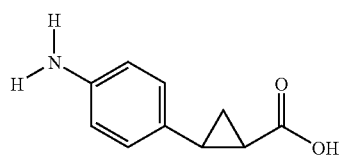

Enantiomerically Enriched-(cis)-ethyl-2-(4-aminophenyl)cyclopropanecarboxylate (III-1c)

The title compound (0.54 g) was obtained as a by-product. $^1$H NMR (400 MHz, CDCl$_3$) δ 7.03 (d, J=7.87 Hz, 2H), 6.57 (d, J=8.12 Hz, 2H), 3.87 (q, J=7.14 Hz, 2H), 3.56 (br s, 2H), 2.45 (m, 1H), 1.96 (m, 1H), 1.60 (m, 1H), 1.25 (m, 1H) 1.01 (t, J=7.14 Hz, 3H).

Scheme IX:
Route A:

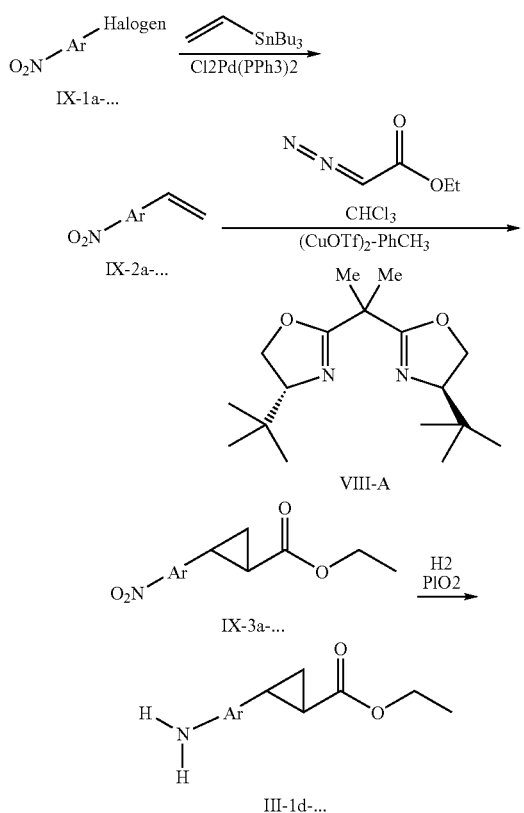

General synthesis of enantiomerically enriched-(trans)-ethyl-2-(4-amino-aryl)-cyclopropanecarboxylates (III-1d-...)

Intermediate Example I

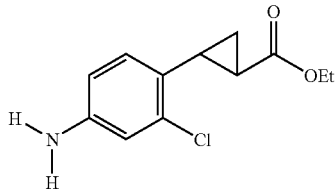

Enantiomerically Enriched-(trans)-ethyl 2-(4-amino-2-chlorophenyl)cyclopropanecarboxylate (III-1d)

A mixture of 1-bromo-2-chloro-4-nitrobenzene (IX-1a) (0.800 g, 3.38 mmol), dichlorobis(triphenylphosphine)palladium (II) (0.238 g, 0.34 mmol), and tributylvinyltin (1.60 g, 5.08 mmol) in 10 mL of N,N-dimethylformamide, in two reaction tubes sealed with septa, was heated in a microwave synthesizer to 150° C. for 15 minutes. The mixture was diluted with ethyl acetate and filtered through Celite. The filtrate was washed with water and brine, dried over anhydrous sodium sulfate and concentrated. Chromatography on silica gel with hexane:ethyl acetate gave 0.43 g of a 70:30 mixture of desired styrene product (IX-2a) and tributyltin bromide.

The partially purified product (IX-2a) was dissolved in 3 mL of chloroform and added to a mixture of copper (I) trifluoromethanesulfonate-toluene complex (2:1) (0.006 g, 0.012 mmol) and (2R)-4-tert-Butyl-2-{1-[(4R)-4-tert-butyl-4,5-dihydro-1,3-oxazol-2-yl]-1-methylethyl}-4,5-dihydro-1,3-oxazole (VIII-A) (0.007 g, 0.024 mmol) (prepared as described by Evans et al., J. Am. Chem. Soc. 1991, 113, 726-728) which had been stirred at room temperature for one hour. Approximately 0.1 mL of a solution of ethyl diazoacetate (0.58 g, 5.18 mmol) in 5 mL of chloroform was added and the mixture was carefully warmed with a heat gun until gas evolution and a color change from green to amber was observed. The rest of the ethyl diazoacetate solution was added dropwise over 1.5 hours. The solvent was evaporated and the residue subjected to chromatography on silica gel with hexane:ethyl acetate to give a mixture of desired product (IX-3a), diethyl fumarate and a small amount of cis isomer.

Platinum oxide (0.014 g, 0.063 mmol) was added to a solution of the partially purified product (IX-3a) in 10 mL of ethanol in a Fisher-Porter bottle. The mixture was degassed, flushed with nitrogen, degassed and filled with hydrogen (50 psi). After 45 minutes, the mixture was filtered through Celite. The filtrate was evaporated and the residue purified by chromatography on silica gel with hexane:ethyl acetate to give 0.198 g (24% yield over 3 steps) of enantiomerically enriched-(trans)-ethyl-2-(4-amino-2-chlorophenyl)cyclopropanecarboxylate (III-1d) as a yellow oil. 1HNMR (400 MHz, CDCl$_3$) δ 6.78 (d, J=8.24 Hz, 1H), 6.68 (d, J=2.38 Hz, 1H), 6.46 (dd, J=2.38 Hz, 8.24 Hz, 1H), 4.16 (q, J=7.14 Hz, 2H), 3.67 (br s, 2H), 2.58 (m, 1H), 1.68 (m, 1H), 1.52 (m, 1H), 1.27 (t, J=7.14 Hz, 3H), 1.22 (m, 1H).

Intermediate Example J

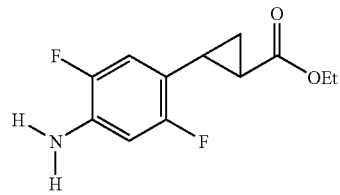

Enantiomerically Enriched-(trans)-ethyl 2-(4-amino-2,5-difluorophenyl)cyclopropanecarboxylate (III-1e)

A mixture of 1-bromo-2,5-difluoro-4-nitrobenzene (IX-1b) (0.800 g, 3.36 mmol), dichlorobis(triphenylphosphine) palladium (II) (0.238 g, 0.34 mmol), and tributylvinyltin (1.60 g, 5.08 mmol) in 10 mL of N,N-dimethylformamide, in two reaction tubes sealed with septa, was heated in a microwave synthesizer to 150° C. for 15 minutes. The mixture was diluted with ethyl acetate and filtered through Celite. The filtrate was washed with water and brine, dried over anhydrous sodium sulfate and concentrated. Chromatography on silica gel with hexane:ethyl acetate gave 0.657 g of a mixture of 2,5-difluoro-4-vinylaniline (IX-2b) and tributyltin bromide.

The partially purified product (IX-2b) was dissolved in 3 mL of chloroform and added to a mixture of copper(I) trifluoromethanesulfonate-toluene complex (2:1) (0.008 g, 0.016 mmol) and (2R)-4-tert-butyl-2-{1-[(4R)-4-tert-butyl-4,5-dihydro-1,3-oxazol-2-yl]-1-methylethyl}4,5-dihydro-1,3-oxazole (VIII-A) (0.010 g, 0.032 mmol) (prepared as described by Evans et al., J. Am. Chem. Soc. 1991, 113, 726-728) which had been stirred at room temperature for one hour. Approximately 0.1 mL of a solution of ethyl diazoacetate (0.80 g, 7.12 mmol) in 5 mL of chloroform was added and the mixture was carefully warmed with a heat gun until gas evolution and a color change was observed. The rest of the ethyl diazoacetate solution was added dropwise over 2 hours. The solvent was evaporated and the residue subjected to chromatography on silica gel with hexane:ethyl acetate to give a mixture of enantiomerically enriched-(trans)-ethyl-2-(2,5-difluoro-4-nitrophenyl)cyclopropanecarboxylate (major component) (IX-3b), diethyl fumarate and a small amount of the cis isomer.

Platinum oxide (0.013 g, 0.057 mmol) was added to a solution of (IX-3b) in 10 mL of ethanol in a Fisher-Porter bottle. After hydrogenation for 45 minutes at 50 psi, the mixture was filtered through Celite. The filtrate was evaporated and the residue purified by chromatography on silica gel with hexane:ethyl acetate to give 0.112 g (14% yield over 3 steps) of 90% pure title compound (III-1e). $^1$HNMR (400 MHz, CDCl$_3$) δ 6.57 (dd, J=6.77, 11.34 Hz, 1H), 6.44 (dd, J=7.50, 10.79 Hz, 1H), 4.15 (q, J=7.32 Hz, 2H), 3.74 (br s, 2H), 2.50 (m, 1H), 1.78 (m, 1H), 1.52 (m, 1H), 1.27 (t, J=7.14 Hz, 3H), 1.22 (m, 1H).

Scheme X:

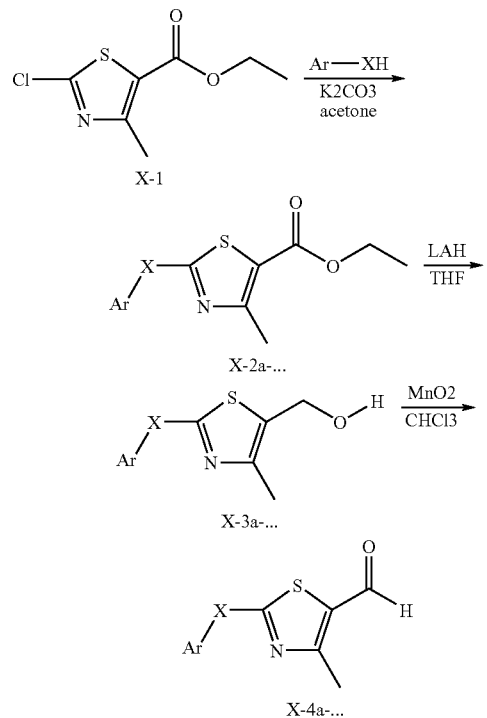

General synthesis of Thiazole Intermediates.

Intermediate Example K

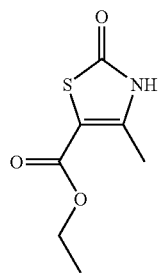

Ethyl 4-methyl-2-oxo-2,3-dihydro-1,3-thiazole-5-carboxylate

To a solution of ethyl-3-aminocrotanate (0.98 mL, 7.75 mmol) in chlorobenzene (4 mL) was added chlorocarbonylsulfenyl chloride (0.65 mL, 7.70 mmol) dropwise. The mixture was stirred at 100° C. for 3 h. Upon cooling, the mixture was concentrated. The crude material was purified by chromatography (EtOAc/hexanes) to give the title compound as a yellow solid (0.80 g, 55%). $^1$H NMR (400 MHz, CDCl$_3$) δ 10.28 (s, 1H), 4.27 (q, J=7.1 Hz, 2H), 2.48 (s, 3H), 1.32 (t, J=7.1 Hz, 3H).

Intermediate Example L

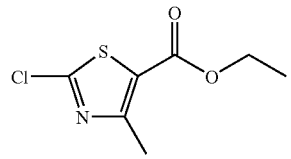

Ethyl 2-chloro-4-methyl-1,3-thiazole-5-carboxylate (X-1)

A mixture of ethyl 4-methyl-2-oxo-2,3-dihydro-1,3-thiazole-5-carboxylate (0.57 g, 3.05 mmol) and POCl$_3$ (5 mL) was heated at 120° C. for 18 h. Upon cooling, the mixture was concentrated. Water (15 mL) was slowly added and stirred for 10 min. The mixture was extracted with Et$_2$O (3×15 mL). The combined organics were dried with MgSO$_4$ and concentrated. The crude material was purified by chromatography (EtOAc/hexanes) to give the title compound as a white solid (0.54 g, 86%). $^1$H NMR (400 MHz, CDCl$_3$) δ 4.32 (q, J=7.1 Hz, 2H), 2.68 (s, 3H), 1.35 (t, J=7.1 Hz, 3H).

Intermediate Example M

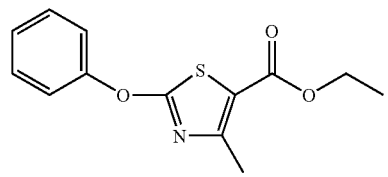

Ethyl 4-methyl-2-(phenyloxy)-1,3-thiazole-5-carboxylate (X-2a)

To a solution of ethyl 2-chloro-4-methyl-1,3-thiazole-5-carboxylate (X-1) (0.25 g, 1.22 mmol) and phenol (0.15 g, 1.61 mmol) in acetone (3 mL) was added K$_2$CO$_3$ (0.25 g, 1.81 mmol). The mixture was heated for 18 h at 65° C. Additional K$_2$CO$_3$ (0.25 g) was added and the mixture was continued to heat at 70° C. for 24 h. Upon cooling, water was added (10 mL). The mixture was extracted with Et$_2$O. The combined organics were dried with MgSO$_4$ and concentrated. The crude material was purified by chromatography (EtOAc/hexanes) to give the title compound as a white solid (0.18 g, 56%). $^1$H NMR (CDCl$_3$) δ 7.44 (m, 2H), 7.33-7.27 (m, 3H), 4.26 (q, J=7.1 Hz, 2H), 2.60 (s, 3H), 1.31 (t, J=7.1 Hz, 3H).

Intermediate Example N

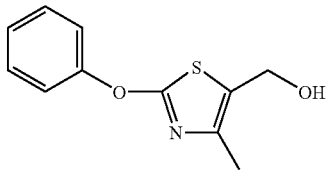

[4-Methyl-2-(phenyloxy)-1,3-thiazol-5-yl]methanol
(X-3a)

To a solution of ethyl 4-methyl-2-(phenyloxy)-1,3-thiazole-5-carboxylate (X-2a) (0.18 g, 0.687 mmol) in THF (3 mL) at 0° C. was added a solution of 1M LAH in THF (2.10 mL, 2.10 mmol). The mixture was stirred at 0° C. for 2 h. Water was added (1 mL) followed by a solution of 1M NaOH (1 mL) and water (1 mL). The mixture was filtered through a pad of Celite, and the Celite was washed with EtOAc. The filtrate was concentrated, and the crude material was purified by chromatography (EtOAc/hexanes) to give the title compound as a colorless oil (0.12 g, 80%). $^1$H NMR (400 MHz, CDCl$_3$) δ 7.40 (t, J=8.0 Hz, 2H), 7.25 (m, 3H), 4.66 (s, 2H), 2.26 (s, 3H).

Intermediate Example O

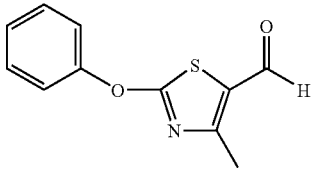

4-Methyl-2-(phenyloxy)-1,3-thiazole-5-carbaldehyde
(X-4a)

A mixture of [4-methyl-2-(phenyloxy)-1,3-thiazol-5-yl]methanol (X-3a) (0.109 g, 0.492 mmol) and MnO$_2$ (0.22 g, 2.56 mmol) in chloroform (2.5 mL) was stirred at RT for 2 h. More MnO$_2$ was added (0.22 g) and continued to stir overnight. Additional MnO$_2$ was added (0.40 g), and the mixture stirred for 3 days. The mixture was filtered through a pad of Celite, and the Celite was washed with EtOAc. The filtrate was concentrated, and the crude material was purified by chromatography (EtOAc/hexanes) to give the title compound as a colorless oil (0.086 g, 80%). $^1$H NMR (400 MHz, CDCl$_3$) δ 9.93 (s, 1H), 7.46 (t, J=8.0 Hz, 2H), 7.33 (t, J=7.4 Hz, 1H), 7.29-7.27 (m, 2H), 2.60 (s, 3H).

Scheme XI:

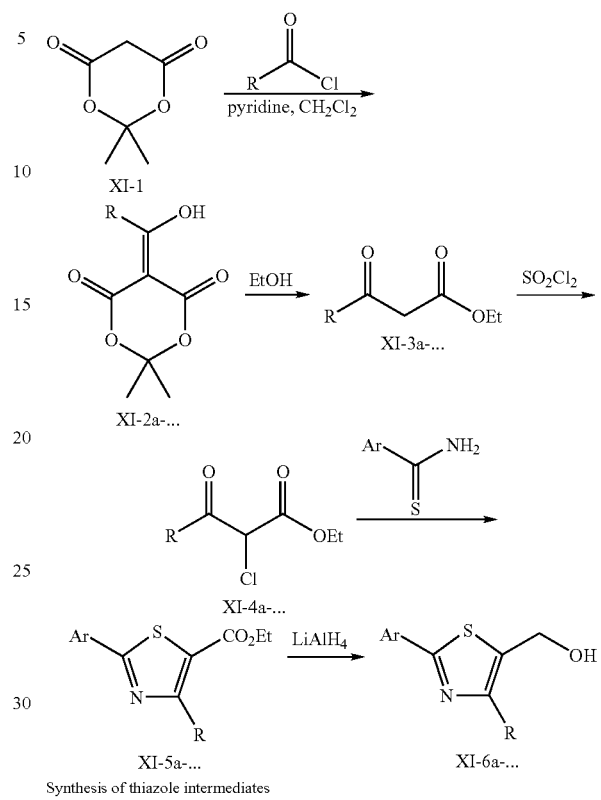

Synthesis of thiazole intermediates

Intermediate Example P

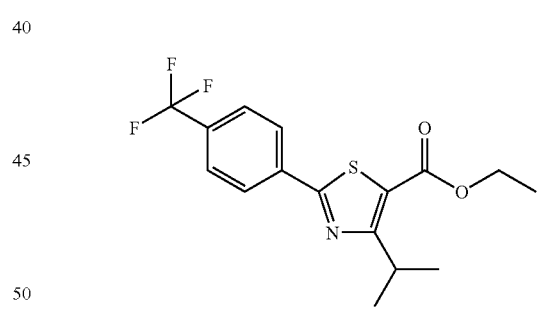

Ethyl 4-(1-methylethyl)-2-[4-(trifluoromethyl)phenyl]-1,3-thiazole-5-carboxylate (XI-5a)

Ethyl isobutyrylacetate (XI-3a) (3.006 g, 19.0 mmol) was dissolved in chloroform (20 mL). Sulfuryl chloride (1.70 mL, 21.2 mmol) was added and the solution was stirred at RT for 18 hours, then was concentrated. The residue was dissolved in ethanol (50 mL). 4-(Trifluoromethyl)benzenethioamide (4.234 g, 20.6 mmol) was added and the solution was heated to reflux for 24 hours. The mixture was cooled to RT and filtered. The solid was washed with cold ethanol and dried to provide the title product (2.68 g, 32%) as a pale yellow solid. $^1$H NMR (400 MHz, CDCl$_3$) δ 8.09 (d, J=8.1 Hz, 2H), 7.69 (d, J=8.1 Hz, 2H), 4.35 (q, J=7.1 Hz, 2H), 3.99 (qu, J=6.8 Hz, 1H), 1.39 (t, J=7.1 Hz, 3H), 1.35 (d, J=6.8 Hz, 6H).

Intermediate Example Q

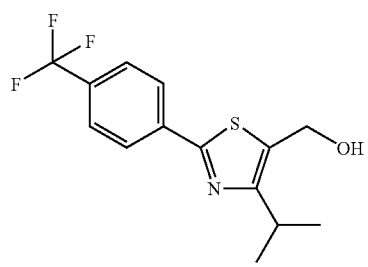

{4-(1-Methylethyl)-2-[4-(trifluoromethyl)phenyl]-1,3-thiazol-5-yl}methanol (XI-6a)

Ethyl 4-(1-methylethyl)-2-[4-(trifluoromethyl)phenyl]-1,3-thiazole-5-carboxylate (XI-5a) (2.68 g, 7.80 mmol) was dissolved in THF (8 mL) and cooled to 0° C. under nitrogen. Lithium aluminum hydride (1.0M solution in THF, 8.00 mL, 8.00 mmol) was added and the mixture was stirred at 0° C. for 60 min. Water (0.3 mL) was added, followed by 15% aqueous sodium hydroxide (0.3 mL), then water (0.9 mL). The resulting mixture was filtered and the filtrate was concentrated to provide the title compound (2.13 g, 91%) as a yellow solid. $^1$H NMR (400 MHz, CDCl$_3$) δ 8.03 (d, J=8.3 Hz, 2H), 7.65 (d, J=8.3 Hz, 2H), 4.86 (d, J=5.2 Hz, 2H), 3.14 (qu, J=6.8 Hz, 1H), 1.33 (d, J=6.8 Hz, 6H).

Alternative synthetic methods may be apparent to those skilled in the art. For example, the route described in Scheme XII, below, alternatively may be used to make the compounds of the present invention.

Scheme XII:

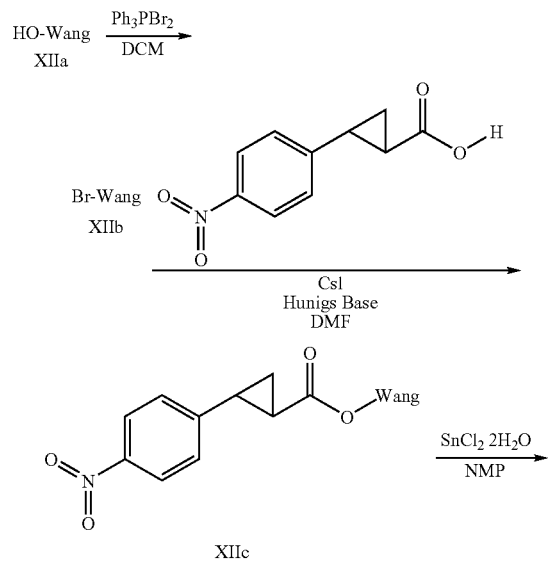

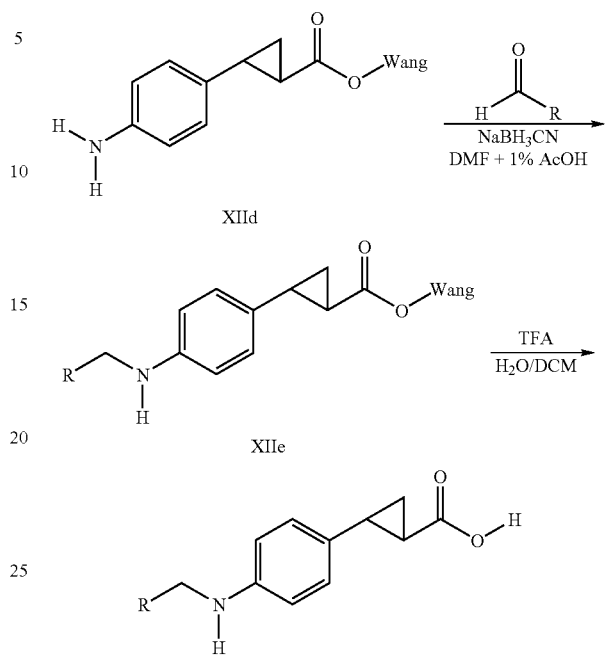

Table 1
Entries 1&2
Solid phase synthesis of racemic-(trans)-cyclopropanecarboxylic acid derivatives Preparation of Bromo-Wang Resin (XIIb)

To a suspension of Wang resin (XIIa) (5.0 g, 8.5 mmol, loading 1.7 mmol/g, bead size 150-300 μm, ex Polymer Labs) in dry DCM (50 mL) under argon was added a suspension of triphenylphosphine dibromide in DCM (75 mL) with gentle stirring over 10 min. The mixture was gently stirred for 3 h under argon and the resin was then filtered and washed with DCM, DMF and DCM (×4). The product was dried in a vacuum desiccator to give bromo-Wang resin (5.67 g).

Preparation of Wang Resin-Supported Racemic-(trans)-2-(4-nitrophenyl)cyclopropanecarboxylic Acid (XIIc)

To a suspension of bromo-Wang (XIIb) resin in dry DMF (~5 ml/mmol) was added racemic-(trans)-2-(4-nitrophenyl)cyclopropanecarboxylic acid (2.5 equivalents), cesium iodide (2.5 equivalents) and di-isopropylethylamine (2.5 equivalents). The mixture was shaken at room temperature for 20 h, and then filtered. The resin was washed with DMF-water (1:1), water (×2), DMF-water (1:1), DMF (×2), iPrOH (×2), DCM (×3) and MeOH. The product resin was dried in a vacuum oven at 40° C.

To verify the loading of the acid on the resin, a small quantity of the product was shaken with 40% trifluoroacetic acid, 2% water in DCM for 2 h. The resin was filtered and washed with DCM and MeCN, and the filtrate evaporated and dried in vacuo to give the cleaved product (86%).

Preparation of Wang Resin-Supported Racemic-(trans)-2-(4-aminophenyl)cyclopropanecarboxylic acid (XIId)

To a suspension of the Wang resin-supported racemic-(trans)-2-(4-nitrophenyl)cyclopropanecarboxylic acid (XIIc) in N-methylpyrrolidin-2-one (NMP, ~15 ml/mmol) was added tin chloride dihydrate (15 equiv.). The mixture was shaken for 67 h and then filtered. The product resin was washed with NMP (×2), DCM, dioxane, dioxane-water (1:1× 2), water (×2), dioxane-water (1:1×2) dioxane (×3), DCM (×3), methanol and ether, then dried in a vacuum oven at 40° C.

General Procedure for the Reductive Amination of Wang Resin-Supported Racemic-(trans)-2-(4-aminophenyl)cyclopropanecarboxylic Acid (XIIe)

To a suspension of the Wang resin-supported racemic-(trans)-2-(4-aminophenyl)cyclopropanecarboxylic acid (XIId) in a solution of 1% acetic acid in dry DMF under argon was added the aldehyde RCHO (10 equivalents). After shaking the mixture for 2 h, solid sodium cyanoborohydride (10 equivalents) was added, and the mixture was shaken for a further 20 h under argon. The mixture was filtered and the product resin washed with DMF, DMF-water (1:1), water (×2), DMF-water (1:1×2), DMF (×2), THF (×3) and DCM (×3). The resin product was dried in a vacuum oven at 40° C.

These reactions were either performed on individual resins or combinatorially using the IRORI directed sorting process. In the latter case, the resins were initially placed in IRORI microkans (0.04 mmol/kan) with a radiofrequency tag, and multiple kans were then reacted with different aldehydes in parallel.

General Procedure for Cleavage of the Products from the Wang Resin (Table 2, 1 &2)

The resin (XIIe) was shaken with 33% trifluoroacetic acid, 2.5% water in DCM for 2 h. The mixture was filtered and the resin washed with the cleavage solution. The filtrate was evaporated to give the desired product, which was dried in vacuo. In the combinatorial process the IRORI kans were placed in cleavage blocks and the resin products in each kan were cleaved in parallel to afford the individual products.

Each product was analysed by high throughput LC-MS and NMR and where necessary the products were purified in parallel using a Biotage Parallex preparative HPLC system (0.1% Trifluoroacetic acid-water, 0.1% trifluoroacetic acid-acetonitrile gradients used for both analytical and preparative hplc).

Examples of compounds synthesized in this fashion are shown below in Table 1.

TABLE 1

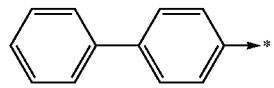

| Entry | pEC50 | R | Observed MH+* |
|---|---|---|---|
| 1 | 7.5 | 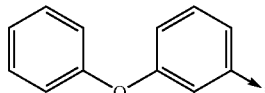 | 344 |
| 2 | 7.4 | | 360 |

Similarly, other synthetic methods not specifically disclosed herein may be used in the preparation of the compounds of the present invention.

Biological Data

GPR40 SAR Primary Assay

An existing stable GPR40 Elk-1/Gal4-luc+ CHO cell line generated by electroporation and functional cloning was used. Cells were maintained in a humidified incubator at 37° C./5% $CO_2$ in complete media containing DMEM/F12 (Gibco, #11039-021), 5% FBS (Gibco, #16140-071) and 1% Glutamine (Gibco, #25030-081). Cell maintenance passages were made at 1:40 dilution every 3-4 days. Forty eight hours prior to assay, 15e6 cells were added to 200 ml of complete media then seeded into a 1200 $cm^2$-cell factory and returned to a humidified incubator at 37° C./5% $CO_2$. 20 hours prior to assay, the growth media was removed and replaced with 200 ml of serum-free DMEM/F12 to quiesce background activity. At the time of assay, cells were harvested using non-enzymatic cell dissociation solution (Sigma, #C-5914), washed and counted. The 20 hour starve media was collected and used as condition media for cell assay plating. Cells were plated at a concentration of 10,000 cells/well in a total well volume of 100□l??? in black 96-well clear bottom polystyrene plates (CoStar, #3904). Test compounds were prepared as serial dilutions in 100% DMSO, then 1 ul was delivered to each well resulting in a final concentration of 1% DMSO. The plates were then returned to a humidified incubator at 37° C./5% $CO_2$ for 5 hours. Following the incubation, the medium was replaced with 50 ul of a 1:1 mixture of SteadyGlo™ (Promega, #E2550) and dPBS containing 1 mM $CaCl_2$ and 1 mM $MgCl_2$. Plates were then sealed and subjected to dark adaptation at room temperature for 10 minutes. Luciferase activity was measured on a Packard TopCount™ microplate scintillation counter using 2 seconds per well count time.

Data analysis was performed using standard methods.

The Normalization Equation used was 100*(Unknown compound response−Background response)/(Agonist Max response−Background response).

The Curve Fit Function used was $y=((V_{max}*x^n)/(K^n+x^n))+Y2$.

A percent max response and $pEC_{50}$ were recorded for each compound. Although specific $pEC_{50}$ values are given, these values should be considered exemplary. Those skilled in the art will appreciate the variability in performing and recording the biological activity assays that are herein described. The compounds of the present invention provide a $pEC_{50}$ of at least 5.0.

| Example # | $pEC_{50}$ |
|---|---|
| 1 | 7.9 |
| 2 | 7.6 |
| 3 | 5.8 |
| 4 | 8.7 |
| 5 | 7.7 |
| 6 | 7.8 |
| 7 | 7.7 |
| 8 | 8.2 |
| 9 | 8.1 |
| 10 | 8.0 |
| 11 | 6.9 |
| 12 | 6.4 |
| 13 | 7.7 |
| 14 | 7.8 |
| 15 | 6.9 |
| 16 | 7.2 |
| 17 | 6.6 |
| 18 | 6.6 |
| 19 | 7.2 |
| 20 | 6.8 |
| 21 | 7.6 |
| 22 | 6.5 |
| 23 | 7.5 |
| 24 | 6.7 |
| 25 | 6.2 |
| 26 | 8.4 |
| 27 | 8.4 |
| 28a | 8.5 |
| 29 | 6.5 |
| 30a | 6.4 |
| 31a | 6.3 |
| 32 | 8.3 |
| 33 | 7.6 |
| 34 | 8.1 |
| 35 | 7.7 |
| 36 | 6.6 |
| 37 | 8.0 |
| 38 | 8.3 |
| 39 | 8.0 |
| 40 | 7.3 |
| 41 | 8.2 |
| 42 | 8.1 |
| 43 | 7.7 |
| 44 | 8.0 |
| 45 | 8.0 |
| 46 | 7.2 |
| 47 | 8.0 |
| 48 | 7.5 |
| 49 | 7.5 |
| 50 | 6.6 |
| 51 | 7.3 |
| 52 | 7.8 |
| 53 | 8.0 |
| 54 | 7.7 |

As described hereinabove, GPR40 is an orphan G-protein coupled receptor isolated during a search for novel receptors. The ligands for GPR40 have been identified to be saturated and unsaturated fatty acids with carbon chain lengths greater than 6. mRNA expression of the receptor is primarily in human and rat pancreatic insulin-producing β-cells and in human brain. Activation of the receptor by fatty acids leads to an increase in intracellular calcium in HEK293 cells and CHO cells expressing human GPR40 through a Gαq-coupled signaling pathway.

Fatty acids are thought to be important in maintenance of basal insulin secretion in the fasting state and in potentiation of glucose-stimulated insulin secretion. Studies have shown that acute treatment of islets with fatty acids stimulates increases in intracellular calcium and glucose-stimulated insulin secretion. Nevertheless, the mechanisms behind the effect have not been elucidated. As discussed above and incorporated by reference, Itoh et al. demonstrated that reduction in expression of GPR40 using a specific RNAi in mouse insulinoma cell-line, namely MIN6 cells, partially reduces the ability of fatty acids to potentiate glucose-stimulated insulin secretion. This suggests that GPR40 plays a role in the 'priming' effect of fatty acids on insulin secretion from islets.

IVGTT Test in Normal Rats

The intravenous glucose-tolerance test is used to evaluate the responsiveness of the pancreatic α-cell, avoiding issues such as animal to animal variability in gastric motility and emptying and influences of gastrointestinal regulatory peptides and neuroregulatory peptides associated with giving an oral dose of glucose. GPR40 activation results in a decreased glucose AUC and an increased insulin AUC suggesting a potentiation of first-phase insulin secretion.

Glucose Stimulated Insulin Secretion from the MIN6 Mouse Insulinoma Cell Line

The MIN6 mouse insulinoma cell line has been used previously as a surrogate model to examine the effect of various agents on glucose-stimulated insulin secretion. The cell line has been demonstrated to exhibit the characteristics of glucose metabolism and glucose-stimulated insulin secretion similar to those of normal islets and has also been shown to express mRNA for GPR40 at levels at least equivalent to normal islets.

Although specific embodiments of the present invention are herein illustrated and described in detail, the invention should not necessarily be limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound of formula (I)

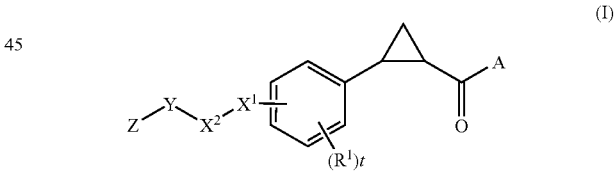

including salts thereof, wherein t is 0, 1, 2, 3, or 4;

$R^1$ is alkyl, alkoxy, halogen, haloalkyl, nitro, cyano, or —$NR^7R^8$, where each of $R^7$ and $R^8$ independently are H or alkyl;

A is —OH, $OR^9$ where $R^9$ is alkyl or aryl, or —$NR^2R^3$;

each of $R^2$ and $R^3$ independently is H or -($Q^1$)$_n$-$R^4$;

n is 0, 1 or 2;

$Q^1$ is alkylene;

each $R^4$ independently is alkyl, haloalkyl, aryl, heteroaryl, cycloalkyl, heterocyclyl, hydroxy, alkoxy, or aryloxy;

$X^1$ is —NH—;

$X^2$ is —C($R^5$)$_2$—;

each $R^5$ independently is H or alkyl;

Y is aryl or heteroaryl;

Z is -($Q^2$)$_m$-$R^6$;

m is 0 or 1;
Q² is —NR⁵—, —O—, —S—, —O(CH₂)$_p$—, or —CH₂—;
p is 1, 2, or 3; and
R⁶ is aryl or heteroaryl.

2. The compound of claim 1 wherein X² is —CH₂—.
3. The compound of claim 2 wherein X¹ is substituted para to the depicted cyclopropyl ring.
4. The compound of claim 1 wherein t is 0.
5. The compound of claim 1 wherein Y is aryl.
6. The compound of claim 5 wherein Y is phenyl.
7. The compound of claim 6 wherein said phenyl is unsubstituted or is optionally substituted with C₁-C₆ alkyl, C₁-C₆ alkoxy, halogen, or C₁-C₆ haloalkyl.
8. The compound of claim 1 wherein Y is heteroaryl.
9. The compound of claim 8 wherein Y is thiazolyl.
10. The compound of claim 9 wherein said thiazolyl is unsubstituted or is optionally substituted with C₁-C₆ alkyl, aryl, or heteroaryl.
11. The compound of claim 1 wherein A is —OH.
12. The compound of claim 1 wherein Q¹ is unsubstituted alkylene.
13. The compound of claim 1 wherein Q¹ is optionally substituted alkylene.
14. The compound of claim 1 wherein Z is —O—R⁶.
15. The compound of claim 14 wherein R⁶ is phenyl.
16. The compound of claim 15 wherein said phenyl is unsubstituted or is optionally substituted with halogen, C₁-C₆ haloalkyl, or C₁-C₆ alkoxy.
17. The compound of claim 1 wherein Z is —R⁶.
18. The compound of claim 17 wherein R⁶ is phenyl.
19. The compound of claim 18 wherein said phenyl is unsubstituted or is optionally substituted with halogen, C₁-C₆ haloalkyl, or C₁-C₆ alkoxy.
20. The compound of claim 19 wherein R⁶ is heteroaryl.
21. The compound of claim 1 wherein A is —OH, t is 0, X¹ is —NH—, X² is —CH₂—, Y is phenyl, m is 1, Q² is —O—, and R⁶ is phenyl.
22. The compound of claim 1 wherein A is —OH, t is 0, X¹ is —NH—, X² is —CH₂—, Y is thiazolyl, m is 0, and R⁶ is phenyl substituted with —CF₃.
23. The compound of claim 1 wherein the compound is selected from:

Racemic-(trans)-2-[4-({[3-(phenyloxy)phenyl]methyl}ammonium)phenyl]cyclopropanecarboxylic acid;
Racemic-(trans)-2-{4-[(4-biphenylylmethyl)amino]phenyl}cyclopropanecarboxylic acid;
Racemic-(trans)-2-[4-({[4-(2-pyridinyl) phenyl]methyl}amino)phenyl]cyclopropanecarboxylic acid;
Racemic-(trans)-2-{4-[({3-[(3,4-dichlorophenyl)oxy]phenyl}methyl)ammonium]phenyl}-cyclopropanecarboxylic acid;
Racemic-(trans)-2-(4-{[(3-{[4-(methyloxy)phenyl]oxy}phenyl)methyl]ammonium}phenyl)-cyclopropanecarboxylic acid;
Racemic-(trans)-2-{4-[({3-[(4-chlorophenyl)oxy]phenyl}methyl)ammonium]phenyl}-cyclopropanecarboxylic acid;
Racemic-(trans)-2-(4-{[(3-{[4-(1,1-dimethylethyl)phenyl]oxy}phenyl)methyl]ammonium}phenyl)cyclopropanecarbox ylic acid;
Racemic-(trans)-2-{4-[({3-[(3,5-dichlorophenyl)oxy]phenyl}methyl)ammonium]phenyl}-cyclopropanecarboxylic acid;
Racemic-(trans)-2-(4-{[(3-{[3-(trifluoromethyl)phenyl]oxy}phenyl)methyl]ammonium}-phenyl)cyclopropanecarboxylic acid;
Racemic-(trans)-2-{4-[({3-[(4-methylphenyl)oxy]phenyl}methyl)ammonium]phenyl}-cyclopropanecarboxylic acid;
Racemic-(trans)-2-{4[({3-[(phenylmethyl)oxy]phenyl}methyl)ammonium]phenyl}-cyclopropanecarboxylic acid;
Racemic-(trans)-2-[4-({[4-methyl-2-(phenyloxy)-1,3-thiazol-5-yl]methyl}ammonium)-phenyl]cyclopropanecarboxylic acid;
Racemic-(trans)-2-{4-[({4-methyl-2-[4-(trifluoromethyl)phenyl]-1,3-thiazol-5-yl}methyl)amino]phenyl}cyclopropanecarboxylic acid;
Racemic-(trans)-2-{4-[({4-isopropyl-2-[4-(trifluoromethyl)phenyl]-1,3-thiazol-5-yl}methyl)amino]phenyl}cyclopropanecarboxylic acid;
Racemic-(trans)-2-[4-({[5-(4-chlorophenyl)-2-furanyl]methyl}amino)phenyl]cyclopropanecarboxylic acid;
Racemic-(trans)-2-{4-[({4-[(phenylmethyl)oxy]phenyl}methyl)amino]phenyl}cyclopropanecarboxylic acid;
Racemic-(trans)-2-{4-[({2-[(3,4-difluorophenyl)oxy]-4-methyl-1,3-thiazol-5-yl}methyl)amino]phenyl}cyclopropanecarboxylic acid;
Racemic-(trans)-2-{4-[({5-[4-(trifluoromethyl)phenyl]-2-furanyl}methyl)amino]phenyl}cyclopropanecarboxylic acid;
Racemic-(trans)-2-{4-[({5-[4-(trifluoromethyl)phenyl]-2-thienyl}methyl)amino]phenyl}cyclopropanecarboxylic acid;
Racemic-(trans)-2-{4-[({4-[4-(trifluoromethyl)phenyl]-2-furanyl}methyl)amino]phenyl}cyclopropanecarboxylic acid;
Racemic-(trans)-2-[4-({[3-(phenylmethyl)phenyl]methyl}amino)phenyl]cyclopropanecarboxylic acid;
Racemic-(trans)-2-{4-[({3-[(4-nitrophenyl)oxy]phenyl}methyl)amino]phenyl}cyclopropanecarboxylic acid;
Racemic-(trans)-2-[4-({[3-(phenylthio)phenyl]methyl}amino)phenyl]cyclopropanecarboxylic acid;
Racemic-(trans)-2-{4-[({3-[(4-aminophenyl)oxy]phenyl}methyl)amino]phenyl}cyclopropanecarboxylic acid;
(−)-(Trans)-2-[4-({[3-(phenyloxy)phenyl]methyl}amino)phenyl]cyclopropanecarboxylic acid;
(+)-(Trans)-2-{4-[(3-phenoxybenzyl)amino]phenyl}cyclopropanecarboxylic acid;
(+)-(Trans)-2-{4-[({4-methyl-2-[4-(trifluoromethyl)phenyl]-1,3-thiazol-5-yl}methyl)amino]phenyl}cyclopropanecarboxylic acid;
Enantiomerically enriched (trans)-ethyl-2-{4-[({3-[(3,4-dichlorophenyl)oxy]phenyl}methyl)amino]phenyl}-cyclopropanecarboxylate;
(+)-(Trans)-2-{4-[({3-[(3,4-dichlorophenyl)oxy]phenyl}methyl)amino]phenyl}cyclopropanecarboxylic acid;
(−)-(cis)-2-{4-[({4-methyl-2-[4-(trifluoromethyl)phenyl]-1,3-thiazol-5-yl}methyl)amino]phenyl}cyclopropanecarboxylic acid;
Enantiomerically enriched-(trans)-ethyl-2-[2-chloro-4-({[3-(phenyloxy)phenyl]methyl}amino)phenyl]cyclopropanecarboxylate;
(+)-(Trans)-2-[2-chloro-4-({[3-(phenyloxy) phenyl]methyl}amino)phenyl]cyclopropanecarboxylic acid;

Enantiomerically enriched-(trans)-ethyl-2-[2,5-difluoro-4-({[3-(phenyloxy) phenyl]methyl}amino)phenyl]cyclopropanecarboxylate;
(+)-(trans)-2-[2,5-difluoro-4-({[3-(phenyloxy)phenyl]methyl}amino)phenyl]cyclopropanecarboxylic acid;
(+)-(trans)-2-{4-[({3-[(3,5-dichlorophenyl)oxy]phenyl}methyl)amino]phenyl}cyclopropanecarboxylic acid;
(+)-(trans)-2-(4-{[(3-{[3-(trifluoromethyl)phenyl]oxy}phenyl)methyl]amino}phenyl)cyclopropanecarboxylic acid;
(+)-(trans)-2-{4-[({3-[(4-methylphenyl)oxy]phenyl}methyl)amino]phenyl}-cyclopropanecarboxylic acid;
Racemic-(trans)-2-{4-[(4-biphenylmethyl)amino]phenyl}cyclopropanecarboxamide;
Racemic-(trans)-2-[4-({[4-(2-pyridinyl)phenyl]methyl}amino)phenyl]cyclopropanecarboxamide;
Racemic-(trans)-2-{4-[({4-methyl-2-[4-(trifluoromethyl)phenyl]-1,3-thiazol-5-yl}methyl)amino]phenyl}-N-(4-pyridinylmethyl)cyclopropanecarboxamide;
Enantiomerically enriched (trans)-2-{4-[({4-methyl-2-[4-(trifluoromethyl)phenyl]-1,3-thiazol-5-yl}methyl)amino]phenyl}-N-(4-pyridinylmethyl)cyclopropanecarboxamide;
Enantiomerically enriched (trans)-2-{4-[({4-methyl-2-[4-(trifluoromethyl)phenyl]-1,3-thiazol-5-yl}methyl)amino]phenyl}cyclopropanecarboxamide;
Enantiomerically enriched (trans)-2-{4-[({4-methyl-2-[4-(trifluoromethyl)phenyl]-1,3-thiazol-5-yl}methyl)amino]phenyl}-N-[(1S)-1-phenylethyl]cyclopropanecarboxamide;
Enantiomerically enriched (trans)-N-hydroxy-2-{4[({4-methyl-2-[4-(trifluoromethyl)phenyl]-1,3-thiazol-5-yl}methyl)amino]phenyl}cyclopropanecarboxamide;
Enantiomerically enriched (trans)-N-cyclobutyl-2-{4-[({4-methyl-2-[4-(trifluoromethyl)phenyl]-1,3-thiazol-5-yl}methyl)amino]phenyl}cyclopropanecarboxamide;
Racemic-(trans)-2-{4-[({4-methyl-2-[4-(trifluoromethyl)phenyl]-1,3-thiazol-5-yl}methyl)amino]phenyl}cyclopropanecarboxamide;
(+)-(trans)-N-(1-methylethyl)-2-[4-({[3-(phenyloxy)phenyl]methyl}amino)phenyl]cyclopropanecarboxamide;
Racemic-(trans)-N-isopropyl-2-{4-[({4-methyl-2-[4-(trifluoromethyl)phenyl]-1,3-thiazol-5-yl}methyl)amino]phenyl}cyclopropanecarboxamide;
Racemic-(trans)-N,N-dimethyl-2-{4-[({4-methyl-2-[4-(trifluoromethyl)phenyl]-1,3-thiazol-5-yl}methyl)amino]phenyl}cyclopropanecarboxamide;
Racemic-(trans)-2-[4-({[3-(phenyloxy)phenyl]methyl}amino)phenyl]-N-(4-pyridinylmethyl)cyclopropanecarboxamide;
Racemic-(trans)-N-(4-methoxybenzyl)-2-{4-[(3-phenoxybenzyl)amino]phenyl}cyclopropanecarboxamide;
Racemic-(trans)-2-{4-[(3-phenoxybenzyl)amino]phenyl}-N-[4-(trifluoromethyl)benzyl]cyclopropanecarboxamide;
Racemic-(trans)-N-(2-morpholin-4-ylethyl)-2-{4-[(3-phenoxybenzyl)amino]phenyl}cyclopropanecarboxamide;
Racemic-(trans)-2-{4-[(3-phenoxybenzyl)amino]phenyl}-N-(2,2,2-trifluoroethyl)cyclopropanecarboxamide;
Racemic-(trans)-N-isopropyl-2-{4-[({4-isopropyl-2-[4-(trifluoromethyl)phenyl]-1,3-thiazol-5-yl}methyl)amino]phenyl}cyclopropanecarboxamide; and
Enantiomerically enriched N-isopropyl-2-{4-[({4-methyl-2-[4-(trifluoromethyl) phenyl]-1,3-thiazol-5-yl}methyl)amino]phenyl}cyclopropanecarboxamide; and
Enantiomerically enriched N-(cyclopropylmethyl)-2-{4 [(3-phenoxybenzyl) amino] phenyl}cyclopropanecarboxamide, including salts thereof.

24. A pharmaceutical composition comprising a compound according to claim 1, and a pharmaceutically acceptable carrier.

* * * * *